(12) United States Patent
Faure et al.

(10) Patent No.: US 9,273,111 B2
(45) Date of Patent: *Mar. 1, 2016

(54) THERAPEUTIC TREM-1 PEPTIDES

(75) Inventors: Gilbert Faure, Vandoeuvre les Nancy (FR); Sebastien Gibot, Vandoeuvre les Nancy (FR); Paola Panina, Milan (IT); Nadia Passini, Milan (IT)

(73) Assignees: Universite de Lorraine, Nancy (FR); Bristol-Myers Squibb, Princeton, NJ (US)

( * ) Notice: Subject to any disclaimer, the term of this patent is extended or adjusted under 35 U.S.C. 154(b) by 71 days.

This patent is subject to a terminal disclaimer.

(21) Appl. No.: 13/181,323

(22) Filed: Jul. 12, 2011

(65) Prior Publication Data

US 2012/0015867 A1    Jan. 19, 2012

Related U.S. Application Data

(63) Continuation of application No. 12/320,707, filed on Feb. 2, 2009, now Pat. No. 8,013,116, which is a continuation-in-part of application No. 11/284,086, filed on Nov. 22, 2005, now abandoned.

(30) Foreign Application Priority Data

Nov. 29, 2004  (GB) .................................. 0426146.7
May 19, 2005   (JP) ................................ 2005-146848

(51) Int. Cl.
| | |
|---|---|
| *A61K 38/16* | (2006.01) |
| *C07K 7/08* | (2006.01) |
| *C12N 15/12* | (2006.01) |
| *A61P 31/00* | (2006.01) |
| *A61P 7/00* | (2006.01) |
| *C07K 14/705* | (2006.01) |
| *G01N 33/50* | (2006.01) |
| *A61K 38/00* | (2006.01) |

(52) U.S. Cl.
CPC .......... *C07K 14/705* (2013.01); *G01N 33/5088* (2013.01); *A61K 38/00* (2013.01); *G01N 2800/065* (2013.01); *G01N 2800/26* (2013.01)

(58) Field of Classification Search
None
See application file for complete search history.

(56) References Cited

U.S. PATENT DOCUMENTS

| | | |
|---|---|---|
| 4,444,887 A | 4/1984 | Hoffmann |
| 4,522,811 A | 6/1985 | Eppstein et al. |
| 4,676,980 A | 6/1987 | Segal et al. |
| 4,683,195 A | 7/1987 | Mullis et al. |
| 4,683,202 A | 7/1987 | Mullis |
| 4,716,111 A | 12/1987 | Osband et al. |
| 4,736,866 A | 4/1988 | Leder et al. |
| 4,741,900 A | 5/1988 | Alvarez et al. |
| 4,816,397 A | 3/1989 | Boss et al. |
| 4,816,567 A | 3/1989 | Cabilly et al. |
| 4,870,009 A | 9/1989 | Evans et al. |
| 4,873,191 A | 10/1989 | Wagner et al. |
| 4,873,316 A | 10/1989 | Meade et al. |
| 4,946,778 A | 8/1990 | Ladner et al. |
| 4,980,286 A | 12/1990 | Morgan et al. |
| 4,987,071 A | 1/1991 | Cech et al. |
| 5,116,742 A | 5/1992 | Cech et al. |
| 5,223,409 A | 6/1993 | Ladner et al. |
| 5,225,539 A | 7/1993 | Winter |
| 5,258,498 A | 11/1993 | Huston et al. |
| 5,272,057 A | 12/1993 | Smulson et al. |
| 5,272,071 A | 12/1993 | Chappel |
| 5,283,317 A | 2/1994 | Saifer et al. |
| 5,328,470 A | 7/1994 | Nabel et al. |
| 5,403,484 A | 4/1995 | Ladner et al. |
| 5,413,923 A | 5/1995 | Kucherlapati et al. |
| 5,420,526 A | 5/1995 | Fensch |
| 5,424,286 A | 6/1995 | Eng |
| 5,427,908 A | 6/1995 | Dower et al. |
| 5,436,146 A | 7/1995 | Shenk et al. |
| 5,459,039 A | 10/1995 | Modrich et al. |
| 5,474,981 A | 12/1995 | Leder et al. |
| 5,498,531 A | 3/1996 | Jarrell |
| 5,516,637 A | 5/1996 | Huang et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,698,426 A | 12/1997 | Huse |
| 5,733,743 A | 3/1998 | Johnson et al. |

(Continued)

FOREIGN PATENT DOCUMENTS

| | | |
|---|---|---|
| CA | 2342376 A1 | 9/2002 |
| EP | 239400 A2 | 9/1987 |

(Continued)

OTHER PUBLICATIONS

Aderem et al., "Toll-like receptors in the induction of the innate immune response," Nature, Aug. 17, 2000, vol. 406, pp. 782-786.

(Continued)

*Primary Examiner* — Sharon Wen

(74) *Attorney, Agent, or Firm* — Nelson Mullins Riley & Scarborough LLP; Jane E. Remillard, Esq.

(57) ABSTRACT

A polypeptide comprising one or more sequences derived from CDR2 or CDR3 of a TREM-1 protein, characterized by the ability to treat, ameliorate, or lessen the symptoms of conditions including sepsis, septic shock or sepsis-like conditions and IBD.

10 Claims, 18 Drawing Sheets

(56) References Cited

U.S. PATENT DOCUMENTS

Figure 2:
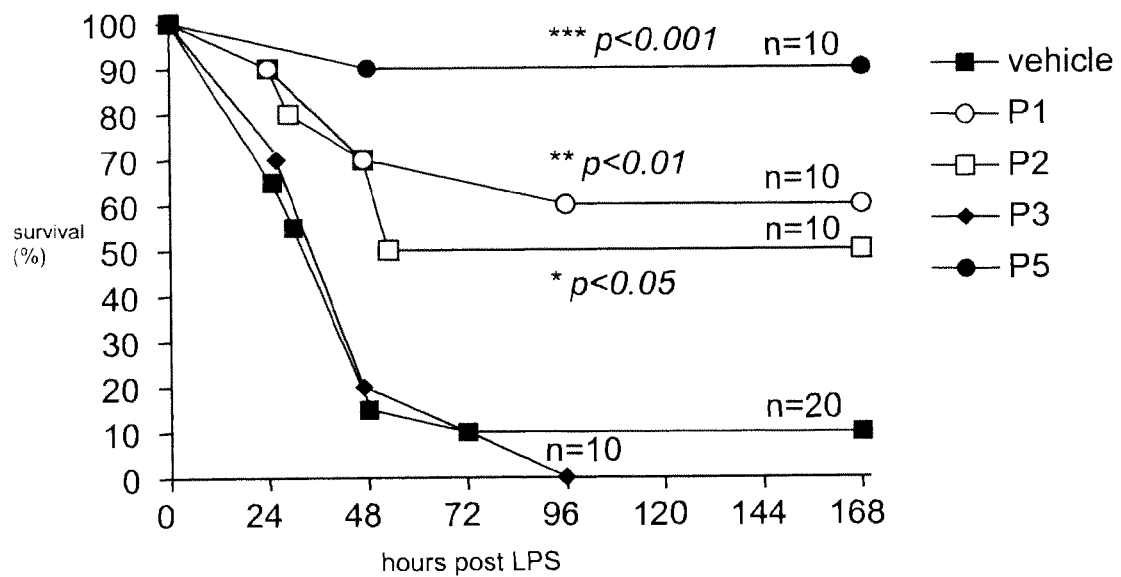

| | | | |
|---|---|---|---|
| 5,750,753 A | 5/1998 | Kimae et al. |
| 5,780,225 A | 7/1998 | Wigler et al. |
| 5,807,715 A | 9/1998 | Morrison et al. |
| 5,814,318 A | 9/1998 | Lonberg et al. |
| 5,821,047 A | 10/1998 | Garrard et al. |
| 5,885,793 A | 3/1999 | Griffiths et al. |
| 5,916,771 A | 6/1999 | Hori et al. |
| 5,939,598 A | 8/1999 | Kucherlapati et al. |
| 5,969,108 A | 10/1999 | McCafferty et al. |
| 6,420,526 B1 | 7/2002 | Ruben et al. |
| 6,504,010 B1 | 1/2003 | Wang et al. |
| 6,509,448 B2 | 1/2003 | Wang et al. |
| 6,858,204 B2 | 2/2005 | Henderson et al. |
| 6,878,687 B1 | 4/2005 | Ruben et al. |
| 8,013,116 B2 * | 9/2011 | Faure et al. | 530/326 |
| 2002/0128444 A1 * | 9/2002 | Gingras et al. | 530/350 |
| 2002/0172952 A1 | 11/2002 | Henderson et al. |
| 2002/0197669 A1 | 12/2002 | Bangur et al. |
| 2003/0049618 A1 | 3/2003 | Ruben et al. |
| 2003/0054363 A1 | 3/2003 | Henderson et al. |
| 2003/0077282 A1 | 4/2003 | Bigler et al. |
| 2003/0134283 A1 | 7/2003 | Peterson et al. |
| 2003/0165875 A1 | 9/2003 | Colonna et al. |
| 2003/0170255 A1 | 9/2003 | Watanabe et al. |
| 2003/0175858 A1 | 9/2003 | Ruben et al. |
| 2003/0211510 A1 | 11/2003 | Henderson et al. |
| 2005/0255114 A1 | 11/2005 | Labat et al. |
| 2006/0183125 A1 | 8/2006 | Mariani et al. |
| 2010/0310560 A1 | 12/2010 | Colonna et al. |

FOREIGN PATENT DOCUMENTS

| | | | |
|---|---|---|---|
| EP | 264166 A1 | 4/1988 |
| EP | 439098 A2 | 7/1991 |
| EP | 519596 A1 | 12/1992 |
| EP | 592106 A1 | 4/1994 |
| EP | 1022286 A1 | 7/2000 |
| EP | 1498424 A2 | 1/2005 |
| WO | 88/09810 A1 | 12/1988 |
| WO | 89/10134 A1 | 11/1989 |
| WO | 90/02809 A1 | 3/1990 |
| WO | 90/11354 A1 | 10/1990 |
| WO | 91/01140 A1 | 2/1991 |
| WO | 91/06667 A1 | 5/1991 |
| WO | 91/09967 A1 | 7/1991 |
| WO | 91/10737 A1 | 7/1991 |
| WO | 91/10741 A1 | 7/1991 |
| WO | 92/00968 A1 | 1/1992 |
| WO | 92/01047 A1 | 1/1992 |
| WO | 92/06180 A1 | 4/1992 |
| WO | 92/18619 A1 | 10/1992 |
| WO | 92/20316 A2 | 11/1992 |
| WO | 92/22324 A1 | 12/1992 |
| WO | 92/22635 A1 | 12/1992 |
| WO | 93/04169 A1 | 3/1993 |
| WO | 93/11236 A1 | 6/1993 |
| WO | 93/14188 A1 | 7/1993 |
| WO | 93/20221 A1 | 10/1993 |
| WO | 93/21232 A1 | 10/1993 |
| WO | 94/08598 A1 | 4/1994 |
| WO | 94/10300 A1 | 5/1994 |
| WO | 9412649 A2 | 6/1994 |
| WO | 94/16101 A2 | 7/1994 |
| WO | 95/15982 A2 | 6/1995 |
| WO | 95/20401 A1 | 8/1995 |
| WO | 96/33735 A1 | 10/1996 |
| WO | 96/34096 A1 | 10/1996 |
| WO | 97/07668 A1 | 3/1997 |
| WO | 97/07669 A1 | 3/1997 |
| WO | 98/08871 | 3/1998 |
| WO | 98/16654 A1 | 4/1998 |
| WO | 98/24893 A2 | 6/1998 |
| WO | 98/39446 A2 | 9/1998 |
| WO | 98/39448 A2 | 9/1998 |
| WO | 98/46645 A2 | 10/1998 |
| WO | 98/50433 A2 | 11/1998 |
| WO | 00/00610 A2 | 1/2000 |
| WO | 01/53312 A1 | 7/2001 |
| WO | 01/90304 A2 | 11/2001 |
| WO | WO 02/058721 A1 | 8/2002 |
| WO | 03/011213 A2 | 2/2003 |
| WO | 03/025138 A2 | 3/2003 |
| WO | 03/030835 A2 | 4/2003 |
| WO | 03/037267 A2 | 5/2003 |
| WO | 03/060071 A2 | 7/2003 |
| WO | 03/061712 A1 | 7/2003 |
| WO | 03/080667 A2 | 10/2003 |
| WO | 2004/020591 A2 | 3/2004 |
| WO | WO 2004/081233 A1 | 9/2004 |
| WO | 2005/048823 A2 | 6/2005 |
| WO | 2005/071408 A1 | 8/2005 |
| WO | 2005/091944 | 10/2005 |
| WO | 2005/113606 A2 | 12/2005 |
| WO | 2006/028595 A2 | 3/2006 |
| WO | 2006/028714 A1 | 3/2006 |
| WO | 2006/056492 A1 | 6/2006 |
| WO | 2006/065582 A2 | 6/2006 |
| WO | 2006/078463 A2 | 7/2006 |
| WO | 2006/097537 A2 | 9/2006 |
| WO | 2006/135886 A2 | 12/2006 |
| WO | 2007/146968 A2 | 12/2007 |
| WO | 2008/088849 A2 | 7/2008 |
| WO | 2008/121563 A2 | 10/2008 |
| WO | 2009/018386 A1 | 2/2009 |
| WO | 2009/020802 A2 | 2/2009 |
| WO | 2009/030771 A1 | 3/2009 |
| WO | 2009/117033 A2 | 9/2009 |
| WO | 2009/126380 A2 | 10/2009 |
| WO | 2009/141359 A1 | 11/2009 |
| WO | 2010/006060 A2 | 1/2010 |
| WO | 2010/042747 A2 | 4/2010 |
| WO | 2010/044952 A2 | 4/2010 |
| WO | 2010/065439 A1 | 6/2010 |
| WO | 2010/084169 A2 | 7/2010 |
| WO | 2010/132370 A2 | 11/2010 |
| WO | 2010/142665 A1 | 12/2010 |
| WO | 2011/005481 A1 | 1/2011 |
| WO | 2011/028952 A1 | 3/2011 |
| WO | 2011/047097 A2 | 4/2011 |
| WO | 2011/069104 A2 | 6/2011 |
| WO | 2011/091078 A2 | 7/2011 |
| WO | 2011/137362 | 11/2011 |
| WO | 2012/064733 | 5/2012 |
| WO | 2012/088290 | 6/2012 |
| WO | 2012/088302 | 6/2012 |
| WO | 2012/109624 | 8/2012 |

OTHER PUBLICATIONS

Adrie et al., "Postresuscitation disease after cardiac arrest: a sepsis-like syndrome?", Current Opinion in Critical Care, Jun. 2004, vol. 10, pp. 208-212.

Bleharski et al., "A Role for Triggering Receptor Expressed on Myeloid Cells-1 in Host Defense During the Early-Induced and Adaptive Phases of the Immune Response," The Journal of Immunology, 2003, vol. 170, pp. 3812-3818.

Bone et al., "Definitions for Sepsis and Organ Failure and Guidelines for the Use of Innovative Therapies in Sepsis," Chest, Jun. 1992, vol. 101, pp. 1644-1655.

Bouchon et al., "TREM-1 amplifies inflammation and is a crucial mediator of septic shock," Nature, Apr. 26, 2001, vol. 410, pp. 1103-1107.

Bouchon et al., "Cutting Edge: Inflammatory Responses Can Be Triggered by TREM-1, a Novel Receptor Expressed on Neutrophils and Monocytes," J. Immunol., 2000, vol. 164, pp. 4991-4995.

Cohen, Jonathan, "TREM-1 in sepsis," The Lancet, Sep. 8, 2001, vol. 358, pp. 776-778.

Collart et al., "Regulation of Tumor Necrosis Factor Alpha Transcription in Macrophages: Involvement of Four $_\kappa$B-Like Motifs and of Constitutive and Inducible Forms of NF-$_\kappa$B," Molecular and Cellular Biology, Apr. 1990, vol. 10, No. 4, pp. 1498-1506.

(56) References Cited

OTHER PUBLICATIONS

Colonna et al., "TREM-1 (Triggering Receptor Expressed on Myeloid Cells): A New Player in Acute Inflammatory Responses," Journal of Infectious Diseases, 2003, 187, suppl. 2: pp. S397-S401.

Colonna et al., "TREMS in the Immune System and Beyond," Nature Reviews Immunology, Jun. 2003, vol. 3, No. 6, pp. 445-453 (printed as pp. 1-9).

Dinarello et al., "Proinflammatory and Anti-inflammatory Cytokines as Mediators in the Pathogenesis of Septic Shock," Chest, Dec. 1997, vol. 112, No. 6, pp. 321S-329S.

Echtenacher et al., "Tumor Necrosis Factor-Dependent Adhesions as a Major Protective Mechanism Early in Septic Peritonitis in Mice," Infection and Immunity, Jun. 2001, vol. 69, No. 6, pp. 3550-3555.

Echtenacher et al., "Requirement of Endogenous Tumor Necrosis Factor/Cachectin for Recovery from Experimental Peritonitis ," Journal of Immunology, Dec. 1, 1990, vol. 145, No. 11, pp. 3762-3766.

Eskandari et al., "Anti-tumor Necrosis Factor Antibody Therapy Fails to Prevent Lethality After Cecal Ligation and Puncture or Endotoxemia," Journal of Immunology, May 1, 1992, vol. 148, No. 9, pp. 2724-2730.

Fisher et al., "Treatment of Septic Shock with the Tumor Necrosis Factor Receptor:Fc Fusion Protein," The New England Journal of Medicine, 1996, vol. 334, No. 26, pp. 1697-1702.

Gibot et al., "A Soluble Form of the Triggering Receptor Expressed on Myeloid Cells-1 Modulates the Inflammatory Response in Murine Sepsis," The Journal of Experimental Medicine, Dec. 6, 2004, vol. 200, No. 11, pp. 1419-1426.

Gibot et al., "Soluble Triggering Receptor Expressed on Myeloid Cells and the Diagnosis of Pneumonia," The New England Journal of Medicine, Jan. 29, 2004, vol. 350, No. 5, pp. 451-458.

Gibot et al., "Plasma Level of a Triggering Receptor Expressed on Myeloid Cells-1: Its Diagnostic Accuracy in Patients with Suspected Sepsis," Ann. Intern. Med., 2004, vol. 141, pp. 9-15.

Gingras et al., "*TREM-1, MDL-1* and *DAP12* expression is associated with a mature stage of myeloid development," Molecular Immunology, 2001, vol. 38, pp. 817-824.

Griffin et al., "Abnormal Heart Rate Characteristics Preceding Neonatal Sepsis and Sepsis-Like Illness," Pediatric Research, 2003, vol. 53, No. 6, pp. 920-926.

Hiscott et al., "Characterization of a Functional NF-$_\kappa$B Site in the Human Interleukin 1β Promoter: Evidence for a Positive Autoregulatory Loop," Molecular and Cellular Biology, Oct. 1993, vol. 13, No. 10, pp. 6231-6240.

Keane et al., "Tuberculosis Associated with Infliximab, a Tumor Necrosis Factor α-Neutralizing Agent," The New England Journal of Medicine, Oct. 11, 2001, vol. 345, No. 15, pp. 1098-1104.

Kelker et al., "Crystal Structure of Human Triggering Receptor Expressed on Myeloid Cells 1 (TREM-1) at 1.47 Å," J. Mol. Biol. 2004, vol. 342, pp. 1237-1248.

Lantz et al., "Characterization In Vitro of a Human Tumor Necrosis Factor-binding Protein: A Soluble Form of a Tumor Necrosis Factor Receptor," J. Clin. Invest., Nov. 1990, vol. 86, pp. 1396-1402.

Lolis et al., "Therapeutic Approaches to Innate Immunity: Severe Sepsis and Septic Shock," Nature, Aug. 2003, vol. 2, pp. 635-645.

Medzitov et al., "Innate Immunity," The New England Journal of Medicine, Aug. 3, 2000, pp. 338-344.

Nathan et al., "TREM-1: A new regulator of innate immunity in sepsis syndrome," Nature Medicine, May 2001, vol. 7, No. 5, pp. 530-532.

NCBI Reference Sequences (RefSeq) NP_061113 (3pgs.).

NCBI Reference Sequences (RefSeq) NP_067381 (2 pgs.).

Radaev et al., "Crystal Structure of the Human Myeloid Cell Activating Receptor TREM-1," Structure, Dec. 2003, vol. 11, pp. 1527-1535.

Stone, Richard, "Search for Sepsis Drugs Goes on Despite Past Failures," Science, Apr. 15, 1994, vol. 264, pp. 365-367.

Urban et al., "NF-$_\kappa$B contacts DNA by a heterodimer of the p50 and p65 subunit," The EMBO Journal, 1991, vol. 10, No. 7, pp. 1817-1825.

Van Zee et al., "Tumor necrosis factor soluble receptors circulate during experimental and clinical inflammation and can protect against excessive tumor necrosis factor α in vitro and in vivo," Proc. Natl. Acad. Sci. USA, Jun. 1992, vol. 89, pp. 4845-4849.

Wasmuth et al., "Patients with acute on chronic liver failure display 'sepsis-like' immune paralysis," Journal of Hepatology, 2005, vol. 42, pp. 195-201.

Zwaveling et al., "High plasma tumor necrosis factor (TNF)-αconcentrations and a sepsis-like syndrome in patients undergoing hyperthermic isolated limb perfusion with recombinant TNF-α, interferon-γ, and melphalan," Crit Care Med, 1996, vol. 24, No. 5, pp. 765-770.

Database EMBL, Sequence information from JP20001116377-A, Oct. 10, 2000 "N-terminus of porcine trypsin", retrieved from EBI Database accession No. AAB03087.

Deitch, "Rodent Models of Intra-Abdominal Infection," *Shock*, 2005, pp. 19-23, vol. 24, Suppl. 1, The Shock Society.

Wheeler et al., NEJM 1999, 340: 207-214.

Attwood Science 2000; 290: 471-473.

Skolnick et al., Trends in Biotech. 2000; 18(1): 34-39.

The Merck Manuals Online Medical Library [online]. Whitehouse Station, NJ: Merck Research Laboratories, 2006-2007. [Retrieved on Nov. 19, 2007]. Retrieved from the Internet: < URL: http://www.merck.Com/mmpe/print/sec06/ch068/ch068a.html>.

Standen et al. N. Engl. J. Med. 2000, 343: 447-448.

Redl et al. World J. Surg. 1996, 20: 487-492.

Mori et al., Archives of Virology 1999, 144: 147-155.

Gencic et al., The Journ. Of Neuroscience 1990, 10: 117-124.

Schenk et al., "TREM-1—Expressing Intestinal Macrophages Crucially Amplify Chronic Inflammation in Experimental Colitis and Inflammatory Bowel Diseases," *The Journ. Of Clinical Investigation*, pp. 1-10 (2005).

Bouchon et al, Journal of Immunology, "Cutting Edge: Inflammatory Responses Can Be Triggered by TERM-1, A Novel Receptor Expressed on Neutrophils and Monocytes", 2000, vol. 164, No. 10, pp. 4991-4995.

Bouchon et al, Nature, "TREM-1 AMPLIFIES Inflammation and is a Crucial Mediator of Septic Shock", 2001, vol. 410, No. , pp. 1103-1107.

J. Phua et al, European Respiratory Journal, "Soluble Triggering Receptor Expressed on Myeloid Cells-1 in Acute Respiratory Infections", 2006, vol. 28, No. , pp. 695-702.

Jun Kuai et al, Rheumatology, "TREM-1 Expression is Increased in the Synovium of Rheumatoid Arthritis Patients and Induces the Expression of Pro-Inflammatory Cytokines", 2009, vol. 48, No. , pp. 1352-1358.

Mirjam Schenk, Journal of Clinical Investigation, "TREM-1—Expressing Intestinal Macrophages Crucially Amplify Chronic Inflammation in Experimental Colitis and Inflammatory Bowel Diseases", 2007, vol. 117, No. , pp. 3097-3106.

Yousuke Murakami et al, Arthritis and Rheumatism, "Intervention of an Inflammation Amplifier, Triggering Receptor Expressed on Myeloid Cells 1, For Treatment of Autoimmune Arthritis", 2009, vol. 60, No. 6, pp. 1615-1623.

Coskun et al., Endocrinology, "Fibroblast Growth Factor 21 Corrects Obesity in Mice", 2008, vol. 149, No. 12, pp. 6018-6027.

Erickson et al., Journal of Lipid Research, "Nonalcoholic Fatty Liver Disease", 2008, vol. -, No. -, pp. S412-S416.

Grundy et al., Circulation, "Definition of Metabolic Syndrome: Report of the National Heart, Lung, and Blood Institute/American Heart Association Conference on Scientific Issues Related to Definition", 2004, vol. 109, No. -, pp. 433-438.

Kharitonenkov et al., Endocrinology, "The Metabolic State of Diabetic Monkeys is Regulated by Fibroblast Growth Factor-21", 2007, vol. 148, No. 2, pp. 774-781.

Kharitonenkov et al., Journal of Clinical Investigation, "FGF-21 as a Novel Metabolic Regulator", 2005, vol. 115, No. -, pp. 1627-1635.

Knudsen, L.B., Journal of Medicinal Chemistry, "Glucagon-Like Peptide-1: The Basis of a New Class of Treatment for Type 2 Diabetes", 2004, vol. 47, No. 17, pp. 4128-4134.

Micanovic et al., Journal of Cellular Physiology, "Different Roles of N- and C- Termini in the Functional Activity of FGF21", 2009, vol. 219, No. 2, pp. 227-234.

(56) References Cited

OTHER PUBLICATIONS

Nauck, M.A et al., Regulatory Peptides, "Glucagon-Like Peptide 1 and Its Derivatives in the Treatment of Diabetes", 2005, vol. 128, No. 2, pp. 135-148.
Xu et al., Diabetes, "Fibroblast Growth Factor 21 Reverses Hepatic Steatosis, Increases Energy Expenditure, and Improves Insulin Sensitivity in Diet-Induced Obese Mice", 2009, vol. 58, No. 1, pp. 250-259.
Yie et al., FEBS Letters, "FGF21 N- and C-Termini Play Different Roles in Receptor Interaction and Activation", 2009, vol. 583, No. 1, pp. 19-24.
Abravaya et al., "Detection of point mutations with a modified ligase chain reaction (Gap-LCR)" Nucleic Acids Res., (1995), 23:675-682.
Alexander et al., "A recombinant human receptor antagonist to interleukin 1 improves survival after lethal endotoxemia in mice", J. Exp. Med., 173:1029-32, 1991.
Ames et al., "Conversion of murine Fabs isolated from a combinatorial phage display library to full length immunoglobulins", J. Immunol. Methods, vol. 184(2), (1995), pp. 177-186.
Amman et al., "Tightly regulated tac promoter vectors useful for the expression of unfused and fused proteins in *Escherichia coli*", Gene, (1988), 69:301-315.
Appelmelk et al., "Use of mucin and hemoglobin in experimental murine Gram-negative bacteremia enhances the immunoprotective action of antibodies reactive with the lipopolysaccharide core region", Antonie Van Leeuwenhoek, (1986), 52:537-42.
Arnon et al., "Monoclonal Antibodies for Immunotargeting of Drugs in Cancer Therapy", in Monoclonal Antibodies and Cancer Therapy, Reisfeld et al., eds., Alan R. Liss, Inc., (1985), pp. 243-256.
Baker et al., "NK cell activation: distinct stimulatory pathways counterbalancing inhibitory signals", Hum Immunol., 61:18-27. 2000.
Bakker et al., "DAP12-deficient mice fail to develop autoimmunity due to impaired antigen priming." Immunity 13:345-53. 2000.
Bakker et al., "Myeloid DAP12-associating lectin (MDL)-1 is a cell surface receptor involved in the activation of myeloid cells, "Proc. Natl. Acad. Sci. USA 96:9792, 1999.
Baldwin et al., "Analysis Results, and Future Prospective of the Therapeutic Use of the Radiolabeled Antibody in Cancer Therapy", in Monoclonal Antibodies for Cancer Detection and Therapy, eds. Adacemic Press, (1985, pp. 303-316.
Banerji et al., "A lymphocyte-specific cellular enhancer is located downstream of the joining region in immunoglobulin heavy chain genes", Cell, (1983), 33:729-740.
Barany,"Genetic disease detection and DNA amplification using cloned thermostable ligase", Proc. Natl. Acad. Sci. USA, (1991), 88:189.
Baldari et al., "A novel leader peptide which allows efficient secretion of a fragment of human interleukin 1b in *Saccharomyces cerevisiae*," EMBO J., (1987), 6:229-234.
Bartel et al., Bio Techniques, (1993), 14:920-924.
Bartel et al., "Isolation of new ribozymes from a large pool of random sequences",Science, (1993), 261:1411-1418.
Bauer et. al., "Activation of NK cells and T cells by NKG2D, a receptor for stress-inducible MICA", Science, 285:727-9, 1999.
Benda et al., "Differentiated Rat Glial Cell Strain in Tissue Culture," Science, (1968), 161:370-371.
Better et al., "*Escherichia coli* secretion of an active chimeric antibody fragment," Science, (1988), 240:1041-1043.
Beutler et al., "Passive immunization against cachectin/tumor necrosis factor protects mice from lethal effect of endotoxin", Science, 229:869-71, 1985.
Beutler, B., "Endotoxin, toll-like receptor 4, and the afferent limb of innate immunity", Curr. Opin. Microbiol., vol. 3 (1), (2000), pp. 23-28.
Boesen et al., "Circumvention of chemotherapy-induced myelosuppression by transfer of the mdr1 gene," Biotherapy, (1994), 6:291-302.
Bolin et al., "Survey of cell lines in the American Type Culture Collection for bovine viral diarrhea virus", J. Virol. Methods, (1994), 48: 211-221.

Bone, "The pathogenesis of sepsis," Ann. Intern. Med. 115:457-69, 1991.
Bordelon-Riser et al., "Necessity for two human chromosomes for human chorionic gonadotropin production in human-mouse hybrids", Somatic Cell Genetics, (1979), 5:597-613.
Bork & Bairoch, "Go hunting in sequence databases but watch out for the traps", Trends in Genetics, (1996)vol. 12(10), pp. 425-427.
Bork, "Powers and Pitfalls in Sequence Analysis: The 70% Hurdle", Genome Research, (2000), 10:398-400.
Bout et al., "Lung Gene Therapy: In Vivo Adenovirus-Mediated Gene Transfer to Rhesus Monkey Airway Epithelium", Human Gene Therapy, (1994), 5:3-10.
Bradley, Teratocarcinomas and Embryonic Stem Cells: A Practical Approach, Robertson, ed., IRL, Oxford, (1987), pp. 113-152.
Bradley, "Modifying the mammalian genome by gene targeting", Current Opinion in Bio Technology, (1991), 2:823-829.
Brenner, "Errors in genome annotation", Trends in Genetics, vol. 15(4), (Apr. 1999), pp. 132-133.
Brinkman et al., "Phage display of disulfide-stabilized Fv fragments", J. Immunol. Methods, (1995), 182:41-50.
Burton et al., "Human Antibodies from Combinatorial Libraries", Advances in Immunology, (1994), 57:191-280.
Byrne & Ruddle, "Multiplex gene regulation: a two-tiered approach to transgene regulation in transgenic mice", Proc. Natl. Acad. Sci. USA, (1989), 86:5473-5477.
Calame et al., "Transcriptional controlling elements in the immunoglobulin and T cell receptor loci", Adv. Immunol., vol. 43, (1988), pp. 235-275.
Calandra et al., J. Immunol., (2000), 145:3762-6.
Calandra et al., "Protection from septic shock by neutralization of macrophage migration inhibitory factor," Nat. Med., 6:164-70, 2000.
Campes & Tilghman, "Postnatal repression of the alpha-fetoprotein gene is enhancer independent", Genes Dev., (1989), 3:537-546.
Cantoni et al., "NKp44, a triggering receptor involved in tumor cell lysis by activated human natural killer cells, is a novel member of the immunoglobulin superfamily," J. Exp. Med. 189(5), (1999), pp. 787-796.
Carrell et al., "A Novel Procedure for the Synthesis of Libraries Containing Small Organic Molecules" Angew. Chem. Int. Ed. Engl., (1994), 33:2059 & 2061.
Cella et al., "Anovel inhibitory receptor (ILT3) expressed on monocytes, macrophages, and dendritic cells involved in antigen processing", J. Exp. Med., vol. 185(10), (1997), pp. 1743-1751.
Chen et al., "Gene therapy for brain tumors: regression of experimental gliomas by adenovirus-mediated gene transfer in vivo.", Proc. Natl. Acad. Sci. USA, (1994), 91:3054-3057.
Cho et al., "An unnatural biopolymer ", Science, (1993), 261:1303.
Chomel et al., "Bartonella henselae Prevalence in Domestic Cats in California: Risk Factors and Association between Bacteremia and Antibody Titers.", Journal of Clinical Microbiology, vol. 33(9), (Sep. 1995), pp. 2445-2450.
Cohen et al., "[42] Receptor-mediated transport of DNA into eukaryotic cells", Meth. Enzymol., (1993), 217:618-644.
Clowes et al., "Long-term biological response of injured rat carotid artery seeded with smooth muscle cells expressing retrovirally introduced human genes.", J. Clin. Invest., (1994), 93:644-651.
Cohen et al., "Emerging Technologies for Sequencing Antisense Oligonucleotides: Capillary Electrophoresis and Mass Spectrometry," Adv. Chromatogr., (1996), 36:127-162.
Colberre-Garapin et al., "A new dominant hybrid selective marker for higher eukaryotic cells", J. Mol. Biol., (1981) 150:1.
Cotton et al., "Reactivity of cytosine and thymine in single-base-pair mismatches with hydroxylamine and osmium tetroxide and its application to the study of mutations", Proc. Natl. Acad. Sci. USA, (1988), 85:4397.
Cotton, "Current methods of mutation detection", Mutat. Res., (1993), 285:125-144.
Cox et al., "IL-10 enhances resolution of pulmonary inflammation in vivo by promoting apoptosis of neutrophils," Am. J. Physiol. Lung Cell Mol Physiol., (1996), 271:L566-L571.
Cronin et al., "Cystic fibrosis mutation detection by hybridization to light-generated DNA probe arrays", Human Mutation, (1996), 7:244-255.

(56) References Cited

OTHER PUBLICATIONS

Cruikshank et al., J. Acquired Immune Deficiency Syndromes and Human Retrovirology, (1997) 14:193.
Cull et al., "Screening for receptor ligands using large libraries of peptides linked to the C terminus of the lac repressor.", Proc. Natl. Acad. Sci. USA, (1992), 89:1865-1869.
Cwirla et al., "Peptides on phage: a vast library of peptides for identifying ligands.", Proc. Natl. Acad. Sci. USA, (1990), 87:6378-6382.
Daws et al., "Cloning and Characterization of a Novel Mouse Myeloid DAP12-Associated Receptor Family," Eur. J. Immunol. 2001, 31:783-791.
Devlin, "Random peptide libraries: a source of specific protein binding molecules",Science, (1990), 249:404-406.
Dewitt et al., "Diversomers: an approach to nonpeptide, nonoligomeric chemical diversity", Proc. Natl. Acad. Sci. USA, (1993), 90:6909.
Dietrich et al., "Signal-regulatory protein β1 is a DAP12-associated activation receptor expressed in myeloid cells." J. Immunol. 164:9, 2000.
Doerks et al., "Protein annotation: detective work for function prediction", Trends in Genetics, vol. 14(6), (Jun. 1998), pp. 248-250.
Downey et al., "Intracellular signaling in neutropohil priming and activation," Semin Cell Bio. 6:345-356, 1995.
Echtenacher et al. "Critical protective role of mast cells in a model of acute septic peritonitis", Nature, (1996), 381:75-7.
Edlund et al., "Cell-specific expression of the rat insulin gene: evidence for role of two distinct 5' flanking elements", Science, (1985) 230:912-916.
Erb et al., "Recursive deconvolution of combinatorial chemical libraries",Proc. Natl. Acad. Sci. USA, (1994), 91:11422.
Facchetti et al., "Suppurative Granulomatous Lymphadenitis; Immunohistochemical Evidence for a B-cell Associated Granuloma," Am. J. Surg. Pathol., (1992), 16: 955-61.
Felici, "Selection of antibody ligands from a large library of oligopeptides expressed on a multivalent exposition vector", J. Mol. Biol., (1991), 222:301-310.
Fell et al., "Genetic construction and characterization of a fusion protein consisting of a chimeric F(ab') with specificity for carcinomas and human IL-2.", J. Immunol., (1991), 146:2446-2452.
Finn et al., Synthesis and Properties of DNA-PNA Chimeric Oligomers Nucleic Acids Res., (1996), 24(17): 3357-63.
Fodor, "Multiplexed biochemical assays with biological chips", Nature, (1993), 364:555-556.
Forster et al., "CCR7 coordinates the primary immune response by establishing functional microenvironments in secondary lymphoid organ," Cell 99:23-33, 1999.
Gallop et al., "Applications of Combinatorial Technologies to Drug Discovery. 1. Background and Peptide Combinatorial Libraries", J. Med. Chem., (1994), 37:1233.
Gasparini et al., "Restriction site generating-polymerase chain reaction (RG-PCR) for the probeless detection of hidden genetic variation: application to the study of some common cystic fibrosis mutations", Mol. Cell Probes, (1992), 6:1.
Gaultier et al.,"a-DNA IV: a-anomeric and b-anomeric tetrathymidylates covalently linked to intercalating oxazolopyridocarbazole. Synthesis, physicochemical properties and poly (rA) binding" Nucleic Acids Res., (1987), 15:6625-6641.
Gelrud et al., "Interaction of Tumor Necrosis Factor-a and Granulocyte Colony-Stimulation Factor on Neutrophil Apoptosis, Receptor Expression, and Bactericidal Function", Proc. Assoc. Am. Physicians, (1996), 108:455-456.
Gentz et al., "Bioassay for trans-activation using purified human immunodeficiency virus tat-encoded protein: trans-activation requires mRNA synthesis", Proc. Natl. Acad. Sci. USA, (1989), 86:821-824.
Gibbs et al., "Detection of single DNA base differences by competitive oligonucleotide priming" Nucleic Acids Res., (1989), 17:2437-2448.
Gillies et al., "High-level expression of chimeric antibodies using adapted cDNA variable region cassettes", J. Immunol. Methods, (1989), 125:191-202.
Gillies et al., "Antibody-targeted interleukin 2 stimulates T-cell killing of autologous tumor cells", Proc. Natl. Acad. Sci. USA., (1992), 89:1428-1432.
Glauser et al., "Septic shock: pathogenesis," Lancet 338:732-6, 1991.
Goldspiel et al., "Human Gene Therapy," Clinical Pharmacy, (1993), 12:488-505.
Gon et al. Microbiol. Immunol., (1996) 40:463-465.
Griffin et al., "DNA sequencing", Appl. Biochem. Biotechnol., (1993), 38:147-159.
Grossman & Wilson, "Retroviruses: delivery vehicle to the liver", Curr. Opin. In Genetics and Devel., (1993), 3:110-114.
Guatelli et al., "Isothermal, in vitro amplification of nucleic acids by a multienzyme reaction modeled after retroviral replication", Proc. Natl. Acad. Sci. USA, (1990), 87:1874-1878.
Haapala et al., "Isolation from cats of an endogenous type C virus with a novel envelope glycoprotein.", J. Virol., (1985), 53:827-833.
Hammerling et al., Moloclonal Antibodies and T-Cell Hybridomas, Elsevier, New York, (1981) pp. 563-681.
Haselhoff et al., "Simple RNA enzymes with new and highly specific endoribonuclease activities", Nature, (1988), 334: 585-591.
Hayashi, "PCR-SSCP: A method for detection of mutations", Genet. Anal. Tech. Appl., (1992), 9:73-79.
He et al., "Expression of O6-Methylguanine-DNA Methyltransferase in Six Human Medulloblastoma Cell Lines", Cancer Res., (1992), 52:1144-1148.
Hebert et al., "Sequential morphologic events during apoptosis of human neutrophils. Modulation by lipoxygenase-derived eicosanoids.", J. Immunol., (1996), 157:3105-3115.
Helene, "The anti-gene strategy: control of gene expression by triplex-forming-oligonucleotides" Anticancer Drug Des., (1991), 6(6):569-84.
Helene, "Control of Gene Expression by Triple Helix-Forming Oligonucleotides. The Antigene Strategy", Ann. N.Y. Acad. Sci., (1992), 660:27-36.
Hellstrom et al., "Antibodies for Drug Delivery" in Controlled Drug Delivery, 2nd edition, Robinson et al., eds., Marcel Dekker, Inc., (1987), pp. 623-653.
Hoffman et al., "Phylogenetic perspectives in innate immunity", Science, vol. 284(5418), 1999, pp. 1313-1318.
Houghten, Bio Techniques, (1992), 13:412-421.
Hsu et al., "Detection of DNA point mutations with DNA mismatch repair enzymes", Carcinogenesis, (1994), 15:1657-1662.
Huston et al., "Protein engineering of single-chain Fv analogs and fusion proteins", Methods in Enzymology, (1991), 203-46-88.
Hyrup et al., "Peptide Nucleic Acids (PNA): Synthesis, properties and potential applications", Bioorganic & Medicinal Chemistry, 1996, 4(1): 5-23.
Inoue et al., "Synthesis and hybridization studies on two complementary nona(2'-O-methyl)ribonucleotides" Nucleic Acids Res., (1987), 15: 6131-6148.
Inoue et al., "Sequence-dependent hydrolysis of RNA using modified oligonucleotide splints and RNase H", FEBS Lett., (1987), 215: 327-330.
Iwabuchi et al., Oncogene, (1993), 8: 1693-1696.
Jespers et al., Bio Technology, (1988), 12: 899-903.
Jobling & Holmes, "Analysis of structure and function of the B Subunit of cholera toxin by the use of site-directd mutagenesis", Molecular Microbiology, vol. 5(7), pp. 1755-1767.
Katsuura et al., "CD48 expression on leukocytes in infectious diseases: flow cytometric analysis of surface antigen", Acta Paediatr Jpn., vol. 40(6), 1998, pp. 580-585.
Kaufman et al., EMBO J., (1987), 6: 187-195.
Keen et al., "Rapid detection of single base mismatches as heteroduplexes on Hydrolink gels", Trends Genet., (1991), 7:5.
Kessel & Gruss, "Murine developmental control genes", Science, (1990), 249: 374-379.
Kettleborough et al., "Isolation of tumor cell-specific single-chain Fv from immunized mice using phage-antibody libraries and the reconstruction of whole antibodies from these antibody fragments", Eur. J. Immunol., vol. 24(4), 1994, pp. 852-958.

(56) References Cited

OTHER PUBLICATIONS

Kiem et al., Retrovirus-Mediated Gene Transduction into Canine Peripheral Blood Repopulating Cells, Blood, (1994), 83: 1467-1473.
Knappik et al., Biotechniques, (1994), 17(4): 754-761.
Kohler, "Immunoglobulin chain loss in hybridoma lines", Proc. Natl. Acad.Sci. USA, (1980), 77: (4) 2197.
Koller & Smithies, "Inactivating the beta 2-microglobulin locus in mouse embryonic stem cells by homologous recombination", Proc. Natl. Acad. Sci. USA (1989), 86: 8932-8935.
Kozal et al., "Extensive polymorphisms observed in HIV?1 Glade B protease gene using high?density oligonucleotide arrays ", Nature Medicine, (1996), 2: 753-759.
Kozarsky & Wilson, "Gene therapy: adenovirus vectors", Current Opinion in Genetics and Development, (1993), 3: 499-503.
Krol et al., "Modulation of Eukaryotic Gene Expression by Complementary RNA or DNA Sequences" Bio/Techniques, (1988), 6: 958-976.
Kruse et al., "Characterization of a continuous human glioma cell line DBTRG-05MG: growth kinetics, karyotype, receptor expression, and tumor suppressor gene analyses", In Vitro Cell. Dev. Biol., (1992), 28A: 609-614.
Kubagawa et al., "Biochemical nature and cellular distribution of the paired immunoglobulin-like receptors, PIR-B." J. Exp. Med 189:309, 1999.
Kunkel et al., "Rapid and efficient site-specific mutagenesis without phenotypic selection", Methods Enzymol., (1987), 154: 367-82.
Kurjan & Herskowitz, "Structure of a yeast pheromone gene (MF?): A putative ?-factor precursor contains four tandem copies of mature ?-factor", Cell (1982), 30: 933-943.
Kwoh et al., "Transcription-based amplification system and detection of amplified human immunodeficiency virus type 1 with a bead-based sandwich hybridization format", Proc. Natl. Acad. Sci. USA, (1989), 86: 1173-1177.
Lakso et. al., "Targeted oncogene activation by site-specific recombination in transgenic mice", Proc. Natl. Acad. Sci. USA, (1992) 89: 6232-6236.
Lam, Nature, "A new type of synthetic peptide library for identifying ligand-binding activity", (1991), 354: 82-84.
Lam, "Mini-review. Application of combinatorial library methods in cancer research and drug discovery", Anticancer Drug Des., (1997), 12: 145.
Landegran et al., "A ligase-mediated gene detection technique", Science, (1988), 241: 1077-1080.
Lane et al., "CD40 ligand-independent B cell activation revealed by CD40 ligand-deficient T cell clones: evidence for distinct activation requirements for antibody formation and B cell proliferation", Eur. J. Immunol., (1995), 6: 1788.
Lanier et al., "NK cell receptors," Annu. Rev. Immunol., 16: 359 (1998).
Lanier, LL, "Immunoreceptor DAP12 bearing a tyrosine-based activation motif is involved in activating NK cells", Nature, vol. 391 (6668), (1998), pp. 703-707.
Lemaitre et al., "Specific antiviral activity of a poly(L-lysine)-conjugated oligodeoxyribonucleotide sequence complementary to vesicular stomatitis virus N protein mRNA initiation site", Proc. Natl. Acad. Sci. USA, (1987), 84: 648-652.
Letsinger et al., "Cholesteryl-conjugated oligonucleotides: synthesis, properties, and activity as inhibitors of replication of human immunodeficiency virus in cell culture", Proc. Natl. Acad. Sci. USA. (1989), 86: 6553-6556.
Li et al., "Targeted mutation of the DNA methyltransferase gene results in embryonic lethality," Cell, (1992), 69: 915.
Lizardi et al., "Exponential amplification of recombinant-RNA hybridization probes," Nature Biotechnology, (1988), 6: 1197-1202.
Loeffler & Behr, "Gene transfer into primary and established mammalian cell lines with lipopolyamine-coated DNA," Meth. Enzymol., (1993), 217: 599-618.
Lonberg et al., "Human antibodies from transgenic mice", Int. Rev. Immunol., vol. 13(1), (1995) pp. 65-93.
Lowy et al., "Isolation of transforming DNA: Cloning the hamster aprt gene," Cell, (1980), 22: 817.
Lucklow & Summers, "High level expression of nonfused foreign genes with Autographa californica nuclear polyhedrosis virus expression vectors," Virology, (1989), 170: 31-39.
Madura et al., "N-recognin/Ubc2 interactions in the N-end rule pathway," J. Biol. Chem., (1993), 17: 5973-88.
Mag et al., "Synthesis and selective cleavage of oligodeoxyribonucleotldes containing non-chiral intemucieotlde phosphoramidate linkages," Nucleic Acids Res., (1989), 17: 5973-88.
Maher, "DNA Triple-Helix Formation: An Approach to Artificial Gene Repressors?," Bioassays, (1992), 14(12): 807-15.
Malaviya et al., "Mast cell modulation of neutorphil influx and bacterial clearance at sites of infection thrugh TNF-alpha", Nature, 381, (1996), pp. 77-80.
Mastrangeli et al., "Diversity of airway epithelial cell targets for in vivo recombinant adenovirus-mediated gene transfer," J. Clin. Invest., (1993), 91: 225-234.
Maxam & Gilbert, "A new method for sequencing DNA," Proc. Natl. Acad. Sci. USA, (1977), 74: 560.
McNamara et al., "Interleukin-1 receptor antibody (IL-1rab) protection and treatment against lethal endotoxemia in mice", J. Surg. Res., 54, (1993), 316-21.
Michael et al., Biotechniques, (1994), 16(3): 410-412.
Miller et al., "Use of retroviral vectors for gene transfer and expression," Meth. Enzymol., (1993), 217: 581-599.
Morgan & Anderson, "Human Gene Therapy," Ann. Rev. Biochem., (1993), 62: 191-217.
Morrison et al., "Endotoxins and disease mechanisms." Annu. Rev. Med. 38: 417-32, 1987.
Morrison, "Transfectomas provide novel chimeric antibodies," Science, (1985), 229: 1202.
Mulligan, "The basic science of gene therapy," Science, (1993), 260: 926-932.
Mulligan & Berg, "Selection for animal cells that express the *Escherichia coli* gene coding for xanthine-guanine phosphoribosyltransferase," Proc. Natl. Acad. Sci. USA, (1981), 78: 2072.
Mullinax et al., Bio Techniques, (1992), 12(6): 864-869.
Myers et al., "Detection of single base substitutions in total genomic DNA," Nature, (1985), 313: 495.
Myers et al., "Detection of single base substitutions by ribonuclease cleavage at mismatches in RNA:DNA duplexes," Science, (1985), 230: 1242.
Nakajima et al., "Human myeloid cells express and activating ILT receptor (ILTI) that associates with Fc receptor y-chain," J. Immunol. 162: 5. (1999), pp. 5-8.
Nakajima et al., "2B4: an NK cell activating receptor with unique specificity and signal transduction mechanism", Humm Immunol., vol. 61, (2000), pp. 39-43.
Nakazawa et al., "UV and skin cancer: specific p53 gene mutation in normal skin as a biologically relevant exposure measurement," Proc Natl. Acad. Sci. USA, (1994), 91: 360-364.
Naramura et al., "Mechanisms of cellular cytotoxicity mediated by a recombinant antibody-IL2 fusion protein against human melanoma cells," Immunol. Lett., (1994), 39: 91-99.
Nederman et al., "An in vitro bioassay for quantitation of human interferons by measurements of antiproliferative activity on a continuous human lymphoma cell line." Biologicals, vol. 18(1), (1990), pp. 29-34.
Ngo et al., "The Protein Folding Problem and Tertiary Structure Prediction, Chapter 14: Computational Complexity Protein Structure Prediction, and the Levinthal Paradox", (Mar. 2, 1995), pp. 492-495.
Nicoletti et al., "A rapid and simple method for measuring thymocyte apoptosis by propidium iodide staining and flow cytometry," J. Immunol. Methods, (1991), 139: 271-279.
O'Gorman et al., "Recombinase-mediated gene activation and site-specific integration in mammalian cells," Science, (1991), 251: 1351-1355.

(56) References Cited

OTHER PUBLICATIONS

O'Hare et al., "Transformation of mouse fibroblasts to methotrexate resistance by a recombinant plasmid expressing a prokaryotic dihydrofolate reductase," Proc. Natl. Acad. Sci. USA, (1981), 78: 1527.
Ohlsson et al., "Interleukin-1 receptor antagonist reduces mortality from endotoxin shock", Nature, vol. 348, (1990), pp. 550-552.
Ol et al., "Chimeric Antibodies," Bio Techniques, (1986), 4: 214-221.
Oishi et al., "Inhibition of Neutrophil Apoptosis by Antioxidants in Culture Medium," Scand. J. Immunol., (1997), 45: 21-27.
Oliveira et al., "Fungal infections in marrow transplant recipients under antifungal prophylaxis with fluconazole", Brazilian Journal of Medical and Biological Research, vol. 35(7), (Jul. 2002), pp. 789-798.
Olopade et al., "Molecular Analysis of Deletions of the Short Arm of Chromosome 9 in Human Gliomas," Cancer Res., (1992), 52: 2523-2529.
Orita et al., "Detection of polymorphisms of human DNA by gel electrophoresis as single-strand conformation polymorphisms," Proc. Natl. Acad. Sci. USA, (1989), 86: 2766.
Owerbach et al., "Genetics of the large, external, transformation-sensitive (LETS) protein: assignment of a gene coding for expression of LETS to human chromosome 8," Proc. Natl. Acad. Sci. USA, (1978), 75: 5640-5644.
Padlan, "A possible procedure for reducing the immunogenicity of antibody variable domains while preserving their ligand-binding properties," Molecular Immunology, (1991), 28(4/5): 489-498.
Pajunen et al. "Assignment of the gene coding for both the beta-subunit of prolyl 4-hydroxylase and the enzyme disulfide isomerase to human chromosome region 17p11-qter," Cytogenet. Cell Genet., (1988), 47: 37-41 (Abstract).
Perry-O'Keefe et al., "Peptide nucleic acid pre-gel hybridization: An alternative to Southern?hybridization," Proc. Natl. Acad. Sci. USA, (1996), 93: 14670-675.
Persic et al., "An integrated vector system for the eukaryotic expression of antibodies or their fragments after selection from phage display libraries", Gene, vol. 187(1), (1997), pp. 9-18.
Peschon et al., "TNF receptor-deficient mice reveal divergent roles for p55 and p75 in several models of inflammation", J. Immunol., vol. 160, (1998), pp. 943-952.
Petersen et al., A PNA-DNA linker synthesis of N-((4,4?-dimethoxytrityloxy)ethyl)-N-(thymin-1-ylacetyl)glycine, Bioorganic Med. Chem. Lett., (1995), 5: 1119-1124.
Pfeffer et al., "Mice deficient for the 55 kd tumor necrosis factor receptor are resistant to endotoxic shock, yet succumb to L. monocytogenes infection", Cell, vol. 73, (1993) pp. 457-467.
Pinkert et al., "An albumin enhancer located 10 kb upstream functions along with its promoter to direct efficient, liver-specific expression in transgenic mice," Genes Dev., (1987), 1: 268-277.
Pittelkow & Scott, "New Techniques for the In Vitro Culture of Human Skin Keratinocytes and Perspectives on Their Use for Grafting of Patients With Extensive Burns," Mayo Clinic Proc., (1986), 61: 771.
Prosser, "Detecting single-base mutations," Tibtech, (1993), 11: 238-246.
Proudfoot, "Transcriptional interference and termination between duplicated globin gene constructs suggests a novel mechanism for gene regulation," Nature, (1986), 322: 562.
Queen & Baltimore, "Immunoglobulin gene transcription is activated by downstream sequence elements," Cell, (1983), 33: 741-748.
Radany et al., "Directed establishment of rat brain cell lines with the phenotypic characteristics of type 1 astrocytes," Proc. Natl. Acad. Sci. USA, (1992) 89: 6467-6471.
Rheinwald, "Chapter 15 Serial Cultivation of Normal Human Epidermal Keratinocytes," Meth. Cell Bio., (1980), 21A: 229.
Riechmann et al., "Reshaping human antibodies for therapy," Nature, (1988), 332: 323.
Roguska et al., "Humanization of murine monoclonal antibodies through variable domain resurfacing," Proc. Natl. Acad. Sci. USA, (1994), 91: 969-973.

Rosenbaum & Reissner, "Temperature-gradient gel electrophoresis: Thermodynamic analysis of nucleic acids and proteins in purified form and in cellular extracts," Biophys. Chem., (1987), 26:235-246.
Rosenberg et al., "Inflammation," In Fundamental Immunology, 4th Ed. W. E. Paul, ed., p. 1051, 1999.
Rosenfeld et al., "Adenovirus-mediated transfer of a recombinant alpha 1-antitrypsin gene to the lung epithelium in vivo," Science, (1991), 252: 431-434.
Rosenfeld et al., "In vivo transfer of the human cystic fibrosis transmembrane conductance regulator gene to the airway epithelium," Cell, (1992), 68:143-155.
Rothe et al., "Mice lacking the tumour necrosis factor rector receptor 1 are resistant to TNF-mediated toxicity but highly susceptible to infection by Listeria monocytogenes" Nature, vol. 364, (1993), pp. 798-802.
Saiki et al., "Analysis of enzymatically amplified b-globin and HLA-DQa DNA with allele-specific oligonucleotide probes," Nature, (1986), 324: 163.
Saiki et al., "Genetic analysis of amplified DNA with immobilized sequence-specific oligonucleotide probes," Proc. Natl. Acad. Sci. USA, (1989), 86:6230.
Saleeba et al., "Chemical cleavage of mismatch to detect mutations," Methods Enzymol., (1992), 217: 286-295.
Sallusto et al., "Efficient peresentation of soluble antigen by cultured human dendritic cells is maintained by granulocyte/macrophage colony-stimulation factor plus interleukin 4 and downregulated by tumor necrosis factor alpha", J. Exp. Med., 1994, vol. 179(4), pp. 1109-1118.
Salmons & Gunzberg, "Targeting of Retroviral Vectors for Gene Therapy," Human Gene Therapy, (1993), 4: 129-141.
Sambrook et al., Molecular Cloning, A Laboratory Manual, 2nd Edition, Cold Spring Harbor Laboratory, Cold Spring Harbor, NY, (1990), Chapters 16 & 17.
Sanger, "DNA sequencing with chain-terminating inhibitors," Proc. Natl. Acad. Sci. USA, (1977), 74: 5463.
Santerre et al., "Expression of prokaryotic genes for hygromycin B and G418 resistance as dominant-selection markers in mouse L cells," Gene, (1984), 30: 147.
Sawai et al., "Direct Production of the Fab Fragment Derived From the Sperm Immobillizing Antibody Using Polymerase Chain Reaction and cDNA Expression Vectors," AJRI, (1995), 34:26-34.
Schultz et al., "Expression and secretion in yeast of a 400-kda envelope glycoprotein derived from epstein-barr virus," Gene, (1987), 54: 113-123.
Scott & Smith, "Searching for peptide ligands with an epitope library," Science, (1990), 249: 386-390.
Seed, "An LFA-3 cDNA encodes a phospholipid-linked membrane protein homologous to its receptor CD2," Nature, (1987), 329: 840.
Shu et al., "Secretion of a single-gene-encoded immunoglobulin from myeloma cells", Proc. Natl. Acad. Sci. USA, vol. 90(17), (1993), pp. 7995-7999.
Skerra et al., "Assembly of a functional immunoglobulin Fv fragment in *Escherichia coli*", Science, vol. 240(4855), (1988), pp. 1038-1041.
Smith et al., "Production of human beta interferon in insect cells infected with a baculovirus expression vector," Mol. Cell Biol., (1983), 3: 2156-2165.
Smith & Johnson, "Single-step purification of polypeptides expressed in *Escherichia coli* as fusions with glutathione S-transferase," Gene, (1988), 67: 31-40.
Smith & Zhang, "The challenges of genome sequence annotation or 'The devil is in the details'", Nature Biotechnology, vol. 15 (Nov. 1997), pp. 1222-1223.
Springer et al., "Traffic signals for lymphocyte recirculation and leukocyte emigration: The multistep paradigm," Cell, 76: 301, 1994.
Stemple & Anderson, "Isolation of a stem cell for neurons and glia from the mammalian neural crest," Cell, (1992), 71:973-985.
Studnicka et al., "Human-engineered monoclonal antibodies retain full specific binding activity by preserving non-CDR complementarity-modulating residues," Protein Engineering, (1994), 7(6):805-814.

(56) References Cited

OTHER PUBLICATIONS

Sugimoto et al., "Determination of cell surface membrane antigens common to both human neuroblastoma and leukemia-lymphoma cell lines by a panel of 38 monoclonal antibodies", J. Natl. Cancer Inst., vol. 73(1), (1984), pp. 51-57.
Szybalska & Szybalski, "Genetics of human cell lines, IV. DNA-mediated heritable transformation of a biochemical trait," Proc. Natl. Acad. Sci. USA, (1962), 48: 2026.
Thomas & Capecchi, "Site-directed mutagenesis by gene targeting in mouse embryo-derived stem cells," Cell, (1987), 51: 503.
Thorpe et al., "The Preparation and Cytotoxic Properties of Antibody-Toxin Conjugates," Immunol. Rev., (1982), 62: 119-58.
Thorpe, Antibody Carriers of Cytotoxic Agents in Cencer Therapy: A Review, in Monoclonal Antibodies 84: Biological and Clinical Applications, Pinchera et al., eds., (1985), pp. 475-506.
Tolstoshev, "Gene Therapy, Concepts, Current Trials and Future Directions," Ann. Rev. Pharmacol. Toxicol., (1993), 32: 573-596.
Tomasello et al., "Combined natural killer cell and dendritic cell functional deficiency in KASRAP/DAP12 loss-of-function mutant mice", Immunity 13: 355-64, 2000.
Tomic et al., "A rapid and simple method for introducing specific mutations into any position of DNA leaving all other positions unaltered," Nucleic Acids Res., (1990), 18(6): 1656.
Tracey et al., "Shock and tissue injury induced by recombinant human cachectin." Science 234-470-4 1986.
Traunecker et al., "Myeloma based expression system for production of large mammalian proteins," Trends Biotechnol., vol. 9, (1991), pp. 109-113.
Trowbridge et al., "Establishment and characterization of ferret cells in culture," In Vitro, (1982), 18: 952-960.
Ulevitch et al., "Recognition of Gram-negative bacteria and endotoxin by the innate immune system," Curr. Opin. Immunol, vol. 11, (1999), pp. 19-22.
Upender et al., "Megaprimer Method for In Vitro Mutagenesis Using Parallel Templates," Biotechniques, (1995), 18 (1): 29-30, 32.
Van Keuren et al., "Regional assignment of human liver-type 6-phosphofructokinase to chromosome 21q22.3 by using somatic cell hybrids and a monoclonal anti-L antibody," Hum. Genet., (1986), 74:34-40.
Wada et al., "Codon usage tabulated from the GenBank genetic sequence data," Nucleic Acid Res., (1992), 20: 2111-2118.
Wakayama et al., "Mice cloned from embryonic stem cells," Proc. Natl. Acad. Sci. USA, (1999), 96: 14984-14989.
Walsh et al., "Gene Therapy for Human Hemoglobinopathies," Proc. Soc. Exp. Biol. Med., (1993), 204: 289-300.
Wang et al., "A packaging cell line for propagation of recombinant adenovirus vectors containing two lethal gene-region deletions," Gene Therapy, (1995), 2: 775-783.
Wang et al., "HMG-1 as a late mediator of endotoxin lethality in mice", Science, vol. 285, (1999), pp. 248-251.
Weintraub et al., "Anti-sense RNA as a molecular tool for genetic analysis," Reviews—Trends in Genetics, (1986), vol. 1(1), pp. 22-25.
Wells, "Additivity of Mutational Effects in Proteins", Biochemistry, vol. 29(37), (Sep. 18, 1990), pp. 8509-8517.
Wigler et al., "Transfer of purified herpes virus thymidine kinase gene to cultured mouse cells," Cell, (1977), 11: 223.
Wigler et al., "Transformation of mammalian cells with an amplifiable dominant-acting gene," Natl. Acad. Sci. USA, (1980), 77: 3567.
Wilmut et al., "Viable offspring derived from fetal and adult mammalian cells," Nature, (1997), 385: 810-813.
Wilson et al., "The structure of an antigenic determinant in a protein", Cell, vol. 37(3), (1984), pp. 767-778.
Winoto & Baltimore, "A novel, inducible and T cell-specific enhancer located a the 3' end of the T cell receptor a locus," EMBO J., (1989), 8: 729-733.
Wu & Wu, "Receptor-mediated in vitro gene transformation by a soluble DNA carrier system," J. Biol. Chem., (1987), 262: 4429-4432.
Wu & Wu, "Delivery systems for gene therapy," Biotherapy, (1991), 3: 87-95.
Yamashita, "Inhibitory and stimulatory functions of paired Ig-like receptor (PIR family in RBL-2H3 Cells," J. Immunol. 161, (1998), pp. 4042-4047.
Zervos et al., "Mxi1, a protein that specifically interacts with Max to bind Myc-Max recognition sites," Cell, (1993), 72: 223-232.
Zijlstra et al., "Germ-line transmission of a disrupted b2-microglobulin gene produced by homologous recombination in embryonic stem cells," Nature, (1989), 342: 435-438.
Zon, "Oligonucleotide Analogues as Potential Chemotherapeutic Agents," Pharm. Res., (1988), 5: 539-549.
Zuckermann et al., "Discovery of Nanomolar Ligands for 7-Transmembrane G-Protein-Coupled Receptors from a Diverse N-(Substituted)glycine Peptoid Library," J. Med.Chem., (1994), 37: 2678.
Basic Methods in Molecular Biology, Elsevier Science Publishing Co., New York, (1986), pp. 75-78 and 84-87.
Current Protocols in Molecular Biology, John Wiley & Sons, New York, (1989), Supp 24, 6.3.1-6.3.6.
NCBI Sequence Viewer Accession No. D78812 (Jul. 20, 2006).
NCBI Sequence Viewer Accession No. AI337247 (Mar. 18, 1999).
NCBI Sequence Viewer Accession No. AW139572 (Oct. 30, 1999).
NCBI Sequence Viewer Accession No. AW274906 (Jan. 3, 2000).
NCBI Sequence Viewer Accession No. AW139573 (Oct. 30, 1999).
NCBI Sequence Viewer Accession No. AW394041 (Feb. 4, 2000).
NCBI Sequence Viewer Accession No. AI621023 (Dec. 14, 1999).
NCBI Sequence Viewer Accession No. AI186456 (Oct. 28, 1998).
NCBI Sequence Viewer Accession No. AI968134 (Aug. 25, 1999).
NCBI Sequence Viewer Accession No. AI394092 (Mar. 30, 1999).
NCBI Sequence Viewer Accession No. AI681036 (Dec. 16, 1999).
NCBI Sequence Viewer Accession No. AI962750 (Mar. 8, 2000).
NCBI Sequence Viewer Accession No. AA494171 (Aug. 19, 1997).
NCBI Sequence Viewer Accession No. AA099288 (May 11, 1997).
NCBI Sequence Viewer Accession No. AW139363 (Oct. 30, 1999).
NCBI Sequence Viewer Accession No. AW135801 (Oct. 29, 1999).
NCBI Sequence Viewer Accession No. AA101983 (May 11, 1997).
NCBI Sequence Viewer Accession No. AF196329 (May 24, 2000).
NCBI Sequence Viewer Accession No. AF213457 (May 23, 2000).
NCBI Sequence Viewer Accession No. N41388 (Jan. 24, 1996).
Sharif and Knapp, "From expression to signaling: Roles of TREM-1 and TREM-2 in innate immunity and bacterial infection," Immunobiology, vol. 213, No. 9-10, pp. 701-713 (2008).
Turnbull et al., "Cutting Edge: TREM-2 Attenuates Macrophage Activation," J. Immunol., vol. 177, pp. 3520-3524 (2006).
Adrie et al., "Postresuscitation disease after cardiac arrest: a sepsis-like syndrom?", Current Opinion in Critical Care, Jun. 2004, vol. 10, pp. 208-212.
Begum et al., "*Mycobacterium bovis* BCG Cell Wall-Specific Differentially Expressed Genes Identified by Differential Display and cDNA Subtraction in Human Macrophages," Infection and Immunity, Feb. 2004, pp. 937-948.
Beleharski et al., "A Role for Triggering Receptor Expressed on Myeloid Cells-1 in Host Defense During the Early-Induced and Adaptive Phases of the Immune Response," The Journal of Immunology, 2003, vol. 170, pp. 3812-3818.
Bone et al., "Definitions for Sepsis and Organ Failure and Guidelines for the Use of Innovative Therapies in Sepsis," Jun. 1992, vol. 101, pp. 1644-1655.
Cohen, Jonathan, "TERM-1 in sepsis," The Lancet, Sep. 8, 2001, vol. 358, pp. 776-778.
Cohen, Jonathan, "The immunopathogenesis of sepsis," Nature, Dec. 19/26, 2002, vol. 420, pp. 885-891.
Collart et al., "Regulation of Tumor Necrosis Factor Alpha Transcription in Macrophages: Involvement of Four κB-Like Motifs and Constitutive and Inducible Forms of NF-κB, "Molecular and Cellular Biology, Apr. 1990, vol. 10, No. 4, pp. 1498-1506.
Colonna et al., TREM-1 (Triggering Receptor Expressed on Myeloid Cells): A New Player in Acute inflammatory Responses, Journal of Infectious Diseases, 2003, 187, suppl. 2: pp. S397-S401.
Colonna et al., "TREMS in the Immune System and Beyond." Nature Reviews Immunology, Jun. 2003, vol. 3, No. 6, pp. 445-453 (printed as pp. 1-9).

(56) References Cited

OTHER PUBLICATIONS

Dinarello et al., "Proinflammatory and Ant-inflammatory Cytokines as Mediators in the Pathogenesis of Septic Shock," Chest, Dec. 1997, vol. 112, No. 6, pp. 321S-329S.
Echtenacher et al., "Tumor Necrosis Factor-Dependen Adhesions as a Major Protective Mechanism Early in Septic Peritonitis in Mice." Infection and Immunity, Jun. 2001, vol. 69, No. 6, pp. 3550-3555.
Echtenacher et al., "Requirement of Endogenous Tumor Necrosis Factor/Cachectin for Recovery from Experimental Peritonitis." Journal of Immunology, Dec. 1, 1990, vol. 145, No. 11, pp. 3762-3766.
Fisher et al., Treatment of Septic Shock with the Tumor Necrosis Factor Receptor: Fc Fusion Protein.: The New England Journal of Medicine, 1996, vol. 334, No. 26, pp. 1697-1702.
Gibot et al., "A Soluble Form of the Triggering Receptor Expressed on Myeloid Cells-1 Modulates the Inflammatory Response in Murine Sepsis," The Journal of Experimental Medicine, Dec. 6, 2004, Vo. 200 No. 11 pp. 1419-1426.
Griffin et al., "Abnormal Hear Rate Characteristics Preceding Neonatal Sepsis and Sepsis-Like Illness," Pediatric Research, 2003, vol. 53, No. 6, pp. 920-926.
Hiscott et al., "Characterization of a Functional Nf-κB Site in the Human Interleukin 1b Promoter: Evidence for a Positive Autoregulatory Loop," Molecular and Cellular Biology, Oct. 1993, vol. 13 No. 10, pp. 6231-6240.
Hotchkiss et al., "The Pathophysiology and Treatment of Sepsis," The New England Journal of Medicine, Jan. 9, 2003, pp. 138-150.
Keane et al., "Tuberculosis Associated with infliximab, a Tumor Necrosis Factor a-Neutralizing Agent," The New England Journal of Medicine, Oct. 11, 2001, vol. 345, No. 15, pp. 1098-1104.
Kelker et al., "Crystal Structure of Human Triggering Receptor Expressed on Myeloid Cells 1 (TREM-1) at 1.47 A," J. Mol. Biol. 2004, vol. 342, pp. 1237-1248.
Lantz et al., "Characterization In Vitro of a Human Tumor Necrosis Factor-binding Protein: A Soluble Form of a Tumor Necrosis Factor Receptor," J. Clin. Invest., Nov. 1990, vol. 89, pp. 1396-1402.
Lolis et al., "Therapeutic Approaches to Innate Immunity:Severe Sepsis and Septic Shock," Nature Reviews Drug Discovery, Aug. 2003, vol. 2, pp. 635-645.
NCBI Reference Sequences (RefSeq) NP_061113 (2 pgs).
NCBI Reference Sequences (RefSeq) NP_067381 (2 pgs).
Radaev et. al., "Crystal Structure of the Human Myeloid Cell Activation Receptor TREM-1," Structure, Dec. 2003, vol. 11, pp. 1527-1535.
Riedemann et al., "Novel strategies for the treatment of sepsis," Nature Medicine, May 2003, vol. 9, No. 5, pp. 517-524.
Stone, Richard, "Search for Sepsis Drugs Goes on Despite Past Failures." Science, Apr. 15, 1994, vol. 264, pp. 365-367.
Thoma-Uszynski et al., "Induction of Direct Antimicrobial Activity Through Mammalian Toll-Like Receptors," Science, Feb. 23, 2001, vol. 291, pp. 1544-1547.
Tsuji et al., "Simultaneous Onset of Acute Inflammatory Response, Sepsis-Like Symptoms and Intestinal Mucosal Injury After Cancer Chemotherapy," Int. J. Cancer, 2003, vol. 107, pp. 303-308.
Urban et al., "Nf-κB contacts DNA by a heterodimer of the p50 and p65 subunit," The EMBO Journal, 1991, vol. 10, No. 7, pp. 1817-1825.
Van Zee et al., "Tumor necrosis factor soluble receptors circulate during experimental and clinical inflammation and can protect against excessive tumor necrosis factor a in vitro and in vivo," Proc. Natl. Acad. Sci. USA, Jun. 1992, vol. 89, pp. 4845-4849.
Vincent et al., "Clinical Trials of Immunomodulatory Therapies in Severe Sepsis and Septic Shock," Clin. Infect. Dis., Apr. 15, 2002, vol. 34, pp. 1084-1093.
Warren, H. Sha, M.D., "Strategies for the Treatment of Sepsis," The New England Journal of Medicine, Mar. 27, 1997, vol. 336, No. 13, pp. 952-953.
Wasmuth et al., "Patient with acute on chromic liver failure display 'sepsis-like' immune paralysis," Journal of Hepatology, 2005, vol. 42, pp. 195-201.
Zwaveling et al., "High plasma tumor necrosis factor (TNF)-a concentrations and a sepsis-like syndrome in patients undergoing hyperthermic isolated limb perfusion with recombinant TNF-a, interferson-g, and melphalan," Crit Care Med, 1996, vol. 24, No. 5, pp. 765-770.
Database EMBL, Sequence from Patent WO200283856-A2, Sep. 17, 2003 "Human G-protein coupled receptor phosphorylation site peptide SEQ ID 131", retrieved from EBI Database accession No. ABJ38803.
Database EMBL, Sequence information from JP2000116377-A, Oct. 10, 2000 "N-terminus of porcine trypsin", retrieved from EBI Database accession No. AAB03087.
Wheeler et al., "Treating Patients with Severe Sepsis" NEJM 1999, 340: 207-214.
Attwood. "The Babel of Bioinformatics" Science 2000; 290: 471-473.
The Merck Manuals Online Medical Library (online). Whitehouse Station, NJ: Merck Research Laboratories, 2006-2007. (Retrieved on Nov. 19, 2007). Retrieved from the internet: < URL: http://www.merck.com/mmpe/print/sec06/ch068/ch068a.html >.
Standen et al. "Septic Shock" N. Engl. J. Med. 2000, 343: 447-448.
Redl et at, "Animal Models as the Basis of Pharmacologic Intervention in Trauma and Sepsis Patients," World J. Surg. 1996, 20: 487-492.
Mori et al., "A novel amino acid substitution at the receptor-binding site on the hemagglutinin of H3N2 influenza a viruses isolated from 6 cases with acute encephalopathy during the 1997-1998 season in Tokyo," Archives of Birology 1999, 144: 147-155.
Gencic et al., "Conservative amino acid substitution in the myelin proteolipid protein of jimpymsd mice," The Journ. Of Neuroscience 1990, 10: 117-124.
Schenk et al., "Trem-1—Expressing Intestinal Macrophages Crucially Amplify Chronic Inflammation in Experimental Colitis and Inflammatory Bowel Diseases," The Journ. Of Clinical Investigation, 2007, vol. 117, No. 10, pp. 3097-3106.

* cited by examiner

Figure 1A

```
                                   A        A'          B      CDR1     C
mTrem1   MRKAGLWGLLCVFFVSEVKAAIVLEEERYDLVEGQTLTVKCPFNIMKYANSQKAWQRLPD 60
hTrem1   MRKTRLWGLLWMLFVSELRAATKLTEEKNELKEGQTLDVKCDYTLEKFASSQKAWQIIRD 60
hTrem2   MEPLRLLILLFVTELSGAHNTTVFQG-----VAGQSLQVSCPYDSMKHWGRRKAWCRQLG 55
mTrem2   MGPLHQFLLLLITALSQALNTTVLQG-----MAGQSLRVSCTYDALKHWGRRKAWCRQLG 55
           *        **    :*       :   :    .   **:* *.*  :   *. . :***

C'     CDR2        C''       D           E             F
mTrem1   GKEPLTLVVTQRPFTRPSEVH--MGKFTLKHDPSEAMLQVQMTDLQVTDSGLYRCVIYHP 118
hTrem1   GEMPKTLACTENPSKNSHPVQ--VGRIILEDYHDHGLLRVRMVNLQVEDSGLYQCVIYQP 118
hTrem2   EKGPCQRVVSTHNLWLLSFLRRWNGSTAITDDTLGGTLTITLRNLQPHDAGLYQCQSLHG 115
mTrem2   EEGPCQRVVSTHGVWLLAFLKKRNGSTVIADDTLAGTVTITLKNLQAGDAGLYQCQSLRG 115
           : *    . : :      ::   *    :    . : : :**  *:***:*   :

CDR3  G        G'
mTrem1   PNDPVVLFHPVRLVVTKGSSDVFTPVIIPITRLTERPILITTKYSP---SDTTTRSLPK 175
hTrem1   PSPPIMLFDRIRLVVTKGFSGTPGSNENSIQNVYKIPPTTTKALCPLYTSPRTVTQAPPK 178
hTrem2   SEADTLRKVLVEVLADPLDHRDAGDLWFPGESESFEDAHVEHSISRSLLEGEIPFPPTSI 175
mTrem2   REAEVLQKVLVEVLEDPLDDQDAGDLWVPEESSSFEGAQVEHSTSR---NQETSFPPTSI 172
           :        :    :. ::                                  .  . .

mTrem1   PTAVVSSPGLGVIEINGIDADSVSTSSVTISVICGLLSKSLVFIILFIVTKRTFG- 230
hTrem1   SIAEVSTPDSEINLINVTDIIRVPVFNIVILLAGGFLSKSLVFSVLFAVTLRSFVP 234
hTrem2   LLLLACIFLIKILAASALWAAAWHGQKPGTHPPSELDCGHDPGYQLQTLPGLRDT- 230
mTrem2   LLLLACVLLSKFLAASILWAVARGRQKPGTPVVRGLDCGQDAGHQLQILTGPGGT- 227
           ..   .        .                :  .    *  :.
```

Figure 1B

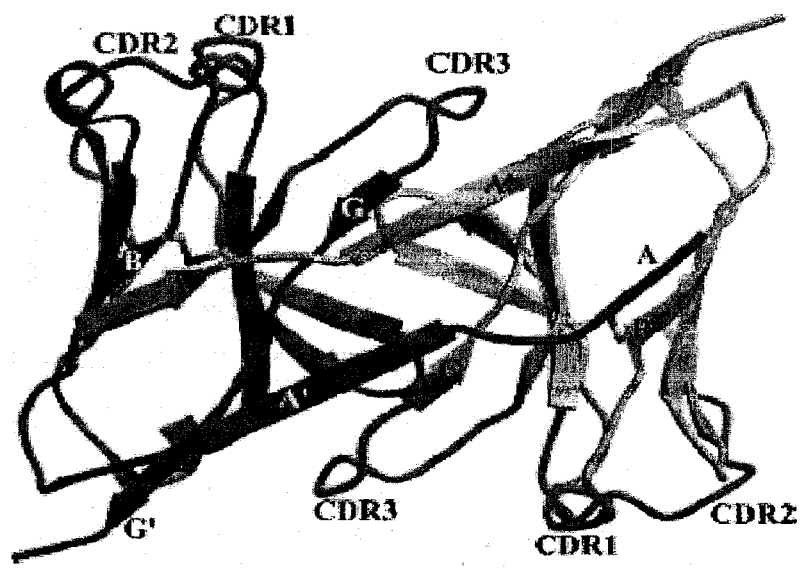

Figure 7
A
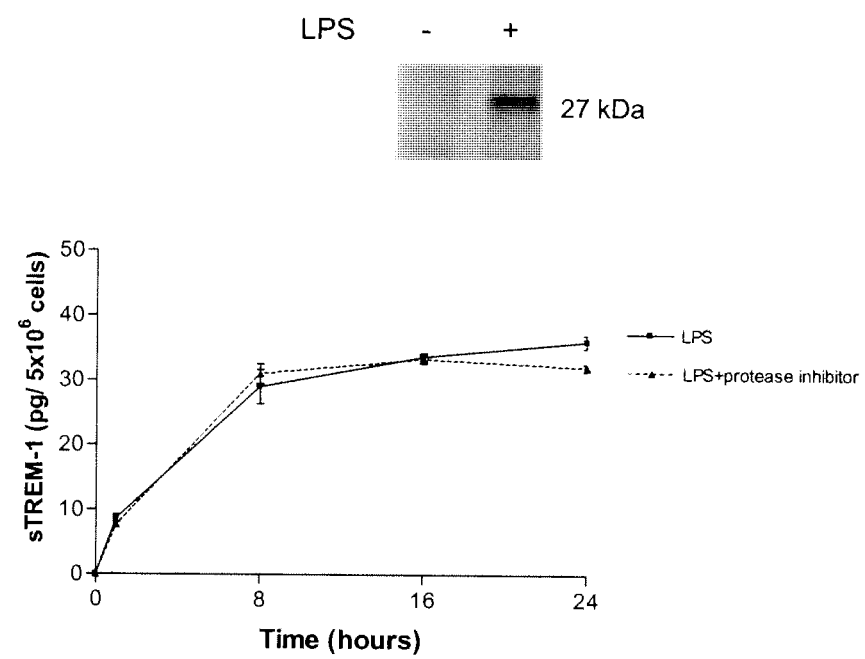
B
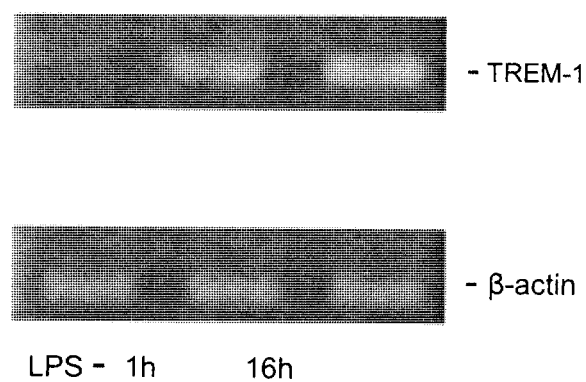

THERAPEUTIC TREM-1 PEPTIDES

This application is a continuation of U.S. patent application Ser. No. 12/320,707, filed Feb. 2, 2009, which is a continuation-in-part of U.S. patent application Ser. No. 11/284,086, filed on Nov. 22, 2005, which claims priority from United Kingdom Patent Application No. 0426146.7, filed on Nov. 29, 2004, and Japanese Patent Application No. 2005-146848, filed on May 19, 2005. The contents of these applications are incorporated herein by reference in their entirety.

The present invention relates to the field of immunology. More particularly, the present invention relates to inflammation and the use of proteins and peptides containing certain sequences of the TREM-1 protein and their functional equivalents (referred to herein as TREM1-peptides) in the treatment of disease, for example, sepsis, septic shock and inflammatory bowel disease (IBD).

Sepsis constitutes a significant consumption of intensive care resources and remains an ever-present problem in the intensive care unit. It has been estimated that between 400 000 and 500 000 patients are so affected each year in both the USA and Europe. Morbidity and mortality have remained high despite improvements in both supportive and anti-microbial therapies. Mortality rates vary from 40% for uncomplicated sepsis to 80% in those suffering from septic shock and multi-organ dysfunction. The pathogenesis of the conditions is now becoming better understood. Greater understanding of the complex network of immune, inflammatory and haematological mediators may allow the development of rational and novel therapies.

Following an infection, innate and cognitive immune responses develop in sequential phases that build-up in specificity and complexity, resulting ultimately in the clearance of infectious agents and restoration of homeostasis. The innate immune response serves as the first line of defence and is initiated upon activation of pattern recognition receptors, such as Toll-like receptors (TLRs) (1, 2), by various pathogen-associated microbial patterns (PAMPs) (3). Activation of the TLRs triggers the release of large quantities of such cytokines as TNF-α and IL-1β, which, in case of such massive infections as sepsis, can precipitate tissue injury and lethal shock (4, 5). Although antagonists of TNF-α and IL-1β appeared in this context as possibly interesting therapeutic agents of sepsis, they have unfortunately shown limited efficacy in clinical trials (6-8). This could be due to the fact that these cytokines are necessary for the clearance of infections, and that their removal would allow for fatal bacterial growth (9-11).

Another receptor involved in, inter alia, response to infection, triggering receptor expressed on myeloid cells-1 (TREM-1) is a member of a recently discovered family of receptors, the TREM family, expressed on the surface of neutrophils and a subset of monocytes. TREM receptors activate myeloid cells via association with the adaptor molecule DAP12. Engagement of TREM-1 has been reported to trigger the synthesis of pro-inflammatory cytokines in the presence of microbial products.

The triggering receptor expressed on myeloid cells (TREM)-1 is a recently discovered cell-surface molecule that has been identified both on human and murine polymorphonuclear neutrophils and mature monocytes (12). It belongs to the immunoglobulin superfamily and activates downstream signalling pathways with the help of an adapter protein called DAP12 (12-15). Bouchon and co-workers have shown that the expression of TREM-1 was greatly up-regulated on neutrophils and monocytes in the presence of such bacteria as *Pseudomonas aeruginosa* or *Staphylococcus aureus*, both in cell culture and in tissue samples from patients with infection (16). In striking contrast, TREM-1 was not up-regulated in samples from patients with non-infectious inflammatory diseases such as psoriasis, ulcerative colitis or vasculitis caused by immune complexes (16). Moreover, when TREM-1 is bound to its ligand, there is a synergistic effect of LPS and an amplified synthesis of the pro-inflammatory cytokines TNF-α and GM-CSF, together with an inhibition of IL-10 production (17). In a murine model of LPS-induced septic shock, blockade of TREM-1 signalling protected the animals from death, further highlighting the crucial role of this molecule (13, 16).

Recent studies demonstrate that TREM-1 plays a critical role in the inflammatory response to infection (see BOUCHON et al. (2000) J. Immunol. 164:4991-4995). Expression of TREM-1 is increased on myeloid cells in response to both bacterial and fungal infections in humans. Similarly, in mice the induction of shock by lipopolysaccharide (LPS) is associated with increased expression of TREM-1. Further, treatment of mice with a soluble TREM-1/Ig fusion protein, as a 'decoy' receptor, protects mice from death due to LPS or *E.coli*.

Triggering via TREM-1 results in the production of pro-inflammatory cytokines, chemokines and reactive oxygen species, and leads to rapid degranulation of neutrophilic granules, and phagocytosis. Since interfering with TREM-1 engagement leads to the simultaneous reduction in production and secretion of a variety of proinflammatory mediators, TREM-1 represents an attractive target for treating chronic inflammatory disorders. Indeed, a role for TREM-1 has been demonstrated in a variety of inflammatory disorders, including (but not limited to) acute and chronic inflammatory disorders, sepsis, acute endotoxemia, encephalitis, Chronic Obstructive Pulmonary Disease (COPD), allergic inflammatory disorders, asthma, pulmonary fibrosis, pneumonia, Community acquired pneumonia (CAP), Ventilator associated pneumonia (VAP), Acute respiratory infection, Acute respiratory distress syndrome (ARDS), Infectious lung diseases, Pleural effusion, Peptic ulcer, Helicobacter pylori infection, hepatic granulomatosis, arthritis, rheumatoid arthritis, osteoarthritis, inflammatory osteolysis, ulcerative colitis, psoriasis, vasculitis, autoimmune disorders, thyroiditis, Meliodosis, (mesenteric) Ischemia reperfusion, Filovirus infection, Infection of the urinary tract, Bacterial meningitis, *Salmonella enterica* infection, Marburg and Ebola viruses infections, and in particular Inflammatory Bowel Disease (IBD). Inflammatory bowel disease (IBD) covers a group of disorders in which the intestines become inflamed (red and swollen), probably as a result of an immune reaction of the body against its own intestinal tissue. Two major types of IBD are described: ulcerative colitis (UC) and Crohn disease (CD). Ulcerative colitis is limited to the colon (large intestine). Crohn disease can involve any part of the gastrointestinal tract from the mouth to the anus, but it most commonly affects the small intestine and/or the colon. Both ulcerative colitis and Crohn disease vary in the intensity and severity during the course of the disease. When there is severe inflammation, the disease is considered to be in an active stage, and the person experiences a flare-up of the condition. When the degree of inflammation is less (or absent), the person usually is without symptoms, and the disease is considered to be in remission. In IBD factor or factors trigger the body's immune system to produce an inflammatory reaction in the intestinal tract that continues without control. As a result of the inflammatory reaction, the intestinal wall is damaged leading to bloody diarrhea and abdominal pain.

U.S. Pat. No. 6,420,526 entitled "186 Secreted Proteins" claims unspecified and unexemplified isolated fragments of TREM-1 containing at least 30 contiguous amino acids of human TREM-1. No biological data relating to such fragments are provided.

As described in US2003165875A, fusion proteins between human IgG1 constant region and the extracellular domain of mouse TREM-1 or that of human TREM-1 show an effect against endotoxemia in mice.

The inventors have surprisingly found that certain peptides derived from the TREM-1 protein are capable of acting as antagonists of the TREM-1 protein and therefore have applications in the treatment of sepsis, septic shock and inflammatory bowel disease (IBD). The Inventors further demonstrate that the same peptides also modulate in vivo the pro-inflammatory cascade triggered by infection, thus inhibiting hyper-responsiveness and death in an animal model of sepsis, and that blocking TREM-1 attenuates the symptoms of IBD in mice Previously, the Inventors have identified a soluble form of TREM-1 (sTREM-1) and observed significant levels in serum samples from septic shock patients but not controls. As also described herein the Inventors have investigated its putative role in the modulation of inflammation during sepsis (see Gibot et al. (2004) Ann. Intern. Med. 141(1):9-15 and Gibot et al. (2004) N. Engl. J. Med. 350(5):451-8).

As described herein the Inventors show that a soluble form of TREM-1 (sTREM-1) is released in the peripheral blood during infectious aggression in mouse. The Inventors also confirm monocytes as a major source of sTREM, and show that synthetic peptides mimicking a part of the extra-cellular domain of TREM-1 can modulate cytokine production by activated monocytes in vitro.

The Inventors have observed that sTREM-1 is secreted by monocytes activated in vitro by LPS, as well as in the serum of animals involved in an experimental model of septic shock. Both in vitro and in vivo, synthetic peptides mimicking a short highly conserved domain of sTREM-1 attenuate cytokine production by human monocytes and protect septic animals from hyper-responsiveness and death. These peptides are efficient not only in preventing but also in down-regulating the deleterious effects of pro-inflammatory cytokines. These data demonstrate that in vivo modulation of TREM-1 by TREM-1 peptides is a valuable therapeutic tool for the treatment of infection, for example sepsis or septic shock or for the treatment of sepsis-like conditions Accordingly, the present invention provides methods and compositions for the treatment of infectious disease, in particular, sepsis and septic shock or for the treatment of sepsis-like conditions Other diseases or disorders that may also be treated by the methods and compositions of the present invention include any inflammatory disorder (or other disorder) that is mediated by the binding of the TREM-1 ligand to a TREM-1 receptor. Examples of inflammatory disorders include (but are not limited to) acute and chronic inflammatory disorders, sepsis, acute endotoxemia, encephalitis, Chronic Obstructive Pulmonary Disease (COPD), allergic inflammatory disorders, asthma, pulmonary fibrosis, pneumonia, Community acquired pneumonia (CAP), Ventilator associated pneumonia (VAP), Acute respiratory infection, Acute respiratory distress syndrome (ARDS), Infectious lung diseases, Pleural effusion, Peptic ulcer, Helicobacter pylori infection, hepatic granulomatosis, arthritis, rheumatoid arthritis, osteoarthritis, inflammatory osteolysis, ulcerative colitis, psoriasis, vasculitis, autoimmune disorders, thyroiditis, Meliodosis, (mesenteric) lschemia reperfusion, Filovirus infection, Infection of the urinary tract, Bacterial meningitis, *Salmonella enterica* infection, Marburg and Ebola viruses infections, and in particular Inflammatory Bowel Disease (IBD), As described herein, the Inventors have determined that several peptides of the extracellular portion of the TREM-1 protein (see Table 1), which incorporate sequences from "CDR2" and "CDR3" surprisingly have activity similar to previously described fusion proteins of IgG1 constant region and the extracellular domain of TREM-1 in models of sepsis. These peptides also have advantages over the protein particularly in terms of cost of manufacture.

Thus, the invention provides polypeptides comprising one or more sequences derived from CDR2 or CDR3 of a TREM-1 protein. Preferably, said polypeptides comprise less than 30 contiguous amino acids of said TREM-1 protein.

As shown in Table 1, examples of such peptides or polypeptides, contain or comprise for example 15-25 amino acid ("AA") peptides from the TREM-1 protein and contain or comprise all or part of a CDR domain (3-6 AAs) of the receptor flanked by natural sequences from the protein that can vary in length so long as function of the CDR-like domain is not lost. Such peptides are derived from the TREM-1 receptor protein amino acid sequence for example, as shown in Table 2 (human) and Table 3 (mouse).

Table 1 shows peptides derived from mouse TREM-1 "mPX" (NCBI Reference Sequences (RefSeq) NP_067381) or human TREM-1 "hPX"" (NCBI Reference Sequences (RefSeq) NP_061113). Underlined amino acids span the human TREM-1 Complementarity Determining Regions (CDR), as described by Radaev et al. 2003 Structure (Camb.) 11 (12), 1527-1535 (2003).

Table 2 shows the human TREM-1 amino acid sequence NP_061113. Underlined amino acids span the human TREM-1 Complementarity Determining Regions (CDR) 2 (RPSKNS; [SEQ ID NO:20]) and 3 (QPPKE [SEQ ID NO:21]), as described by Radaev et al. 2003 Structure (Camb.) 11 (12), 1527-1535 (2003).

Table 3 shows the mouse TREM-1 amino acid sequence NP_067381. Underlined amino acids span the mouse TREM-1 Complementarity Determining Regions (CDR) 2 (RPFTRP; [SEQ ID NO:22]) and 3 (HPPND; [SEQ ID NO:23]).

TABLE 1

Peptides including sequences from human and mouse TREM-1 CDR 2 and CDR 3 hCDR 2

| | | |
|---|---|---|
| mP1 (67-89): | [SEQ ID NO: 3] | LVVTQRPFTRPSEVHMGKFTLKH |
| hP1 (67-89): | [SEQ ID NO: 16] | LACTERPSKNSHPVQVGRIILED | hCDR 3

| | | |
|---|---|---|
| mP2 (114-136): | [SEQ ID NO: 4] | VIYHPPNDPVVLFHPVRLVVTKG |
| mP4 (103-123): | [SEQ ID NO: 6] | LQVTDSGLYRCVIYHPPNDPV |
| mP5 (103-119): | [SEQ ID NO: 7] | LQVTDSGLYRCVIYHPP |

TABLE 1-continued

Peptides including sequences from human and mouse
TREM-1 CDR 2 and CDR 3

```
hP2 (114-136): [SEQ ID NO: 17]         VIYQPPKEPHMLFDRIRLVVTKG
hP4 (103-123): [SEQ ID NO: 18] LQVEDSGLYQCVIYQPPKEPH
hP5 (103-119): [SEQ ID NO: 19] LQVEDSGLYQCVIYQPP
```

TABLE 2

Human TREM-1 amino acid sequence NP_061113

```
  1 MRKTRLWGLL WMLFVSELRA ATKLTEEKYE LKEGQTLDVK CDYTLEKFAS SQKAWQIIRD

61 GEMPKTLACT ERPSKNSHPV QVGRIILEDY HDHGLLRVRM VNLQVEDSGL YQCVIYQPPK

121 EPHMLFDRIR LVVTKGFSGT PGSNENSTQN VYKIPPTTTK ALCPLYTSPR TVTQAPPKST

181 ADVSTPDSEI NLTNVTDIIR VPVFNIVILL AGGFLSKSLV FSVLFAVTLR SFVP
[SEQ ID NO: 1]
```

TABLE 3

Mouse TREM-1 amino acid sequence NP_067381

```
  1 MRKAGLWGLL CVFFVSEVKA AIVLEEERYD LVEGQTLTVK CPFNIMKYAN SQKAWQRLPD

61 GKEPLTLVVT QRPFTRPSEV HMGKFTLKHD PSEAMLQVQM TDLQVTDSGL YRCVIYHPPN

121 DPVVLFHPVR LVVTKGSSDV FTPVIIPITR LTERPILITT KYSPSDTTTT RSLPKPTAVV

181 SSPGLGVTII NGTDADSVST SSVTISVICG LLSKSLVFII LFIVTKRTFG
[SEQ ID NO: 2]
```

Accordingly, the invention provides isolated or recombinantly prepared polypeptides or peptides comprising or consisting essentially of one or more sequences derived from CDR2 or CDR3 of a TREM-1 protein, or fragments, homologues, derivatives, fusion proteins or variants of such polypeptides, as defined herein, which are herein collectively referred to as "polypeptides or peptides of the invention" or "TREM-1 peptides or TREM-1 polypeptides", preferably such entities comprise less than 30 contiguous amino acids of a TREM-1 protein, for example as shown in Table 2 or Table 3. Generally where polypeptides or proteins of the invention or fragments, homologues, derivatives, or variants thereof are intended for use (for example treatment) in a particular species, the sequences of CDR2 or CDR3 of a TREM-1 protein are chosen from the TREM-1 protein amino acid sequence of that species, or if the sequence is not known, an analogous species. For example, polypeptides or proteins of the invention for the treatment of human disease, in particular sepsis, septic shock or sepsis-like conditions, will comprise one or more sequences comprising all or part of CDR2 or CDR3 from the human TREM-1 protein.

Furthermore, the invention provides isolated polypeptides or proteins comprising an amino acid sequence that is at least about 60%, 70%, 75%, 80%, 85%, 90%, 95%, or 98% identical to the amino acid sequence of SEQ ID NO:20, 21, 22, 23 or fragments, homologues, derivatives, or variants thereof. The invention also provides isolated peptides, polypeptides or proteins comprising an amino acid sequence that comprises or consists of at least about 3, 4, 5, 6, 7, 8, 9, 10, 11, 12, 13, 14, 15, 16, 17, 18, 19, 20, 21 22, 23, 24, 25, 26, 27, 28, or 29 or more contiguous amino acids of a TREM-1 protein of which 3 or more contiguous amino acids are derived from the sequences of SEQ ID NO:20, 21, 22 or 23 (in other words a sequence representing all, or part of CDR2 or CDR3 of a TREM-1 protein is present in the peptide, polypeptide or protein), or fragments, homologues, derivatives, or variants thereof. In preferred embodiments, such peptides, polypeptides or proteins, or fragments, homologues, derivatives or variants thereof have a biological activity of a TREM-1 full-length protein, such as antigenicity, immunogenicity, triggering of proinflammatory chemokines and cytokines, mobilization of cytosolic $Ca^{2+}$, protein tyrosine-phosphorylation, mediator release, and other activities readily assayable. Generally, such peptides, polypeptides or proteins or fragments, homologues, derivatives or variants thereof are capable of treating sepsis, septic shock or sepsis-like conditions, or are active in experimental models of sepsis, septic shock or sepsis-like conditions, for example by acting as antagonists of the activity of the TREM-1 receptor. Such peptides, polypeptides or proteins or fragments, homologues, derivatives or variants thereof are characterised by the ability to treat, ameliorate, or lessen the symptoms of sepsis, septic shock or sepsis-like conditions.

In particular, the invention provides, a TREM-1 polypeptide having activity against sepsis, septic shock or sepsis-like conditions which consists of (i) a contiguous sequence of 5 to 29, for example 15-25, amino acids corresponding to the native TREM-1 protein sequence which includes at least 3 amino acids from the CDR2 or CDR3 sequences; or (ii) such a sequence in which one or more (e.g. one, two or three) amino acids are substituted conservatively with another amino acid provided, however that at least 3 amino acids from the CDR2 or CDR3 sequences are not substituted; or (iii) a sequence of (i) or (ii) linked at one or both of its N and C termini to a heterologous polypeptide. For example, in a polypeptide wherein the native TREM-1 protein sequence is the human sequence identified as (SEQ ID NO: 1), the CDR2 and CDR3 sequences are RPSKNS (SEQ ID NO:20) and QPPKE (SEQ ID NO:21) respectively. In such polypeptides, the at least 3 amino acids from the CDR2 or CDR3 sequences can be QPP, PPK, PKE, RPS, PSK, SKN or KNS. Such polypeptides may comprise the sequence QPPK ([SEQ ID NO:24), QPPKE (SEQ ID NO:21) or RPSKNS (SEQ ID NO:20). For example, in a polypeptide wherein the native TREM-1 protein sequence is the mouse sequence identified as (SEQ ID NO: 2) the CDR2 and CDR3 sequences are RPFTRP (SEQ ID NO:22) and HPPND (SEQ ID NO:23) respectively. In such polypeptides, the at least 3 amino acids from the CDR2 or CDR3 sequences can be HPP, PPN, PND, RPF, PFT, FTR or TRP. Such polypeptides may comprise the sequences HPP, HPPN (SEQ ID NO:25), HPPND (SEQ ID NO:23) or RPFTRP (SEQ ID NO:22).

In certain embodiments, the polypeptide of the invention is or comprises SEQ ID No. 7 which is disclosed in Gibot et al (2004) J Exp Med 200, 1419-1426.

In certain embodiments the polypeptide of the invention neither is nor comprises SEQ ID No. 7.

In certain embodiments the polypeptide of the invention is or comprises a sequence selected from SEQ ID Nos. 3, 4 and 6.

In certain embodiments the polypeptide of the invention is or comprises a sequence selected from SEQ ID Nos. 16, 17, 18 and 19.

In certain embodiments the polypeptide of the invention is or comprises a sequence derived from CDR2.

In certain embodiments the polypeptide of the invention is or comprises a sequence derived from CDR3.

The polypeptides or peptides of the invention are provided for use in therapy, in particular in the treatment of sepsis, septic shock and sepsis-like conditions, and for use in the manufacture of a medicament for the treatment of sepsis, septic shock and sepsis-like conditions. Further provided are compositions and pharmaceutical compositions containing polypeptides or peptides of the invention and methods of treatment of sepsis, septic shock and sepsis-like conditions using polypeptides or peptides of the invention. In addition the polypeptides or peptides of the invention are provided for use in therapy to restore haemodynamic parameters in sepsis, septic shock and sepsis-like conditions and for use in the manufacture of a medicament for the treatment of aberrant haemodynamic parameters in sepsis, septic shock and sepsis-like conditions.

The term "triggering receptor expressed on myeloid cells" or "TREM" refers to a group of activating receptors which are selectively expressed on different types of myeloid cells, such as mast cells, monocytes, macrophages, dendritic cells (DCs), and neutrophils, and may have a predominant role in immune and inflammatory responses. TREMs are primarily transmembrane glycoproteins with a Ig-type fold in their extracellular domain and, hence, belong to the Ig-SF. These receptors contain a short intracellular domain, but lack docking motifs for signaling mediators and require adapter proteins, such as DAP12, for cell activation.

The term "myeloid cells" as used herein refers to a series of bone marrow-derived cell lineages including granulocytes (neutrophils, eosinophils, and basophils), monocytes, macrophages, and mast cells. Furthermore, peripheral blood dendritic cells of myeloid origin, and dendritic cells and macrophages derived in vitro from monocytes in the presence of appropriate culture conditions, are also included.

The term "sepsis, septic shock" or "sepsis or septic shock" as defined herein, refers to sub-groups of systemic inflammatory response syndrome (SIRS). The term "sepsis" is generally reserved for SIRS when infection is suspected or proven. A pattern of physiological variables have been shown in critically ill patients in response to a range of insults including; trauma, burns, pancreatitis and infection. These include inflammatory responses, leucocytosis or severe leucopaenia, hyperthermia or hypothermia, tachycardia and tachypnoea and have been collectively termed the systemic inflammatory response syndrome (SIRS). This definition emphasises the importance of the inflammatory process in these conditions regardless of the presence of infection. Sepsis is further stratified into severe sepsis when there is evidence of organ hypoperfusion, made evident by signs of organ dysfunction such as hypoxaemia, oliguria, lactic acidosis or altered cerebral function. "Septic shock" is severe sepsis usually complicated by hypotension, defined in humans as systolic blood pressure less than 90 mmHg despite adequate fluid resuscitation. Sepsis and SIRS may be complicated by the failure of two or more organs, termed multiple organ failure (MOF), due to disordered organ perfusion and oxygenation. In addition to systemic effects of infection, a systemic inflammatory response may occur in severe inflammatory conditions such as pancreatitis and burns. The appearance of signs of an inflammatory response is less well defined following traumatic insults. In the intensive care unit, gram-negative bacteria are implicated in 50 to 60% of sepsis cases with gram-positive bacteria accounting for a further 35 to 40% of cases. The remainder of cases are due to the less common causes of fungi, viruses and protozoa.

The term "sepsis-like conditions" as used herein refers to those states in which a patient presents with symptoms similar to sepsis or septic shock but where an infectious agent is not the primary or initial cause of a similar cascade of inflammatory mediators and/or change in haemodynamic parameters as seen in cases of sepsis, for example in patients with acute or chronic liver failure (see Wasmuth H E, et al. J Hepatol. 2005 February; 42(2):195-201), in cases of post-resuscitation disease after cardiac arrest (see Adrie C et al. Curr Opin Crit Care. 2004 June; 10(3):208-12) in the treatment of sepsis-like symptoms after cancer chemotherapy (see Tsuji E et al. Int J Cancer. 2003 Nov. 1; 107(2):303-8) in patients undergoing hyperthermic isolated limb perfusion with recombinant TNF-alpha or similar treatments (see Zwaveling J H et al. Crit Care Med. 1996 May; 24(5):765-70) or sepsis-like illness in neonates (see Griffin M P et al. Pediatr Res. 2003 June; 53(6):920-6).

The term "activity against sepsis, septic shock or sepsis-like conditions" as used herein refers to the capability of a molecule, for example a peptide, polypeptide or engineered antibody, to treat sepsis, septic shock or sepsis-like conditions, or be active in experimental models of sepsis, septic shock or sepsis-like conditions, for example by acting as an antagonist of the activity of the TREM-1 receptor.

Typically the indication for polypeptides of the invention is sepsis or septic-shock or Inflammatory Bowel Disease (IBD). Other indications may include any inflammatory disorder (or other disorder) that is mediated by the binding of the TREM-1 ligand to a TREM-1 receptor. Examples of inflammatory disorders include (but are not limited to) acute and chronic inflammatory disorders, sepsis, acute endotoxemia, encephalitis, Chronic Obstructive Pulmonary Disease (COPD), allergic inflammatory disorders, asthma, pulmonary fibrosis, pneumonia, Community acquired pneumonia (CAP), Ventilator associated pneumonia (VAP), Acute respiratory infection, Acute respiratory distress syndrome (ARDS), Infectious lung diseases, Pleural effusion, Peptic ulcer, Helicobacter pylon infection, hepatic granulomatosis, arthritis, rheumatoid arthritis, osteoarthritis, inflammatory osteolysis, ulcerative colitis, psoriasis, vasculitis, autoimmune disorders, thyroiditis, Meliodosis, (mesenteric) lschemia reperfusion, Filovirus infection, Infection of the urinary tract, Bacterial meningitis, *Salmonella enterica* infection, Marburg and Ebola viruses infections.

The term "substantial sequence identity", when used in connection with peptides/amino acid sequences, refers to peptides/amino acid sequences which are substantially identical to or similar in sequence, giving rise to a homology in conformation and thus to similar biological activity. The term is not intended to imply a common evolution of the sequences.

Typically, peptides/amino acid sequences having "substantial sequence identity" are sequences that are at least 50%, more preferably at least 80%, identical in sequence, at least over any regions known to be involved in the desired activity. Most preferably, no more than five residues, other than at the termini, are different. Preferably, the divergence in sequence, at least in the aforementioned regions, is in the form of "conservative modifications"

To determine the percent sequence identity of two peptides/amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). For example, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the first amino acid sequence which has for example 100 amino acid residues, at least 30, preferably at least 40, more preferably at least 50, even more preferably at least 60, and even more preferably at least 70, 80 or 90 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. The comparison of sequences and determination of percent identity between two sequences can be accomplished using a mathematical algorithm. In one embodiment, the percent identity between two amino acid sequences is determined using the Needleman and Wunsch (*J. Mol. Biol.* (48):444-453 (1970)) algorithm which has been incorporated into the GAP program in the GCG software package (available online at the GCG website), using either a Blossom 62 matrix or a PAM250 matrix, and a gap weight of 16, 14, 12, 10, 8, 6, or 4, and a length weight of 1, 2, 3, 4, 5, or 6. In another embodiment, the percent identity between two nucleotide sequences is determined using the GAP program in the GCG software package (available online at the GCG website), using a NWSgapdna.CMP matrix and a gap weight of 40, 50, 60, 70, or 80, and a length weight of 1, 2, 3, 4, 5, or 6. In another embodiment, the percent identity between two amino acid or nucleotide sequences is determined using the algorithm of E. Meyers and W. Miller (*CABIOS*, 4:11-17 (1989)) which has been incorporated into the ALIGN program (version 2.0), using a PAM120 weight residue table, a gap length penalty of 12, and a gap penalty of 4. The nucleic acid and protein sequences of the present invention can further be used as a "query sequence" to perform a search against public databases to identify, for example, other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to NIP2b, NIP2cL, and NIP2cS nucleic acid molecules of the invention. BLAST protein searches can be performed with the XBLAST program, score=50, wordlength=3 to obtain amino acid sequences homologous to NIP2b, NIP2cL, and NIP2cS protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. These programs are publically available on the National Center for Biotechnology Information ("NCBI") website.

The terms "protein" and "polypeptide" are used interchangeably herein. The term "peptide" is used herein to refer to a chain of two or more amino acids or amino acid analogues (including non-naturally occurring amino acids), with adjacent amino acids joined by peptide (—NHCO—) bonds. Thus, the peptides of the invention include oligopeptides, polypeptides, proteins, mimetopes and peptidomimetics. Methods for preparing mimetopes and peptidomimetics are known in the art.

The terms "mimetope" and "peptidomimetic" are used interchangeably herein. A "mimetope" of a compound X refers to a compound in which chemical structures of X necessary for functional activity of X have been replaced with other chemical structures which mimic the conformation of X. Examples of peptidomimetics include peptidic compounds in which the peptide backbone is substituted with one or more benzodiazepine molecules (see e.g., James, G. L. et al. (1993) *Science* 260:1937-1942) and "retro-inverso" peptides (see U.S. Pat. No. 4,522,752 to Sisto). The terms "mimetope" and "peptidomimetic" also refer to a moiety, other than a naturally occurring amino acid, that conformationally and functionally serves as a substitute for a particular amino acid in a peptide-containing compound without adversely interfering to a significant extent with the function of the peptide. Examples of amino acid mimetics include D-amino acids. Peptides substituted with one or more D-amino acids may be made using well known peptide synthesis procedures. Additional substitutions include amino acid analogues having variant side chains with functional groups, for example, b-cyanoalanine, canavanine, djenkolic acid, norleucine, 3-phosphoserine, homoserine, dihydroxyphenylalanine, 5-hydroxytryptophan, 1-methylhistidine, or 3-methylhistidine As used herein an "analogue" of a compound X refers to a compound which retains chemical structures of X necessary for functional activity of X, yet which also contains certain chemical structures which differ from X. An example of an analogue of a naturally-occurring peptide is a peptide which includes one or more non-naturally-occurring amino acids. The term "analogue" is also intended to include modified mimetopes and/or peptidomimetics, modified peptides and polypeptides, and allelic variants of peptides and polypeptides. Analogues of a peptide will therefore produce a peptide analogue that is substantially homologous or, in other words, has substantial sequence identity to the original peptide. The term "amino acid" includes its art recognized meaning and broadly encompasses compounds of formula I:

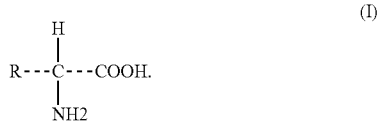

Preferred amino acids include the naturally occurring amino acids, as well as synthetic derivatives, and amino acids derived from proteins, e.g., proteins such as casein, i.e., casamino acids, or enzymatic or chemical digests of, e.g., yeast, an animal product, e.g., a meat digest, or a plant product, e.g., soy protein, cottonseed protein, or a corn steep liquor (see, e.g., Traders' Guide to Fermentation Media, Traders Protein, Memphis, Tenn. (1988), Biotechnology: A Textbook of Industrial Microbiology, Sinauer Associates, Sunderland, Mass. (1989), and Product Data Sheet for Corn Steep Liquor, Grain Processing Corp., IO).

The term "naturally occurring amino acid" includes any of the 20 amino acid residues which commonly comprise most polypeptides in living systems, rarer amino acids found in fibrous proteins (e.g., 4-hydorxyproline, 5-hydroxylysine, —N-methyllysine, 3-methylhistidine, desmosine, isodesmosine), and naturally occurring amino acids not found in proteins (e.g., -aminobutryic acid, homocysteine, homoserine, citrulline, ornithine, canavanine, djenkolic acid, and -cyanoalanine).

The term "side chain of a naturally occurring amino acid" is intended to include the side chain of any of the naturally occurring amino acids, as represented by R in formula I. One skilled in the art will understand that the structure of formula I is intended to encompass amino acids such as proline where the side chain is a cyclic or heterocyclic structure (e.g., in proline R group and the amino group form a five-membered heterocyclic ring.

The term "homologue," as used herein refers to any member of a series of peptides or polypeptides having a common biological activity, including antigenicity/immunogenicity and inflammation regulatory activity, and/or structural domain and having sufficient amino acid as defined herein. Such homologues can be from either the same or different species of animals.

The term "variant" as used herein refers either to a naturally occurring allelic variation of a given peptide or a recombinantly prepared variation of a given peptide or protein in which one or more (e.g. one, two or three) amino acid residues have been modified by amino acid substitution, addition, or deletion.

The term "derivative" as used herein refers to a variation of given peptide or protein that are otherwise modified, i.e., by covalent attachment of any type of molecule, preferably having bioactivity, to the peptide or protein, including non-naturally occurring amino acids.

Preferably, such homologues, variants and derivatives are capable of treating sepsis, septic shock or sepsis-like conditions, or are active in experimental models of sepsis, septic shock or sepsis-like conditions, or are capable of treating IBD or other inflammatory disorder, for example by acting as antagonists of the activity of the TREM-1 receptor.

An "isolated" or "purified" peptide or protein is substantially free of cellular material or other contaminating proteins from the cell or tissue source from which the protein is derived, or substantially free of chemical precursors or other chemicals when chemically synthesized.

The language "substantially free of cellular material" includes preparations of a polypeptide/protein in which the polypeptide/protein is separated from cellular components of the cells from which it is isolated or recombinantly produced. Thus, a polypeptide/protein that is substantially free of cellular material includes preparations of the polypeptide/protein having less than about 30%, 20%, 10%, 5%, 2.5%, or 1%, (by dry weight) of contaminating protein. When the polypeptide/protein is recombinantly produced, it is also preferably substantially free of culture medium, i.e., culture medium represents less than about 20%, 10%, or 5% of the volume of the protein preparation. When polypeptide/protein is produced by chemical synthesis, it is preferably substantially free of chemical precursors or other chemicals, i.e., it is separated from chemical precursors or other chemicals which are involved in the synthesis of the protein. Accordingly, such preparations of the polypeptide/protein have less than about 30%, 20%, 10%, 5% (by dry weight) of chemical precursors or compounds other than polypeptide/protein fragment of interest. In a preferred embodiment of the present invention, polypeptides/proteins are isolated or purified.

In addition to the polypeptides described above, polypeptides of the invention also encompass those polypeptides having a common biological activity and/or structural domain and having sufficient amino acid identity (homologues) as defined herein. These homologues can be from either the same or different species of animal, preferably from mammals, more preferably from rodents, such as mouse and rat, and most preferably from human. Preferably, they exhibit at least one structural and/or functional feature of TREM-1, and are preferably, capable of treating sepsis, septic shock or sepsis-like conditions, for example by acting as antagonists of the activity of the TREM-1 receptor. Such modifications include amino acid substitution, deletion, and/or insertion. Amino acid modifications can be made by any method known in the art and various methods are available to and routine for those skilled in the art.

Additionally, in making amino acid substitutions, generally the amino acid residue to be substituted can be a conservative amino acid substitution (i.e. "substituted conservatively"), for example, a polar residue is substituted with a polar residue, a hydrophilic residue with a hydrophilic residue, hydrophobic residue with a hydrophobic residue, a positively charged residue with a positively charged residue, or a negatively charged residue with a negatively charged residue. Moreover, generally, the amino acid residue to be modified is not highly or completely conserved across species and/or is critical to maintain the biological activities of the peptide and/or the protein it derives from.

Peptides of the invention may be directly synthesised in any convenient way. Generally the reactive groups present (for example amino, thiol and/or carboxyl) will be protected during overall synthesis. A proportion of the peptides of the invention, i.e. those wherein the comprised amino acids are genetically coded amino acids, will be capable of being expressed in prokaryotic and eukaryotic hosts by expression systems well known to the man skilled in the art. Methods for the isolation and purification of e. g. microbially expressed peptides are also well known. Polynucleotides which encode these peptides of the invention constitute further aspects of the present invention. As used herein, "polynucleotide" refers to a polymer of deoxyribonucleotides or ribonucleotides, in the form of a separate fragment or as a component of a larger construct, e. g. an expression vector such as a plasmid. Polynucleotide sequences of the invention include DNA, RNA and cDNA sequences. Due to the degeneracy of the genetic code, of course more than one polynucleotide is capable of encoding a particular peptide according to the invention. When a bacterial host is chosen for expression of a peptide, it may be necessary to take steps to protect the host from the expressed anti-bacterial peptide. Such techniques are known in the art and include the use of a bacterial strain which is resistant to the particular peptide being expressed or the expression of a fusion peptide with sections at one or both ends which disable the antibiotic activity of the peptide according to the invention. In the latter case, the peptide can be cleaved after harvesting to produce the active peptide. If the peptide incorporates a chemical modification then the activity/stability of the expressed peptide may be low, and is only modulated by post-synthetic chemical modification Furthermore, the invention also encompasses derivatives of the polypeptides of the invention. For example, but not by way of limitation, derivatives may include peptides or proteins that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, etc. Additionally, the derivative may contain one or more non-classical amino acids. Those skilled in the art will be aware of various methods for modifying peptides to increase potency, prolong activity and/or increase half-life. In one example (WO0210195) the modification is made via coupling through an amide bond with at least one conformationally rigid substituent, either at the N-terminal of the peptide, the C-terminal of the peptide, or on a free amino or carboxyl group along the peptide chain. Other examples of peptide modifications with similar effects are described, for example, in WO2004029081, WO03086444, WO03049684, WO0145746, WO0103723 and WO9101743.

The invention further provides antibodies that comprise a peptide or polypeptide of the invention or that mimic the activity of peptides or polypeptides of the invention. Such antibodies include, but are not limited to: polyclonal, monoclonal, bi-specific, multi-specific, human, humanized, chimeric antibodies, single chain antibodies, Fab fragments, F(ab')2 fragments, disulfide-linked Fvs, and fragments containing either a VL or VH domain or even a complementary determining region (CDR) that specifically binds to a polypeptide of the invention. In another embodiment, antibodies can also be generated using various phage display methods known in the art. Techniques to recombinantly produce Fab, Fab' and F(ab')2 fragments can also be employed using methods known in the art such as those disclosed in PCT publication WO 92/22324; Mullinax, et al., BioTechniques, 12(6):864-869, 1992; and Sawai, et al., 1995, AJRI 34:26-34; and Better, et al., 1988, Science 240:1041-1043 (each of which is incorporated by reference in its entirety). Examples of techniques that can be used to produce single-chain Fvs and antibodies include those described in U.S. Pat. Nos. 4,946,778 and 5,258,498; Huston, et al., 1991, Methods in Enzymology 203:46-88; Shu, et al., 1993, Proc. Natl. Acad. Sci. USA 90:7995-7999; and Skerra, et al., 1988, Science 240:1038-1040. For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. See, e.g., Morrison, 1985, Science 229:1202; Oi, et al., 1986, BioTechniques 4:214; Gillies, et al., 1989, J. Immunol. Methods 125:191-202; U.S. Pat. Nos. 5,807,715; 4,816,567; and 4,816,397; which are incorporated herein by reference in their entireties. Humanized antibodies are antibody molecules from non-human species that bind the desired antigen having one or more complementarity determining regions (CDRs) from the non-human species and framework regions from a human immunoglobulin molecule or in the case of the present invention, one or more CDRs derived from a TREM-1 protein. As known in the art, framework residues in the human framework regions can be substituted with the corresponding residue from the CDR donor antibody to alter, preferably improve, antigen binding. These framework substitutions are identified by methods well known in the art, e.g., by modelling of the interactions of the CDR and framework residues to identify framework residues important for antigen binding and sequence comparison to identify unusual framework residues at particular positions. See, e.g., Queen, et al., U.S. Pat. No. 5,585,089; Riechmann, et al., 1988, Nature 332:323, 1988, which are incorporated herein by reference in their entireties. Antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592,106; EP 519,596; Padlan, 1991, Molecular Immunology, 28(4/5):489-498; Studnicka, et al., 1994, Protein Engineering, 7(6):805-814; Roguska, et al., 1994, Proc Natl. Acad. Sci. USA 91:969-973, and chain shuffling (U.S. Pat. No. 5,565,332), all of which are hereby incorporated by reference in their entireties.

Completely human antibodies are particularly desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice (see Lonberg and Huszar (1995), Int. Rev. Immunol. 13:65-93). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598; which are incorporated by reference herein in their entireties. In addition, companies such as Abgenix, Inc. (Freemont, Calif.), Medarex (N.J.) and Genpharm (San Jose, Calif.) can be engaged to provide human antibodies directed against a selected antigen using technology similar to that described above. Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., 1988, Bio/technology 12:899-903). Antibodies fused or conjugated to heterologous polypeptides may be used in in vitro immunoassays and in purification methods (e.g., affinity chromatography) well known in the art. See, e.g., PCT publication Number WO 93/21232; EP 439,095; Naramura, et al., 1994, Immunol. Lett. 39:91-99; U.S. Pat. No. 5,474,981; Gillies, et al., 1992 Proc. Natl. Acad. Sci. USA 89:1428-1432; and Fell, et al., 1991, J. Immunol. 146:2446-2452, which are incorporated herein by reference in their entireties.

In another aspect, the present invention provides methods for identifying a compound or ligand that binds to or modulates the activity of a polypeptide of the invention. Such a method comprises measuring a biological activity of the polypeptide in the presence or absence of a test compound and identifying test compounds that alter (increase or decrease) the biological activity of the polypeptide.

In one embodiment, the invention provides a fusion protein comprising a bioactive molecule and one or more domains of a polypeptide of the invention or fragment thereof. In particular, the present invention provides fusion proteins comprising a bioactive molecule recombinantly fused or chemically conjugated (including both covalent and non-covalent conjugations) to one or more domains of a polypeptide of the invention or fragments thereof.

The present invention further encompasses fusion proteins in which the polypeptides of the invention or fragments thereof, are recombinantly fused or chemically conjugated (including both covalent and non-covalent conjugations) to heterologous polypeptides (i.e., an unrelated polypeptide or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences.

In one example, a fusion protein in which a polypeptide of the invention or a fragment thereof can be fused to sequences derived from various types of immunoglobulins. For example, a polypeptide of the invention can be fused to a constant region (e.g., hinge, CH2, and CH3 domains) of human IgG1 or IgM molecule, (for example, as described by Hudson & Souriauso (2003) Nature Medicine 9(1):129-134) so as to make the fused polypeptides or fragments thereof more soluble and stable in vivo. The short half-life of antibody fragments can also be extended by 'pegylation', that is, a fusion to polyethylene glycol (see Leong, S. R. et al. (2001) Cytokine 16:106-119). In one example of such fusions, described in WO0183525, Fc domains are fused with biologically active peptides. A pharmacologically active compound is produced by covalently linking an Fc domain to at least one amino acid of a selected peptide. Linkage to the vehicle increases the half-life of the peptide, which otherwise could be quickly degraded in vivo Alternatively, non-classical alternative protein scaffolds (for example see Nygren & Skerra (2004) J Immunol Methods 290(1-2):3-28 or WO03049684) can be used to incorporate, and replicate the properties of, the peptides of the invention, for example by inserting peptide sequences derived from TREM-1 CDR2 or CDR3 into a protein framework to support conformationally variable loops having structural/functional similarities to CDR2 or CDR3 in a fixed spatial arrangement Such fusion proteins or scaffold based proteins can be used as an immunogen for the production of specific antibodies which recognize the polypeptides of the invention or fragments thereof. In another preferred embodiment, such fusion proteins or scaffold based proteins can be administered to a subject so as to inhibit interactions between a ligand and its receptors in vivo. Such inhibition of the interaction will block or suppress certain cellular responses involved in sepsis and septic shock.

In one aspect, the fusion protein comprises a polypeptide of the invention which is fused to a heterologous signal sequence at its N-terminus. Various signal sequences are commercially available. For example, the secretory sequences of melittin and human placental alkaline phosphatase (Stratagene; La Jolla, Calif.) are available as eukaryotic heterologous signal sequences. As examples of prokaryotic heterologous signal sequences, the phoA secretory signal (Sambrook, et al., supra; and Current Protocols in Molecular Biology, 1992, Ausubel, et al., eds., John Wiley & Sons) and the protein A secretory signal (Pharmacia Biotech; Piscataway, N.J.) can be listed. Another example is the gp67 secretory sequence of the baculovirus envelope protein (Current Protocols in Molecular Biology, 1992, Ausubel, et al., eds., John Wiley & Sons).

In another embodiment, a polypeptide of the invention can be fused to tag sequences, e.g., a hexa-histidine peptide, such as the tag provided in a pQE vector (QIAGEN, Inc., 9259 Eton Avenue, Chatsworth, Calif., 91311), among others, many of which are commercially available. As described in Gentz, et al., 1989, Proc. Natl. Acad. Sci. USA 86:821-824, for instance, hexa-histidine provides for convenient purification of the fusion protein. Other examples of peptide tags are the hemagglutinin "HA" tag, which corresponds to an epitope derived from the influenza hemagglutinin protein (Wilson, et al., 1984, Cell 37:767) and the "flag" tag (Knappik, et al., 1994, Biotechniques 17(4):754-761). These tags are especially useful for purification of recombinantly produced polypeptides of the invention.

Fusion proteins can be produced by standard recombinant DNA techniques or by protein synthetic techniques, e.g., by use of a peptide synthesizer. For example, a nucleic acid molecule encoding a fusion protein can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, 1992, Ausubel, et al., eds., John Wiley & Sons). The nucleotide sequence coding for a fusion protein can be inserted into an appropriate expression vector, i.e., a vector which contains the necessary elements for the transcription and translation of the inserted protein-coding sequence. Various host-vector systems and selection systems are known. In a specific embodiment, the expression of a fusion protein is regulated by a constitutive promoter. In another embodiment, the expression of a fusion protein is regulated by an inducible promoter. In accordance with these embodiments, the promoter may be a tissue-specific promoter. Expression vectors containing inserts of a gene encoding a fusion protein can be identified by three general approaches: (a) nucleic acid hybridization, (b) presence or absence of "marker" gene functions, and (c) expression of inserted sequences. In the first approach, the presence of a gene encoding a fusion protein in an expression vector can be detected by nucleic acid hybridization using probes comprising sequences that are homologous to an inserted gene encoding the fusion protein. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding a fusion protein in the vector. For example, if the nucleotide sequence encoding the fusion protein is inserted within the marker gene sequence of the vector, recombinants containing the gene encoding the fusion protein insert can be identified by the absence of the marker gene function. In the third approach, recombinant expression vectors can be identified by assaying the gene product (i.e., fusion protein) expressed by the recombinant. Such assays can be based, for example, on the physical or functional properties of the fusion protein in in vitro assay systems, e.g., binding with anti-fusion protein antibody. For long-term, high-yield production of recombinant proteins, stable expression is preferred. For example, cell lines which stably express the fusion protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the differentially expressed or pathway gene protein. Such engineered cell lines may be particularly useful in screening and evaluation of compounds that affect the endogenous activity of the differentially expressed or pathway gene protein. Once a fusion protein of the invention has been produced by recombinant expression, it may be purified by any method known in the art for purification of a protein, for example, by chromatography (e.g., ion exchange, affinity, particularly by affinity for the specific antibody, and sizing column chromatography), centrifugation, differential solubility, or by any other standard technique for the purification of proteins.

The present invention also provides methods for treating a subject suffering from sepsis, septic shock or a sepsis-like condition by administering a peptide or polypeptide of the invention. In another embodiment, the modulator may be an antibody which mimics the activity of a polypeptide of the invention. In particular, the invention provides a method of treating or ameliorating sepsis, septic shock or a sepsis-like condition in a subject, comprising: administering a therapeutically effective amount of a peptide or polypeptide of any one of the preceding claims to a subject. In such methods, the peptide or polypeptide administered can have substantial sequence identity to sequence SEQ ID NOS: 3, 4, 6, 7, 16, 17, 18 or 19, is SEQ ID NOS: 3, 4, 6, 7, 16, 17, 18 or 19, or an active fragment, analogue or derivative of SEQ ID NOS: 3, 4, 6, 7, 16, 17, 18 or 19 or has at least about 80% sequence identity to SEQ ID NOS: 3, 4, 6, 7, 16, 17, 18 or 19

In one aspect, the invention provides a method for preventing sepsis, septic shock or sepsis-like conditions, by administering to the subject a peptide or polypeptide of the invention. Subjects at risk of sepsis or septic shock can be identified by, for example, any diagnostic or prognostic assays as known in the art (for particularly suitable methods of diagnosis, see WO2004081233, Gibot et al. (2004) Ann Intern Med. 141(1): 9-15 and Gibot et al. (2004) N Engl J Med. 350(5):451-8. The prophylactic agents described herein, for example, can be used to treat a subject at risk of developing disorders such as those previously discussed. The methods of the invention are applicable to mammals, for example humans, non human primates, sheep, pigs, cows, horses, goats, dogs, cats and rodents, such as mouse and rat. Generally, the methods of the invention are to be used with human subjects.

Furthermore, the invention provides a pharmaceutical composition comprising a polypeptide of the present invention or an antibody or fragments thereof that mimics a polypeptide of the invention. The peptides, polypeptides and antibodies (also referred to herein as "active compounds") of the invention can be incorporated into pharmaceutical compositions suitable for administration. Such compositions typically comprise the peptide, protein, or antibody and a pharmaceutically acceptable carrier.

As used herein the language "pharmaceutically acceptable diluent, carrier or excipient" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions containing a peptide or polypeptide of the invention. Such compositions can further include additional active agents. Thus, the invention further includes methods for preparing a pharmaceutical composition by formulating a pharmaceutically acceptable carrier with a peptide or polypeptide of the invention and one or more additional active compounds.

A pharmaceutical composition of the invention is formulated to be compatible with its intended route of administration. Examples of routes of administration include parenteral, e.g., intravenous, intradermal, subcutaneous, transdermal (topical), transmucosal, intra-articular, intraperitoneal, and intrapleural, as well as oral, inhalation, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy injectability with a syringe exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient, such as starch or lactose; a disintegrating agent, such as alginic acid, Primogel, or corn starch; a lubricant, such as magnesium stearate or Sterotes; a glidant, such as colloidal silicon dioxide; a sweetening agent, such as sucrose or saccharin; or a flavoring agent, such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank, et al., 1997, J. Acquired Immune Deficiency Syndromes and Human Retrovirology 14:193).

The pharmaceutical compositions can be included in a container, pack, or dispenser together with instructions for administration.

The invention further provides a kit containing a peptide or polypeptide of the invention of the present invention, or an antibody or fragments thereof mimicking a polypeptide of the invention, preferably with instructions for use, for example in the treatment of sepsis, septic shock or sepsis-like conditions.

The invention provides a method for identifying (or screening) modulators, i.e., candidate or test compounds or agents (e.g., peptides, peptidomimetics, small molecules or other drugs) which mimic a polypeptide of the invention or have a stimulatory or inhibitory effect on, for example, activity of a polypeptide of the invention. In particular, the invention provides a method of screening compounds or compositions to treat sepsis, septic shock or sepsis-like conditions, comprising: providing a TREM-1 peptide; contacting an animal in a cecal ligation and puncture model (or using other assay or model as described herein or known in the art) with the TREM-1 peptide; determining if there was a modulation in the sepsis, for example wherein an increase in survival indicates that the TREM-1 peptide may be useful for treating sepsis, septic shock or sepsis-like conditions.

The invention further pertains to novel agents identified by the above-described screening assays and uses thereof for treatments as described herein.

All publications, including but not limited to patents and patent applications, cited in this specification are herein incorporated by reference as if each individual publication were specifically and individually indicated to be incorporated by reference herein as though fully set forth.

Preferred features of each aspect of the invention are applicable to each other aspect, *mutatis mutandis*.

The present invention will now be described with reference to the following non-limiting examples, with reference to the figures, in which:

FIG. 1A. shows a sequence alignment of TREM-1 and TREM-2 family members. Human TREM-1 (SEQ ID NO:1) was aligned with mouse TREM-1 (SEQ ID NO:2) and human and mouse TREM-2 (SEQ ID NO:26 and 27, respectively in order of appearance) using version 1.74 of CLUSTAL W. Secondary structure assignments correspond to the published human TREM-1 structure (arrows for β-strands and cylinder for α helices) (Radaev et al. (2003) Structure (Camb). December; 11(12):1527-35). Residues involved in homo-heterodimer formation are shown in white on black background. Cysteine making disulfide bonds conserved for V-type Ig fold are in bold. Gaps are indicated with (−), identical residues with (*), similar with (: or .). An extended region of similarities between human and mouse TREM1 sequences is shown in boxes on grey background. TREM-1 peptide sequences used in the Examples herein are indicated underlined.

FIG. 1B. shows a ribbon diagram of the published TREM-1 homodimeric structure (Kelker, et al. (2004) J Mol Biol. September 24; 342(4):1237-48). Postulated binding sites that comprise the antibody equivalent Complementarity Determining Regions (CDRs) are in red.

FIG. 2. shows that administration of TREM-1 peptides, 1 hour before LPS, reduces death induced by endotoxaemia. BALB/c mice (10 per group) were injected intraperitoneally with 200 μg LPS. The TREM-1 peptides P1, P2, P3, or P5 (200 μl of a 300 μM solution per mouse) were injected intraperitoneally 1 hour before LPS. Viability of mice was monitored twice a day for 7 days. Statistical analysis was performed by Logrank test. Data from control mice represent cumulative survival curves from two independent experiments performed under identical conditions.

Figure 3:
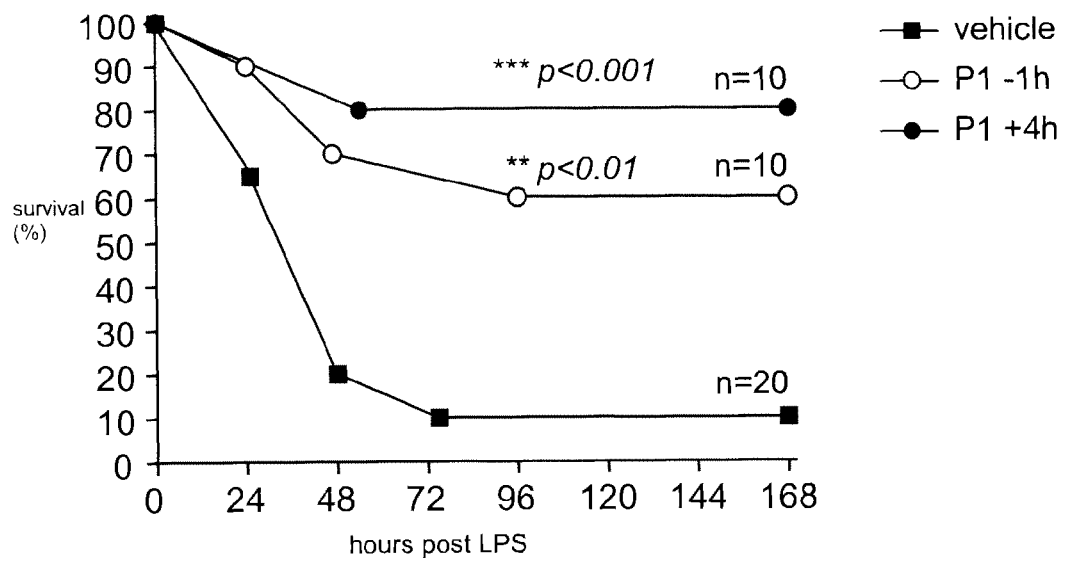

FIG. 3. shows that TREM-1 peptide P1 is able to effectively reduce death induced by endotoxaemia when injected at 4 hours after LPS. BALB/c mice (10 per group) were injected intraperitoneally with 200 μg LPS. TREM-1 peptide P1, 200 μl of a 300 μM solution per mouse was injected intraperitoneally 1 hour before or 4 hours after LPS. Viability of mice was monitored twice a day for 7 days. Statistical analysis was performed with the Logrank test. Data from control mice represent cumulative survival curves from two independent experiments performed under identical conditions FIG. 4. shows that administration of TREM-1 peptides, 4 hours after LPS, reduces death induced by endotoxaemia. BALB/c mice (10 per group) were injected intraperitoneally with 200 μmg LPS. P1 peptide, 200 μl of a 150, 300 and 600 μM solution per mouse (dots) or P3, 200 μl of a 600 μM solution per mouse (filled squares) were injected intraperitoneally 4 hours after LPS. Viability of mice was monitored twice a day for 7 days. Statistical analysis was performed with the Logrank test FIG. 5. shows that TREM-1 peptide P1 protects against cecal ligation and puncture (CLP). CLP was induced in C57BL/6 mice (15 per group) as described in Materials and Methods. P1 peptide (empty dots) or P3 peptide (filled squares) (200 μl of a 600 μM solution per mouse) were injected intraperitoneally 5 and 24 hours after CLP induction. Viability of mice was monitored twice a day for 10 days. Statistical analysis was performed with the Logrank test.

Figure 6:
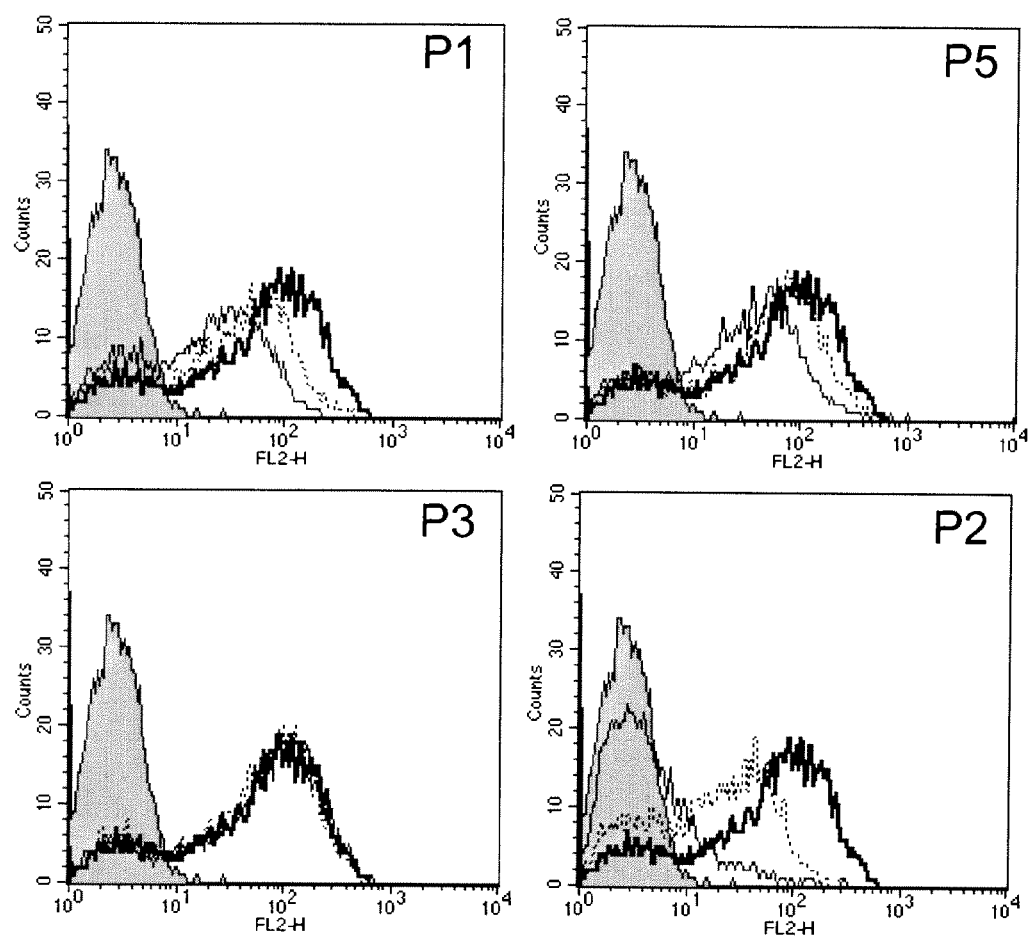

FIG. 6. shows that P1, P2 and P5 peptides, but not P3 peptide, inhibit the binding of soluble TREM-1/IgG1 to TREM-1 Ligand positive peritoneal exudate cells. Cytofluorimetric analysis of peritoneal exudate cells with 2 μg/ml of mouseTREM-1/hIgG1 in the presence of a 500 μM solution per mouse (thin line), 100 μM solution per mouse (dotted line) or absence (thick line) of the peptides is shown. The grey histogram represents immunostaining with human IgG1 as a control.

FIG. 7A. shows the release of sTREM-1 from cultured monocytes after stimulation with LPS with and without proteases inhibitor. LPS stimulation induced the appearance of a 27-kD protein that was specifically recognized by an anti-TREM-1 mAb (inset). sTREM-1 levels in the conditioned culture medium were measured by reflectance of immunodots. Data are shown as mean±SD (n=3).

FIG. 7B. shows expression of TREM-1 mRNA in monocytes. Cultured monocytes were stimulated with LPS (1 μg/mL) for 0, 1 and 16 hours as indicated. LPS induced TREM-1 mRNA production within 1 hour.

Figure 8A:
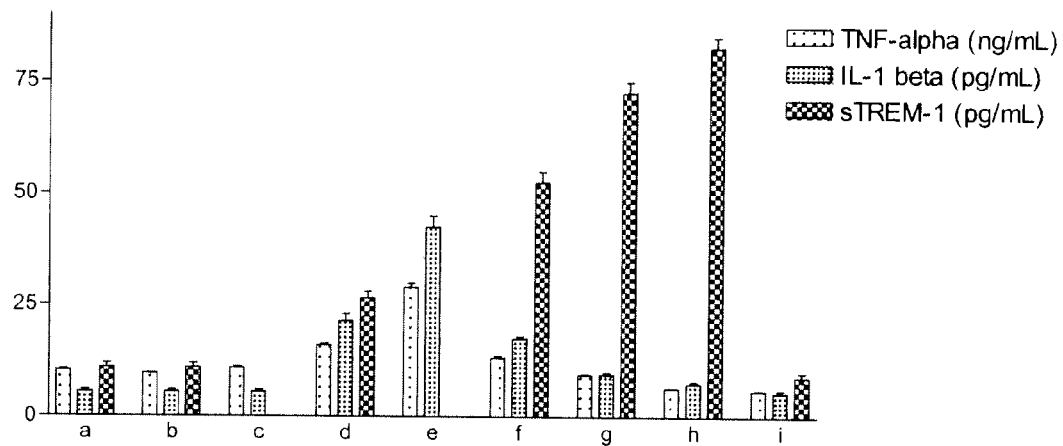

FIG. 8A. shows the release of cytokines and sTREM-1 from cultured monocytes. For cell activation, primary monocytes were cultured in 24-well flat-bottom tissue culture plates in the presence of LPS (1 μg/mL). In some experiments this stimulus was provided in combination with P5 (10 to 100 ng/mL), control peptide (10 to 100 ng/mL) or rIL-10 (500 U/mL). To activate monocytes through TREM-1, an agonist anti-TREM-1 mAb (10 μg/mL) was added as indicated. Cell-free supernatants were analysed for production of TNF-α, IL-1β and sTREM-1 by ELISA or immunodot. All experiments were performed in triplicate and data are expressed as means (SEM).

a: Media
    b: P5 10 ng/mL
    c: Anti-TREM-1
    d: LPS
    e: LPS+Anti-TREM-1
    f: LPS+P5 10 ng/mL
    g: LPS+P5 50 ng/mL
    h: LPS+P5 100 ng/mL
    i: LPS+IL10

Figure 8B:
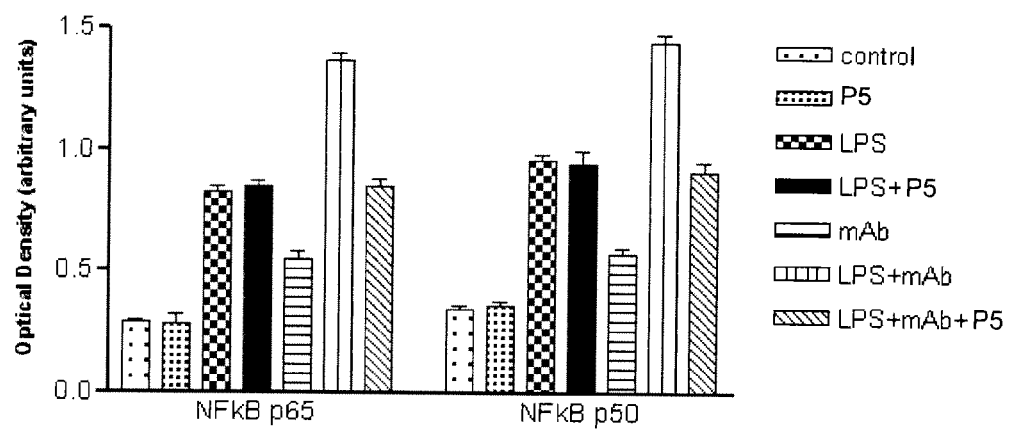

FIG. 8B. shows the effect of P5 on NFκKB activation. Monocytes were cultured for 24 hours in the presence of *E.coli* LPS (O111:B4, 1 μg/mL), anti-TREM-1 mAb (10 μg/mL) and/or P5 (100 ng/mL) as indicated and the levels of NFκB p50 and p65 were determined using an ELISA-based assay. Experiments were performed in triplicate and data are expressed as means of optical densities (SEM).

Figure 9:
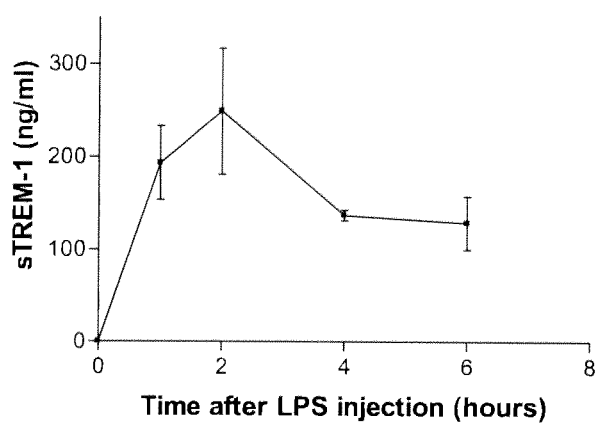

FIG. 9. shows accumulation of sTREM-1 in serum of LPS-treated mice. Male Balb/C mice (20 to 23 g) were treated with LPS ($LD_{50}$, intraperitoneally). Serum was assayed for sTREM-1 by immunodot. Serum sTREM-1 was readily detectable 1 hour after LPS administration and was maintained at a plateau level from 4 to 6 hours.

Figure 10A:
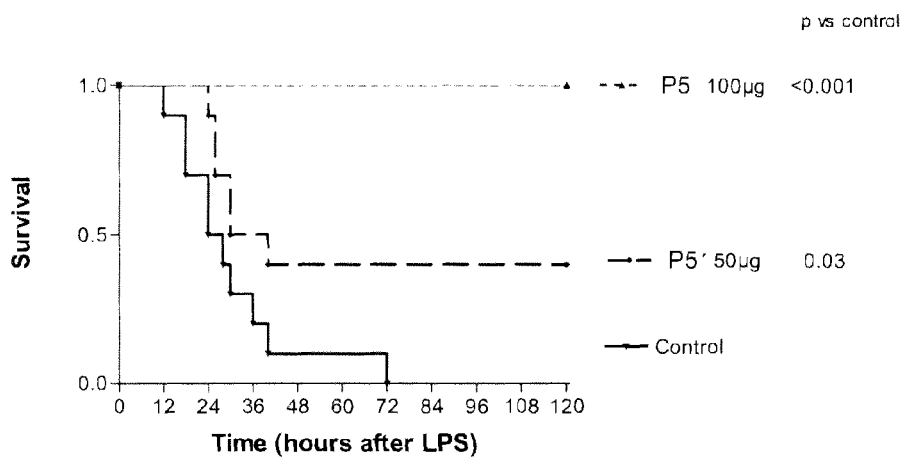

FIG. 10A. shows that P5 pre-treatment protects against LPS lethality in mice. Male Balb/C mice (20 to 23 g) were randomly grouped (10 mice per group) and treated with an $LD_{100}$ of LPS. P5 (50 μg or 100 μg) or control vector was administered 60 min before LPS.

Figure 10B:
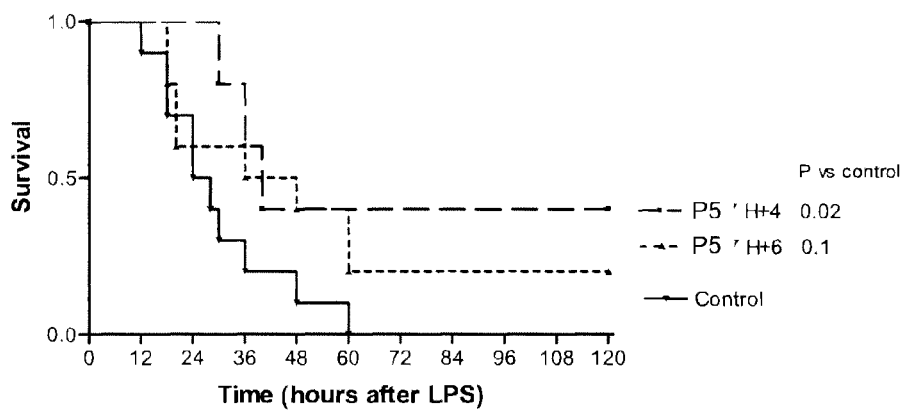

FIG. 10B. shows that delayed administration of P5 protects LPS lethality in mice. Male Balb/C mice (20 to 23 g) were randomly grouped (8 mice per group) and treated with an $LD_{100}$ of LPS. P5 (75 μg) or control vector was administered 4 or 6 hours after LPS as indicated.

Figure 10C:
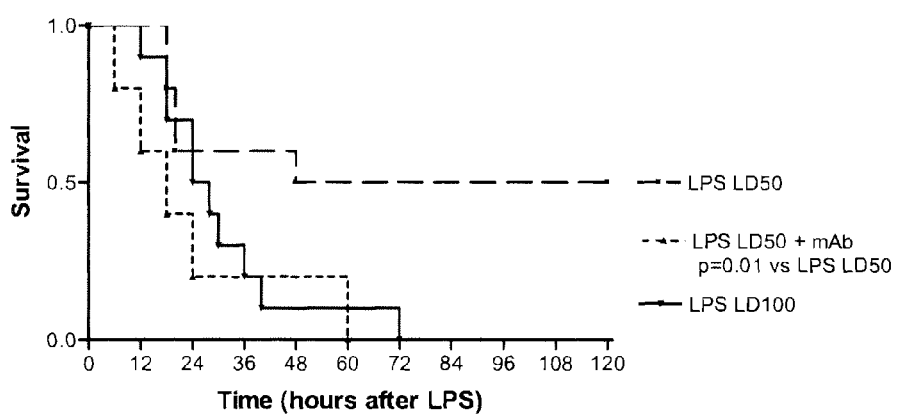

FIG. 10C. shows that administration of agonist TREM-1 mAb is lethal to mice. Male Balb/C mice (20 to 23 g) were randomly grouped (8 mice per group) and treated with a combination of an $LD_{50}$ of LPS+control vector, $LD_{50}$ of LPS+anti-TREM-1 mAb (5 μg) or $LD_{100}$ of LPS+control vector as indicated. Control vector and anti-TREM-1 mAb were administered 1 hour after LPS injection FIG. 11A. shows that P5 partially protects mice from CLP-induced lethality. Male Balb/C mice (20 to 23 g) were randomly grouped and treated with normal saline (n=14) or the control peptide (n=14, 100 µg) or with P5 (100 µg) in a single infection at H0 (n=18), H+4 (n=18) or H+24 (n=18). The last group of mice (n=18) was treated with repeated injections of P5 (100 µg) at H+4, H+8 and H+24.

Figure 11A:
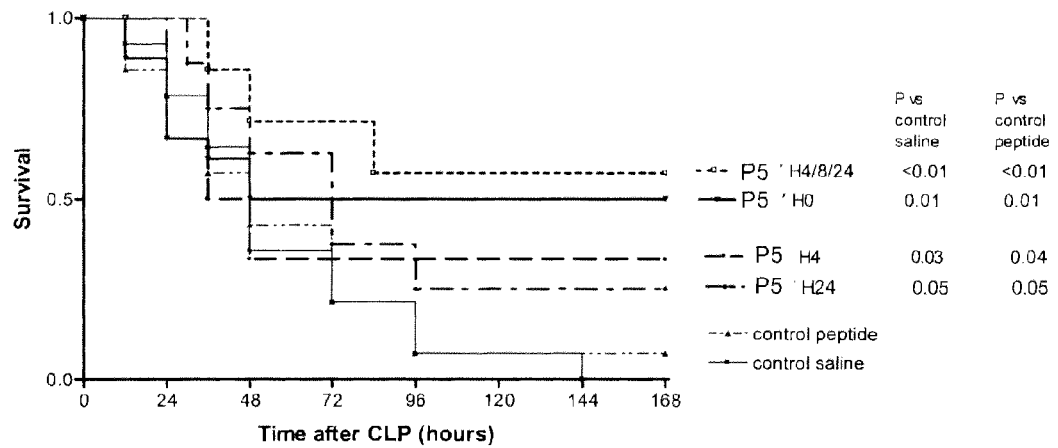
Figure 11B:
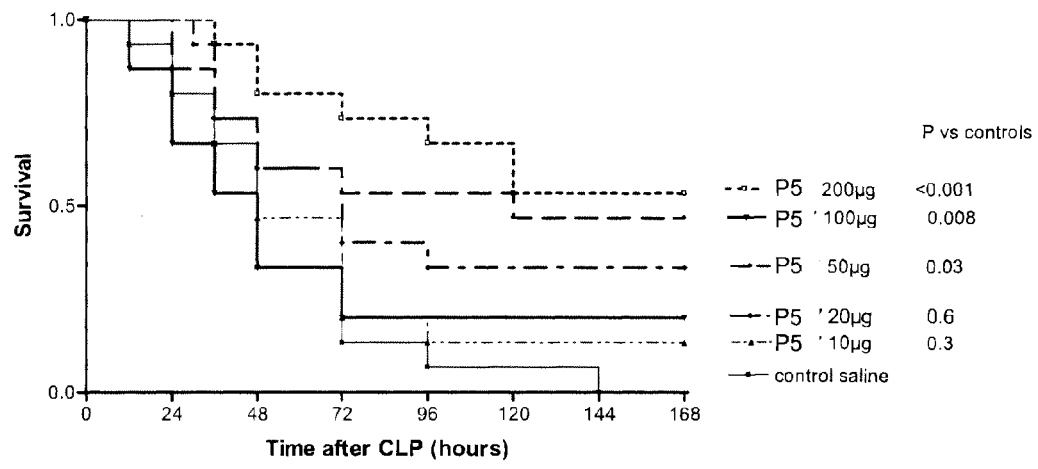

FIG. 11B. shows the dose effect of P5 on survival. Mice (n=15 per group) were treated with a single injection of normal saline or 10 µg, 20 µg, 50 µg 100 µg or 200 µg of P5 at H0 after the CLP and monitored for survival FIG. 12. shows that P5 has no effect on bacterial counts during CLP. Mice (5 per group) were killed under anaesthesia at 24 hours after CLP. Bacterial counts in peritoneal lavage fluid and blood were determined and results are expressed as CFU per mL of blood and CFU per mouse for the peritoneal lavage.

Figure 13A:
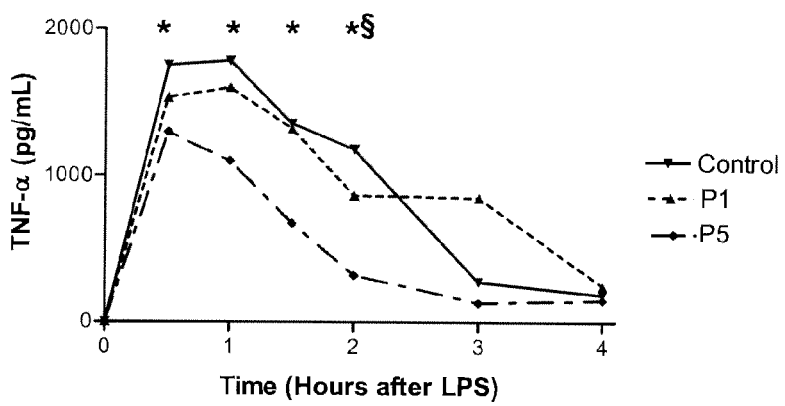
Figure 13B:
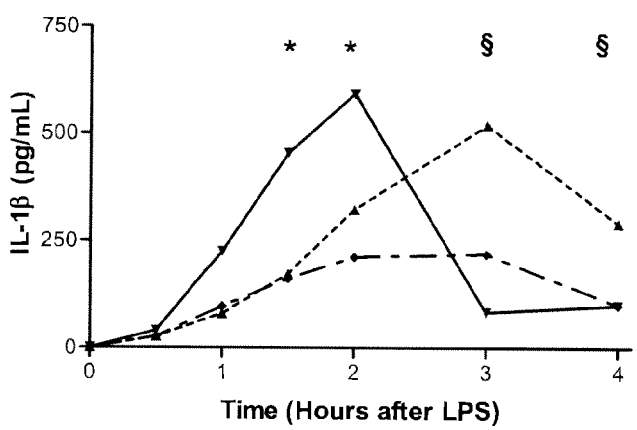
Figure 14:
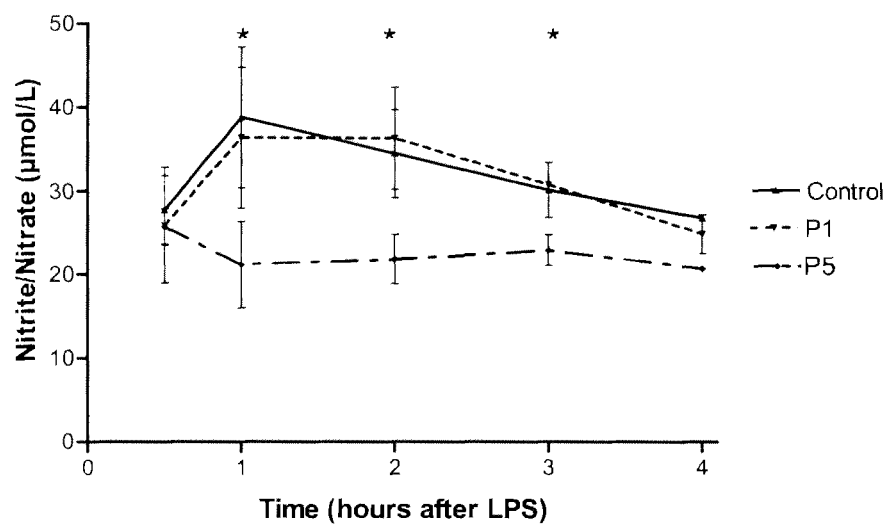
Figure 15:
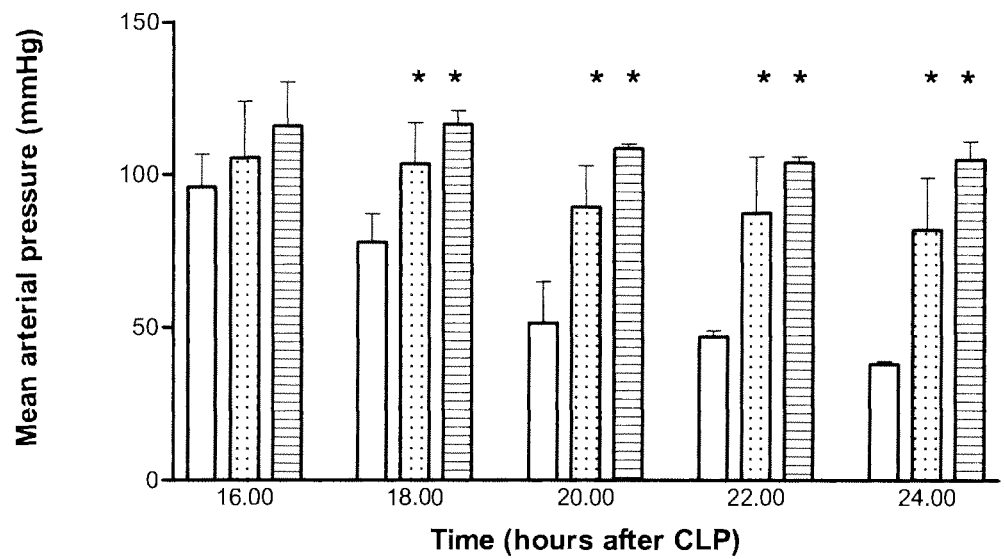
Figure 16:
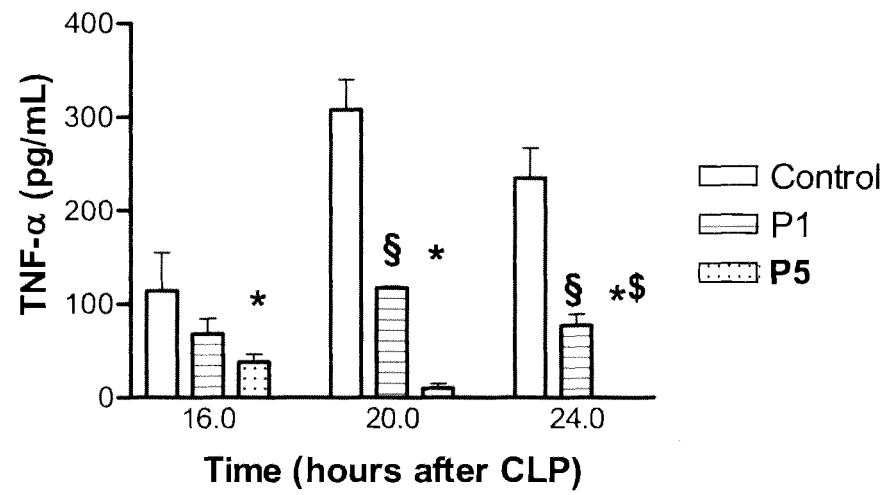
Figure 17:
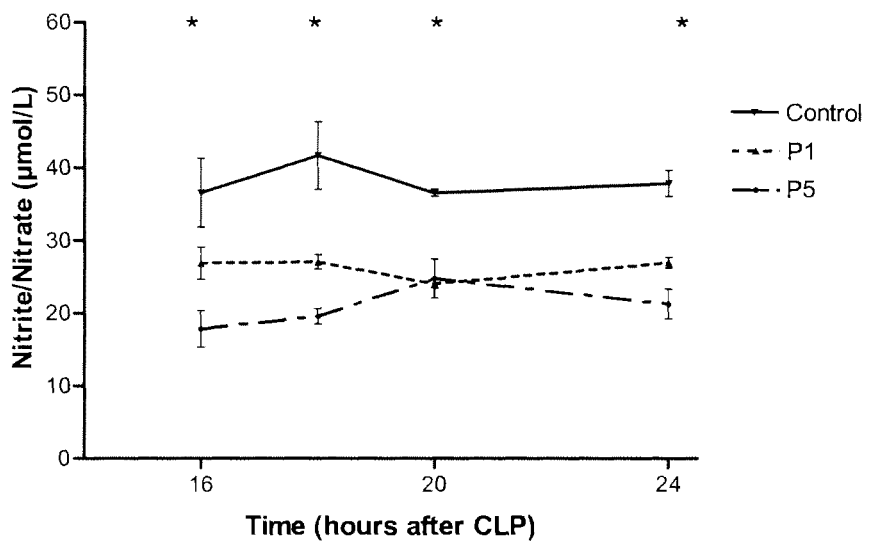
Figure 18:
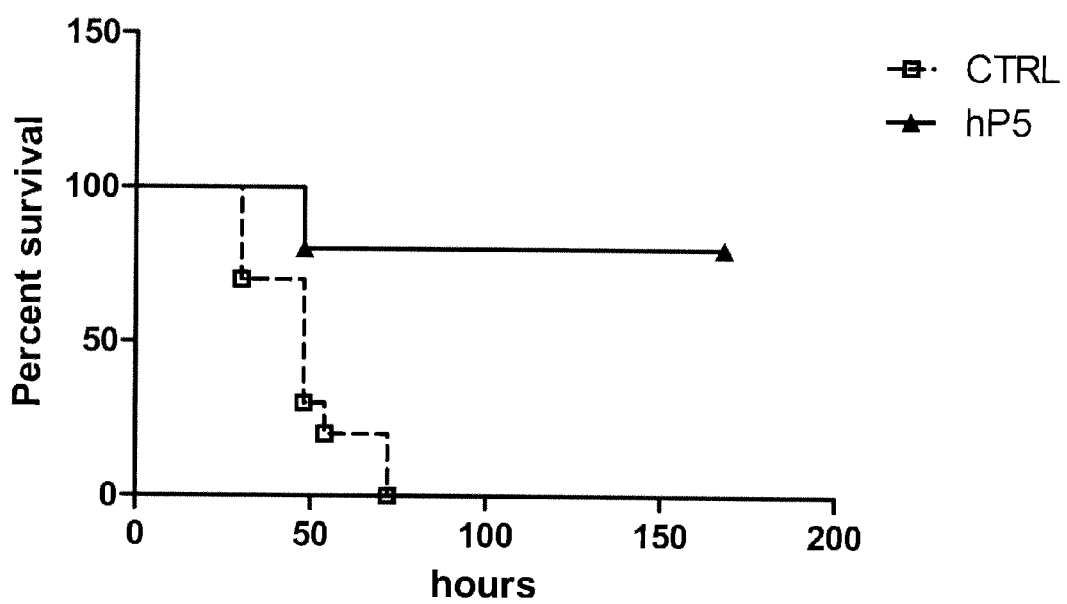

FIG. 13 shows TNF-α and IL-1β plasma concentration evolution after LPS (15 mg/kg) administration in rats.
*$p<0.05$ P5-treated vs Control animals
§$p<0.05$ P5-treated vs P1-treated animals FIG. 14 shows Nitrite/Nitrate concentrations evolution after LPS (15 mg/kg) administration in rats. *$p<0.05$ P5-treated vs Control and P1-treated animals FIG. 15 shows mean arterial pressure evolution during caecal ligation and puncture-induced peritonitis in rats.
*$p<0.05$ vs Control animals FIG. 16 shows TNF-α plasma concentration evolution during caecal ligation and puncture-induced peritonitis in rats.
*$p<0.05$ P5-treated vs Control animals
§$p<0.05$ P1-treated vs Control animals
$$p<0.05$ P5 vs P1-treated animals FIG. 17 shows Nitrite/Nitrate concentration evolution during caecal ligation and puncture-induced peritonitis in rats.
*$p<0.05$ P5 and P1-treated vs Control animals FIG. 18 shows that hP5 efficiently protects mice from LPS induced septic shock (see Example 5). Septic shock was induced in male Balb/c mice (n=15/group) with 200 mg of LPS as described in Material and Methods. hP5 peptide or control were administered at the following time points: −1 h, 0 h, +1 h+4 h. Mortality was followed twice a day for 7 days. Data were analysed using GraphPad Prism Survival curve analysis. Log-rank (Mantel-Cox) test showed a statistically significant difference between the two curves (p=0.0003).

Figure 19:
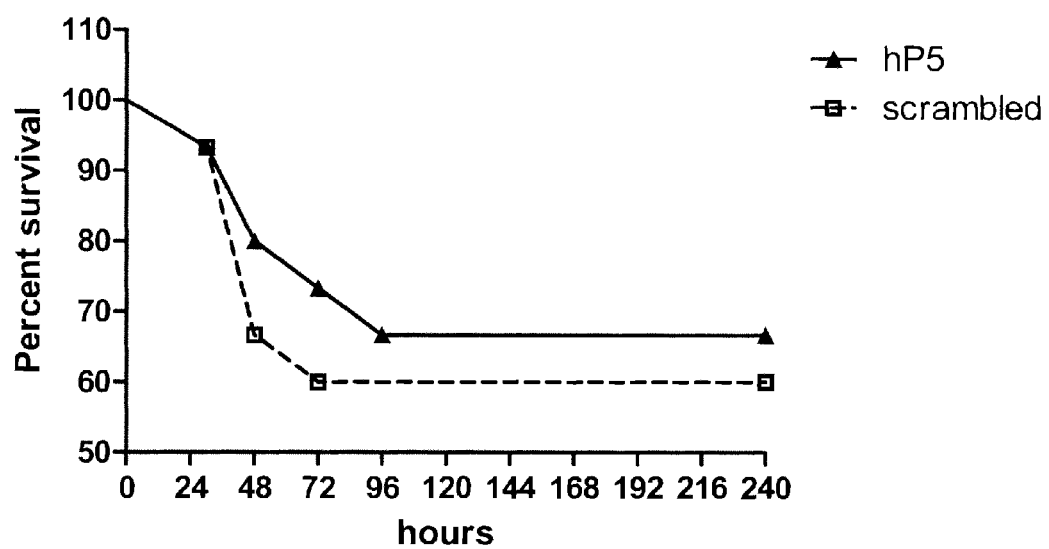

FIG. 19. shows the results for male C57BL/6 mice (n=15/group) that were subject to Cecal Ligation and Puncture as described in Example 6 and treated with hP5 peptide or scrambled peptide control at the following time points: −1 h, 0 h, +4 h and +24 h. Mortality was followed twice a day for 10 days. Data were analyzed using GraphPad Prism Survival curve analysis.

Figure 20:
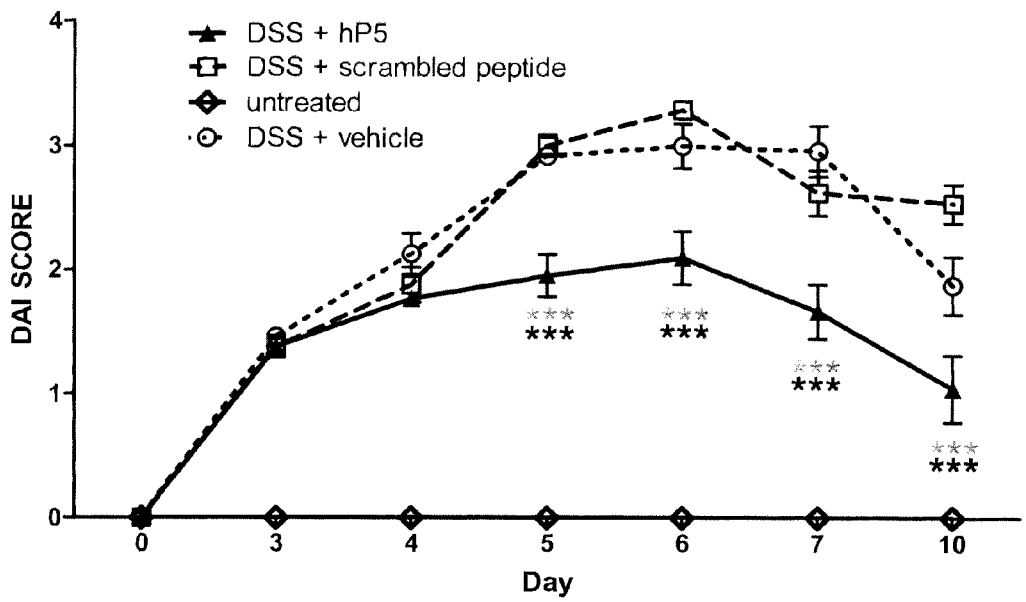

FIG. 20. Disease Activity Index (DAI). Colitis was induced by oral administration of DSS (see Example 7). Upon colitis induction, mice (n=8) were daily treated either with hP5 or its scrambled control peptide. Animal weight, haemoccult or presence of gross blood and stool consistency were used to determine the DAI score as indicated in Example 7. *(grey)=DSS+hP5 versus DSS+scrambled peptide; *(black)=DSS+hP5 vs DSS+vehicle; *$p≤0.001$, $p≤0.01$, *$p≤0.05$.

Figure 21:
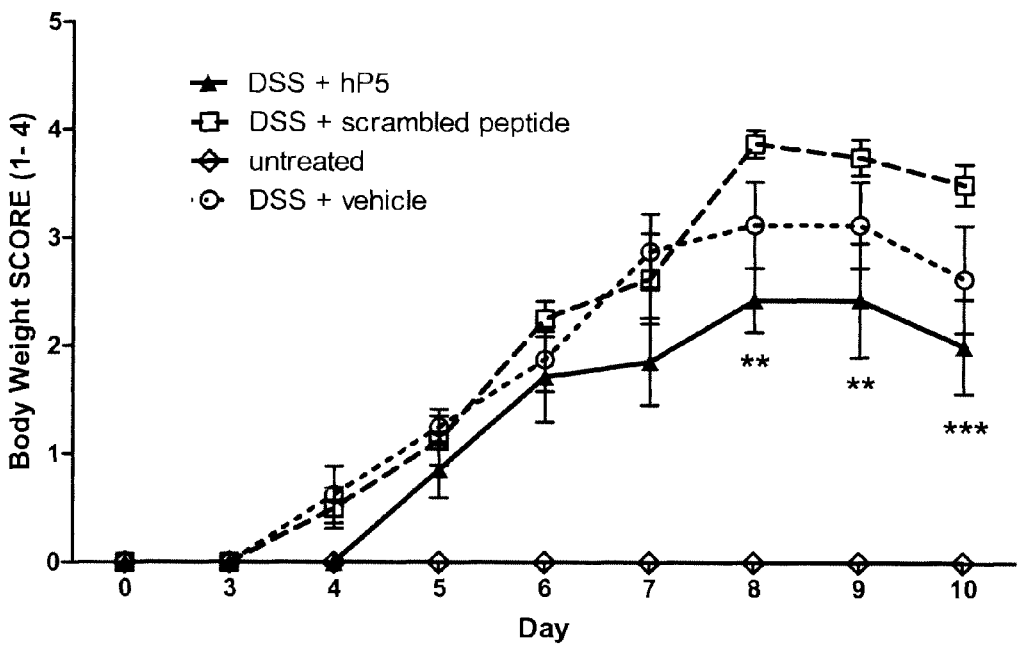

FIG. 21. Body weight loss. Colitis was induced by oral administration of DSS (see Example 7). Upon colitis induction, mice were daily treated either with hP5 or its scrambled control peptide. Weight was daily measured and percentage of weight loss versus day 0 was calculated. *(grey)=DSS+hP5 versus DSS+scrambled peptide; *(black)=DSS+hP5 vs DSS+vehicle; *$p≤0.001$, $p≤0.01$.

Figure 22:
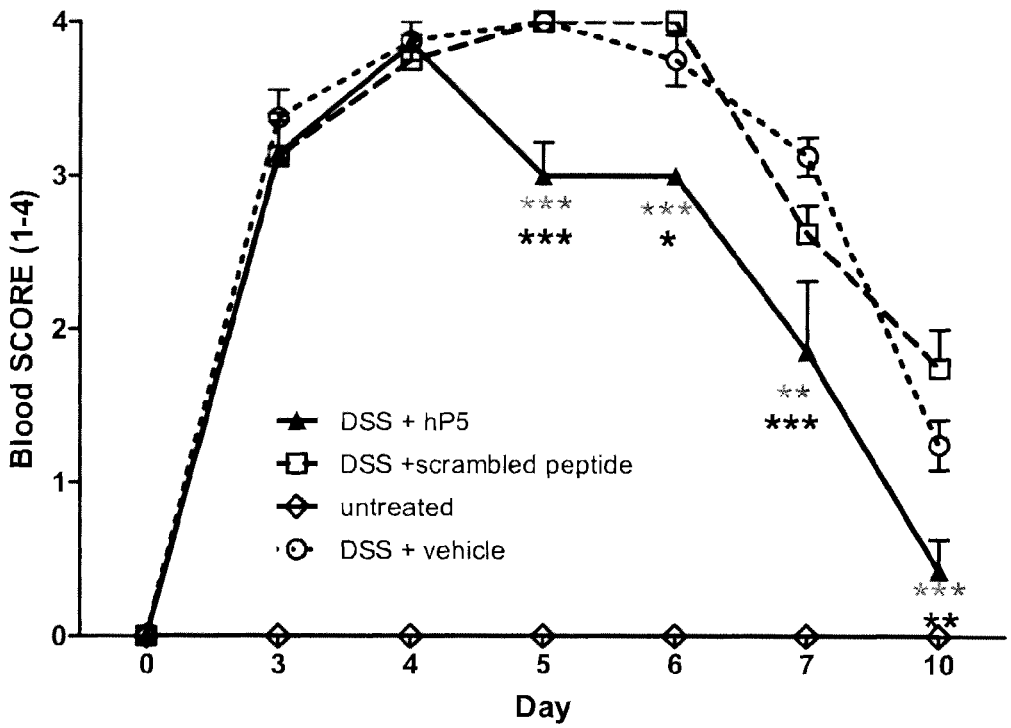

FIG. 22. Haemoccult or presence of gross blood in the feces. Colitis was induced by oral administration of DSS (see Example 7). Upon colitis induction, mice were daily treated either with hP5 or its scrambled control peptide. Haemoccult or presence of gross blood was detected and score assigned as measured and score assigned at the indicated time points as described in. Example 7. *(grey)=DSS+hP5 versus DSS+scrambled peptide; *(black)=DSS+hP5 vs DSS+vehicle; *$p≤0.001$, $p≤0.01$, *$p≤0.05$.

Figure 23:
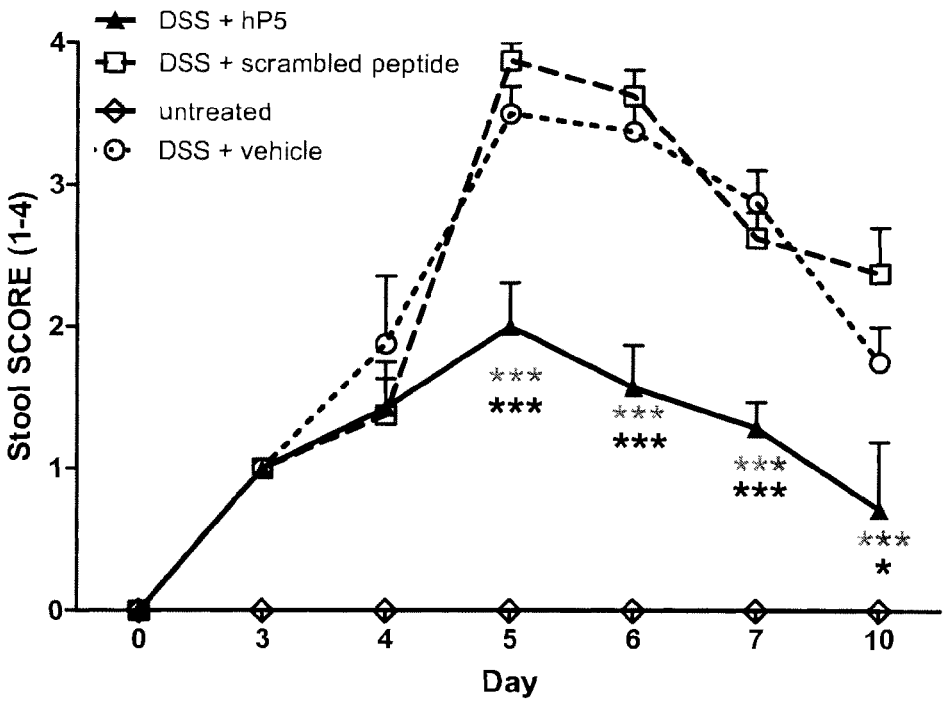

FIG. 23. Extent of diarrhea. Colitis was induced by oral administration of DSS (see Example 7). Upon colitis induction, mice were daily treated either with hP5 or its scrambled control peptide. Stool consistency was measured and score assigned at the indicated time points as described in Example 7. *(grey)=DSS+hP5 versus DSS+scrambled peptide; *(black)=DSS+hP5 vs DSS+vehicle; *$p≤0.001$, $p≤0.01$, *$p≤0.05$.

Figure 24:
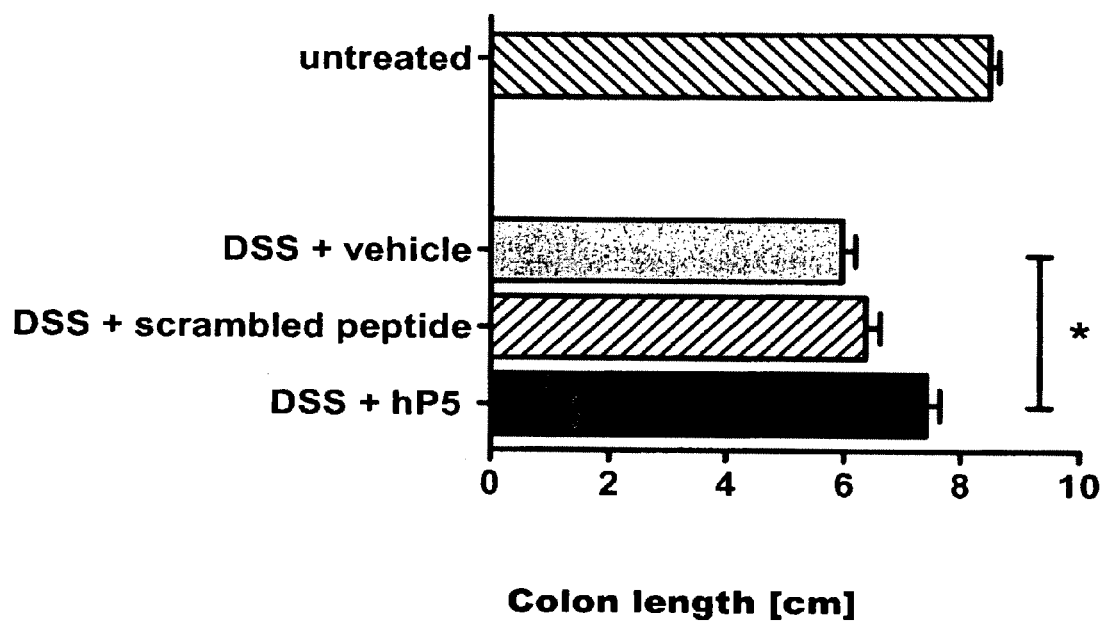

FIG. 24. Shortening of the colon. Colitis was induced by oral administration of DSS (see Example 7). Upon colitis induction, mice were daily treated either with hP5 or its scrambled control peptide. At day 11 mice were euthanized and the colon length of each mouse measured from the anus to the end of the cecum. *$p≤0.001$, $p≤0.01$, *$p≤0.05$.

EXAMPLE 1

TREM-1 Peptides Protect Mice from Death by Septic Shock

TREM-1 peptides matching the following criteria were synthesized: i) highest homology between human and mouse TREM-1 and lowest homology with TREM-2. ii) peptides spanning the Complementarity Determining Regions (CDRs) of TREM-1. According to the published crystal structure of TREM-1, and in analogy with antibodies, these residues are likely to be involved in cognate ligand recognition (Radaev et al. (2003) Structure (Camb). December; 11(12): 1527-35 & Kelker, et al. (2004) J Mol Biol. September 24; 342(4):1237-48) (see FIG. 1). One peptide (P1) was designed in the CDR2 region and three peptides (P2, P4 and P5) in the CDR3 region. A fourth peptide (P3) was designed in the neck region connecting the V-type immunoglobulin OM-like domain (Ig-V) to the trans-membrane domain. No peptide was designed in the CDR1 region due to high sequence homology between TREM-1 and TREM-2.

Thus, the following peptides of the TREM-1 protein were ordered from and were synthesized and purified by the Protein and Peptide Chemistry Facility, Institute of Biochemistry, University of Lausanne:

```
P1 (CDR2 67-89)
LVVTQRPFTRPSEVHMGKFTLKH        [SEQ ID NO: 3]

P2 (CDR3 114-136)
VIYHPPNDPVVLFHPVRLVVTKG        [SEQ ID NO: 4]

P3 (neck region 168-184)
TTTRSLPKPTAVVSSPG              [SEQ ID NO: 5]

P4 (CDR3 103-123)
LQVTDSGLYRCVIYHPPNDPV          [SEQ ID NO: 6]

P5 (CDR3 103-119):
LQVTDSGLYRCVIYHPP              [SEQ ID NO: 7]
```

-continued

```
P1sc* (P1 scrambled seq.)
LTPKHGQRSTHVTKFRVFEPVML        [SEQ ID NO: 8]

P5sc* (P5 scrambled seq.)
TDSRCVIGLYHPPLQVY              [SEQ ID NO: 9]
*This is a control peptide and indeed does
not protect
```

In the experiments of this example, the peptides were administered in a volume of 200 µl of the solution molarity indicated. To assess the ability of TREM1-peptides to protect mice from LPS-induced endotoxaemia, the Inventors administered peptides P1, P2, P3 and P5 (300 µM) 1 hour before a lethal dose of lipopolysaccharide (LPS) (FIG. 2). Lethality was monitored over time and compared with animals that had received control injections of vehicle alone. P5 injection confers maximal protection, with 90% of the animals still alive 7 days after LPS injection, as compared with 10% of control mice ($p<0.001$). 60% of the P1-treated mice and 50% of the P2 treated mice survived endotoxaemia as compared with 10% of control mice ($p<0.01$ and $p<0.05$ respectively). Interestingly, all P3-treated mice died within 4 days after LPS injection. These results indicate that peptides containing sequences of the extracellular portion of TREM-1 corresponding to the putative ligand binding site (CDR2 and CDR3) can protect mice from lethal shock.

Figure 4:
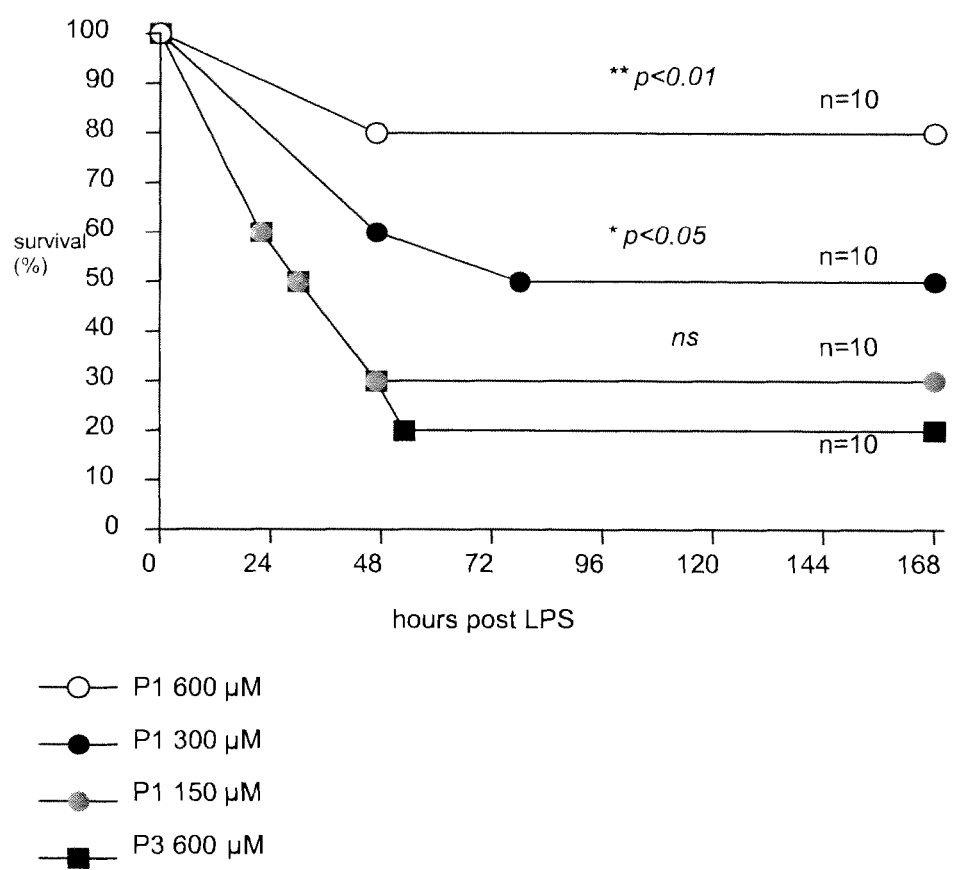
Figure 5:
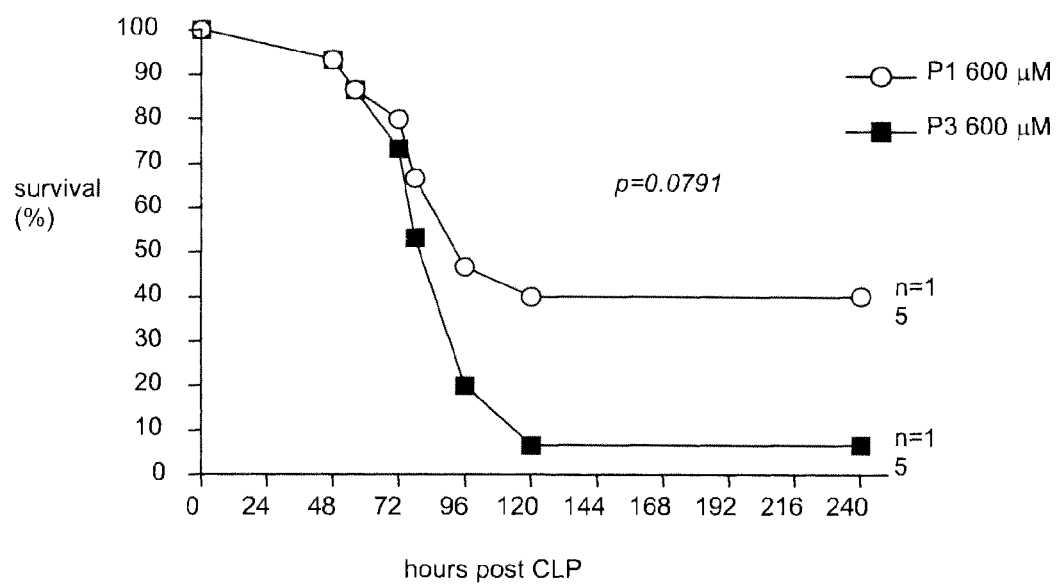

In order to investigate whether TREM-1 peptide treatment could be delayed until after the administration of LPS, the Inventors injected the peptides at 4 hours after LPS injection. Only in the case of P1, this delayed treatment conferred significant protection against a lethal dose of LPS (FIG. 3). 80% of the mice injected with P1 4 hours after LPS survived endotoxaemia compared to 60% of mice treated 1 h before LPS and 10% of mice treated with vehicle alone ($p<0.001$ and $p<0.01$ respectively). Thus, P1 is effective even when injected after the outbreak of endotoxaemia. No late death occurred over one week, indicating that P1 did not merely delay the onset of LPS lethality, but provided lasting protection. P1 administration conferred maximal protection (80%) when administered at 600 µM ($p<0.01$) and the level of protection dropped to 50% at 300 µM ($p<0.05$) and further down to 30% at 150 µM as compared to 20% of control mice, indicating a dose dependent effect of P1 (FIG. 4). The Inventors then investigated whether P1 protects against septic shock in the "CLP" model (Cecal Ligation and Puncture is a widely used experimental model of sepsis). Mice treated with two doses of P1 at 5 and 24 hours after CLP were protected from death as compared to control treated mice ($p=0.0791$) although the difference was not statistically significant. 40% of the mice injected with P1 at 5 days after CLP survived compared to 5% of mice treated with P3 peptide. At 10 days after CLP, the treated mice were still alive, indicating that P1 did not merely delay mortality, but provided lasting protection (FIG. 5).

EXAMPLE 2

TREM-1 Peptide P1 Inhibits Binding of Soluble Mouse TREM-1/IgG to TREM-1 Ligand Positive Cells Among TREM-1 derived peptides tested in CLP, peptides P1, P2 and P5 demonstrate a protective activity. A possible mechanism of action could be the ability of TREM-1 derived peptide to interfere with TREM-1/TREM-1 ligand interaction. To address this question the Inventors performed competition experiments on TREM-1 ligand positive cells: PEC (Peritoneal Exudate Cells) from CLP treated mice.

Peritoneal exudate cells (PEC) from mice suffering from a caecal ligation and puncture (CLP)-induced peritonitis were subjected to flow cytometry analysis after incubation with a PE-conjugated anti-human IgG1 (Jackson Immunoresearch, Bar Harbor, USA). Competition with TREM-1 peptides was performed by pre-incubating cells with the indicated concentrations of peptides for 45 minutes on ice before adding mTREM-1-IgG1.

As shown in FIG. 6, the P1 peptide, derived from the CDR2 region of mTREM-1, and the P2 and P5 peptides spanning the CDR3 region inhibit TREM-1 interaction with its ligand in a dose dependent manner. Conversely the P3 peptide, derived from the neck region of TREM-1 connecting the IgG like portion to the transmembrane domain was ineffective.

EXAMPLE 3

Additional Studies on the Modulation of the Inflammatory Response in Murine Sepsis by TREM-1 Peptide P5

Methods

Preparation of Monocytes from Peripheral Blood

Ten mL of peripheral blood samples were collected on EDTA-K from 5 healthy volunteer donors originating from laboratory staff. After dilution in RPMI (Life Technologies, Grand Island, N.Y.) v/v, blood was centrifuged for 30 min at room temperature over a Ficoll gradient (Amersham Pharmacia, Uppsala, Sweden) to isolate PBMC. The cells recovered above the gradient were washed and counted. In order to deplete the suspensions of lymphocytes, cells were then plated in 24-well flat-bottom tissue culture plates (Corning, Corning, N.Y.) at a concentration of $5 \times 10^6$/mL and allowed to adhere during 2 hours at 37° C. The resulting lymphocyte suspension was discarded and the adhering monocytic cells were maintained in a 5% CO2 incubator at 37° C. in complete medium (RPMI 1640, 0.1 mM sodium pyruvate, 2 mM Penicillin, 50 µg/mL Streptomycin; Life Technologies) supplemented with 10% FCS (Invitrogen, Cergy, France).

TREM-1 Peptide

Using the human TREM-1 sequence in Gen-Bank, accession #AF287008 and the mouse TREM-1 sequence #AF241219, a peptide "P5" (LQVTDSGLYRCVIYHPP; [SEQ ID NO:7]; was chemically synthesized as a C-terminally amidated peptide (Pepscan Systems, Lelystad, The Netherlands). The correct peptide was obtained in greater than 99% yield and with measured mass of 1961 Da versus a calculated mass of 1962 Da and was homogeneous after preparative purification, as confirmed by mass spectrometry and analytic reversed phase-high performance liquid chromatography. A peptide "P5sc" containing the same amino-acids than P5 but in a different sequence order (TDSRCVIGLYH-PPLQVY; [SEQ ID NO:9]) was similarly synthesized and served as 'control peptide'.

In vitro Stimulation of Monocytes

For activation, monocytes were cultured in the presence of E.coli LPS (O111:B4, 1 µg/mL, Sigma-Aldrich, La Verpillière, France). Cell viability was assessed by trypan blue exclusion and by measuring lactate dehydrogenase release. In some experiments, this stimulus was given in combination with TNF-α (5 to 100 ng/mL, R&D Systems, Lille, France), IL-1β (5 to 100 ng/mL, R&D Systems), rIFN-γ (up to 100 U/mL, R&D Systems), rIL-10 (500 U/ml, R&D Systems) or up to 100 ng/mL of P5 or control peptide. In order to activate monocytes through TREM-1, an anti-TREM-1 agonist monoclonal antibody (R&D Systems) was added as follows: flat-bottom plates were precoated with 10 µg/mL anti- TREM-1 per well. After thorough washing in phosphate buffered saline (PBS), the monocyte suspensions were added at a similar concentration as above. Some experiments were performed in the presence of protease inhibitors (PMSF and Protease Cocktail Inhibitor; Invitrogen). Cell-free supernatants were assayed for the production of TNF-α and IL-1β by ELISA according to the recommendations of the manufacturer (BD Biosciences, San Diego, USA). To address the effect of P5 on NF-κB activity in monocytes, an ELISA-based assay was performed (BD Mercury™ Transfactor Kit, BD Biosciences). Monocytes were cultured for 24 hours in the presence of E.coli LPS (O111:B4, 1 µg/mL), and/or an agonist anti-TREM-1 monoclonal antibody (10 µg/mL), and/or P5 (100 ng/mL). Whole-cell extracts were then prepared and levels of NF-κB p50 and p65 were determined according to the recommendations of the manufacturer. All experiments were performed in triplicate and data are expressed as means (SEM).

Identification and Quantitation of sTREM-1 Release

Primary monocytes suspensions were cultured as described above. The cells were treated with E.coli LPS (O111:B4, 1 µg/mL) for 24 hours at 37° C. Cell-conditioned medium was submitted to Western-blotting using an anti-TREM-1 monoclonal antibody (R&D Systems) in order to confirm the presence of 27 kDa material recognized by anti-TREM-1. Soluble TREM-1 levels were measured by assessing the optical intensity of bands on immunodots by means of a reflectance scanner and the Quantity One Quantitation Software (Bio-Rad, Cergy, France) as reported elsewhere (18). Soluble TREM-1 concentration from each sample was determined by comparing the optical densities of the samples with reference to standard curves generated with purified TREM-1. All measurements were performed in triplicate. The sensitivity of this technique allows the detection of sTREM-1 levels as low as 5 pg/mL.

TREM-1 RT-PCR

Total mRNA was extracted from primary monocytes cultured in the presence of LPS using a TRIzol reagent (Invitrogen), and reverse transcribed using Superscript RT II (Invitrogen) to generate cDNA. RT-PCR conditions then used for all reactions were 94° C., 30 s/65° C., 30 s/68° C., 1 min for 30 cycles. Amplification was performed with 2.5 mM MgCl2, 0.2 mM dNTP, 2.0 U Taq polymerase, and 20 pM 5' and 3' oligonucleotide primers (Proligos, Paris, France).

The sequences of the 5' and 3' primer pairs used were the following:

```
for TREM-1 (17)
TTGTCTCAGAACTCCGAGCTGC;        [SEQ ID NO: 10]
and
GAGACATCGGCAGTTGACTTGG;        [SEQ ID NO: 11]

for TREM-1sv (19)
GGACGGAGAGATGCCCAAGACC;        [SEQ ID NO: 12]
and
ACCAGCCAGGAGAATGACAATG;        [SEQ ID NO: 13]

for β-actin (used as housekeeping amplicon)
GGACGACATGGAGAAGATCTGG;        [SEQ ID NO: 14]
and
ATAGTAATGTCACGCACGATTTCC;      [SEQ ID NO: 15]
```

PCR products were run on agarose gels and visualized by ethidium bromide staining.

LPS-Induced Endotoxinemia in Mice

After approval by the local ethical committee, male Balb/C mice (20 to 23 g) were randomly grouped and treated with E.coli LPS intraperitoneally (i.p.) in combination with P5 (in 500 µl normal saline) or control vector before or after LPS challenge. In some experiments, 5 µg of an anti TREM-1 monoclonal antibody was administered i.p. one hour after LPS injection. The viability of mice was examined every hour, or animals were sacrificed at regular intervals. Serum samples were collected by cardiac puncture and assayed for TNF-α and IL-1β by ELISA (BD Biosciences), and for sTREM-1 levels by immunodot.

CLP Polymicrobial Sepsis Model

Male Balb/C mice (7 to 9 weeks, 20 to 23 g) were anaesthetized by i.p. administration of ketamine and xylazine in 0.2 mL sterile pyrogen-free saline. The caecum was exposed through a 1.0 cm abdominal midline incision and subjected to a ligation of the distal half followed by two punctures with a G21 needle. A small amount of stool was expelled from the punctures to ensure patency. The caecum was replaced into the peritoneal cavity and the abdominal incision closed in two layers. After surgery all mice were injected s.c. with 0.5 ml of physiologic saline solution for fluid resuscitation and s.c. every 12 h with 1.25 mg (i.e. 50 µg/g) of imipenem. The animals were randomly grouped and treated with normal saline (n=14), the control peptide (n=14, 100 µg) or P5 (100 µg) in a single injection at H0 (n=18), H+4 (n=18) or H+24 (n=18). The last group of mice (n=18) was treated with repeated injections of P5 (100 µg) at H+4, H+8 and H+24. All treatments were diluted into 500 µl of normal saline and administered i.p. The Inventors next sought to determine the effect of various doses of P5. For this purpose, mice (n=15 per group) were treated with a single injection of normal saline or 10 µg, 20 µg, 50 µg 100 µg or 200 µg of P5 at H0 after the CLP and monitored for survival. Five additional animals per group were killed under anaesthesia 24 hours after CLP for the determination of bacterial count and cytokines levels. Peritoneal lavage fluid was obtained using 2 mL RPMI 1640 (Life Technologies) and blood was collected by cardiac puncture. Concentrations of TNF-α and IL-1β in the serum were determined by ELISA (BD Biosciences). For the assessment of bacterial counts, blood and peritoneal lavage fluid were plated in serial log dilutions on tryptic soy supplemented with 5% sheep blood agar plates. After plating, tryptic soy agar plates were incubated at 37° C. aerobically for 24 hours, and anaerobically for 48 hours. Results are expressed as CFU per mL of blood and CFU per mouse for the peritoneal lavage.

Statistical Analyses

Serum sTREM-1 and cytokines levels were expressed as mean (±SD). The protection against LPS lethality by P5 was assessed by comparison of survival curves using the Log-Rank test. All statistical analyses were completed with Statview software (Abacus Concepts, Berkeley Calif.) and a two-tailed P<0.05 was considered significant.

Results

A Soluble Form of TREM-1 is Released from Cultured Human Monocytes after Stimulation with E.coli LPS To identify the potential release of sTREM-1 in vitro, the Inventors stimulated human monocytes with LPS and analyzed the conditioned culture medium by SDS-PAGE. LPS stimulation induced the appearance of a 27-kDa protein in a time-dependent manner (FIG. 7A). Western blotting analysis revealed that this protein was specifically recognized by a monoclonal antibody directed against the extra-cellular domain of TREM-1 (FIG. 7A). Cell viability was unaffected at LPS concentrations that induced the presence of sTREM-1 in conditioned medium, indicating that TREM-1 release was not due to cell death. Similarly, treatment of monocytes with protease inhibitors did not affect TREM-1 release (FIG. 7A). TREM-1 mRNA levels were increased upon LPS treatment (FIG. 7B) whereas TREM-1sv mRNA levels remained undetectable. This suggests that TREM-1 release is likely to be linked to an increased transcription of the gene and unrelated to TREM-1sv expression. Stimulation of monocytes for 16 hours with TNF-α (5 to 100 ng/mL) or IL-1β (5 to 100 ng/mL) induced very small TREM-1 release in a cytokine dose-dependent manner. Stimulation with IFN-γ did not induce TREM-1 release, even at concentrations of up to 100 U/mL.

LPS Associated Release of Pro-Inflammatory Cytokines is Attenuated by P5

Significant TNF-α and IL-1β production was observed in the supernatant of monocytes cultured with LPS. TNF-α and IL-1β production was even higher for cells cultured with both TREM-1 mAb and LPS as compared with those cultured with mAb or LPS alone (FIG. 8A).

The inducible release of pro-inflammatory cytokines was significantly lower after LPS stimulation when the medium was supplemented with P5 or IL-10. P5 reduced, in a concentration-dependent manner, the TNF-α and IL-1β production from cells cultured with LPS or with LPS and mAb and simultaneously increased the release of sTREM-1 from cells cultured with LPS. The control peptide displayed no action on cytokines or sTREM-1 release (data not shown). In striking contrast, IL-10 totally inhibited the release of both TREM-1 and inflammatory cytokines (FIG. 8A). Both LPS and TREM-1 mAb induced a strong activation of monocytic NF-κB p50 and p65 and combined administration of LPS and TREM-1 mAb lead to a synergistic effect. P5 inhibited the NF-κB activation induced by the engagement of TREM-1 but did not alter the effect of LPS (FIG. 8B).

Serum sTREM-1 Levels of LPS-Treated Mice are Increased

In order to determine whether sTREM-1 was released systemically during endotoxemia in mice, the Inventors measured serum sTREM-1 levels after LPS administration. Serum sTREM-1 was readily detectable 1 hour after administration of an $LD_{50}$ dose of LPS and was maintained at peak plateau levels from 4 to 6 hours after LPS treatment (FIG. 9).

TREM-1 Peptide "P5" Protects Endotoxemic Mice from Lethality

Mice treated by a single dose of P5 60 min before a lethal dose ($LD_{100}$) of LPS were prevented from death in a dose-dependent manner (FIG. 10A). In order to investigate whether P5 treatment could be delayed until after the administration of LPS, the Inventors injected P5 beginning 4 or 6 hours after LPS injection. This delayed treatment up to 4 hours conferred significant protection against a $LD_{100}$ dose of LPS (FIG. 10B). No late death occurred over one week, indicating that P5 did not merely delay the onset of LPS lethality, but provided lasting protection. Control mice all developed lethargy, piloerection, and diarrhoea before death. By contrast, P5-treated mice remained well groomed and active, had no diarrhoea, and were lively. To clarify the mechanism by which P5 protected mice from LPS lethality, the Inventors determined the serum levels of TNF-α, IL-1β and sTREM-1 of endotoxemic mice at 2 and 4 hours. As compared to controls, pre-treatment by 100 μg of P5 reduced cytokines levels by 30% and increased sTREM-1 levels by 2 fold as shown in Table 4:

TABLE 4

Serum concentrations of TNF-α, IL-1β and sTREM-1 in endotoxemic mice.

| | TNF-α (ng/mL) | | IL-1β (ng/mL) | | sTREM-1 (ng/mL) | |
|---|---|---|---|---|---|---|
| | H2 | H4 | H2 | H4 | H2 | H4 |
| Control | 3.3 ± 1.0 | 0.4 ± 0.1 | 0.3 ± 0.1 | 1.5 ± 0.2 | 249 ± 48 | 139 ± 8 |
| P5 (100 μg) | 2.4 ± 0.5 | 0.1 ± 0.1 | 0.2 ± 0.1 | 0.9 ± 0.2 | 475 ± 37 | 243 ± 28 |

Engagement of TREM-1 is Lethal to Mice

To further highlight the role of TREM-1 engagement in LPS-mediated mortality, mice were treated with agonist anti-TREM-1 mAb in combination with the administration of an $LD_{50}$ dose of LPS. This induced a significant increase in mortality rate from 50% to 100% (FIG. 10C).

P5 Protects Mice from CLP-Induced Lethality

Figure 12:
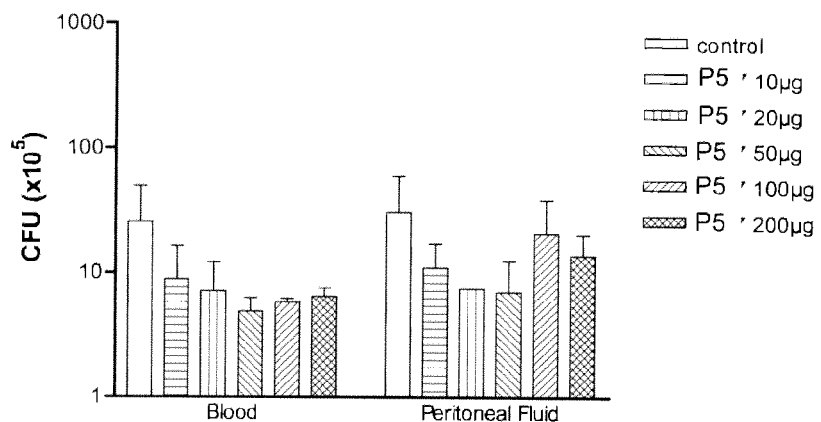

To investigate the role of P5 in a more relevant model of septic shock, the Inventors performed CLP experiments (FIG. 11A). The control groups comprised mice injected with normal saline or with the control peptide. In this model of polymicrobial sepsis, P5 still conferred a significant protection against lethality even when administered as late as 24 hours after the onset of sepsis. Interestingly, repeated injections of P5 had the more favourable effect on survival (P<0.01). There was a dose response effect of P5 on survival (FIG. 11B) and cytokine production (Table 5). P5 had no effect on bacterial clearance (FIG. 12).

TABLE 5

Serum concentrations of TNF-α, IL-1β
and sTREM-1 at 24 hours after CLP.

| | TNF-α (pg/mL) | IL-1β (pg/mL) | sTREM-1 (ng/mL) |
|---|---|---|---|
| Control peptide | 105 ± 12 | 841 ± 204 | 52 ± 3 |
| Control saline | 118 ± 8 | 792 ± 198 | 35 ± 5 |
| P5 10 μg | 110 ± 11 | 356 ± 62 | 43 ± 8 |
| P5 20 μg | 89 ± 10 | 324 ± 58 | 58 ± 8 |
| P5 50 μg | 24 ± 6 | 57 ± 11 | 93 ± 10 |
| P5 100 μg | 20 ± 3 | 31 ± 3 | 118 ± 12 |
| P5 200 μg | 21 ± 7 | 37 ± 8 | 158 ± 13 |

Sepsis exemplifies a complex clinical syndrome that results from a harmful or damaging host response to severe infection. Sepsis develops when the initial, appropriate host response to systemic infection becomes amplified, and then dysregulated (4, 5). Neutrophils and monocyte/macrophages exposed to LPS, for instance, are activated and release such pro-inflammatory cytokines as TNF-α and IL-1β. Excessive production of these cytokines is widely believed to contribute to the multi-organ failure that is seen in septic patients (20-23).

TREM-1 is a recently identified molecule involved in monocytic activation and inflammatory response (12, 14). It belongs to a family related to NK cell receptors that activate downstream signalling events. The expression of TREM-1 on PNNs and monocytes/macrophages has been shown to be inducible by LPS (16, 17).

As described herein, the Inventors demonstrate that a soluble form of TREM-1 was released from cultured human monocytes after stimulation with *E.coli* LPS. Such a soluble form was also detectable in the serum of endotoxemic mice as early as 1 hour after LPS challenge. This is consistent with the implication of TREM-1 in the very early phases of the innate immune response to infection (14, 15, 24). The mechanism by which sTREM-1 is released is not clearly elucidated but seems to be related to an increased transcription of the TREM-1 gene. Nevertheless, although incubation with a protease inhibitor cocktail does not alter the sTREM-1 release, cleavage of the surface TREM-1 from the membrane cannot be totally excluded. Interestingly, stimulation of human monocytes with such pro-inflammatory cytokines as TNF-α, IL-1β or IFN-γ induced very small sTREM-1 release unless LPS was added as a co-stimulus. The expression of an alternative mRNA TREM-1 splice variant (TREM-1sv) has been detected in monocytes that might translate into a soluble receptor (18) upon stimulation with cell wall fraction of *Mycobacterium bovis* BCG but not LPS (25). This was confirmed in this study as i) LPS did not increase the level of mRNA TREM-1sv in monocytes and ii) only a 27-kDa protein was released by monocytes upon LPS stimulation and not the 17.5-kDa variant.

Although its natural ligand has not been identified (13, 14), engagement of TREM-1 on monocytes with an agonist monoclonal antibody resulted in a further enhancement of pro-inflammatory cytokines production, while P5 induced a decrease of these syntheses in a concentration-dependent manner, and IL-10 completely suppressed it.

Inflammatory cytokines, and especially TNF-α, are considered to be deleterious, yet they also possess beneficial effects in sepsis (5) as shown by the fatal issue of peritonitis in animals with impaired TNF-α responses (9-11). Moreover, in clinical trials, the inhibition of TNF-α increased mortality (8). Finally, the role of TNF-α in the clearance of infection has been highlighted by the finding that sepsis is a frequent complication in rheumatoid arthritis patients treated with TNF-α antagonists (26).

The mechanism by which P5 modulates cytokine production is not yet clear. P5 comprises the complementary determining region (CDR)-3 and the 'F' β strand of the extracellular domain of TREM-1. The latter contains a tyrosine residue mediating dimerization. Radaev et al postulated that TREM-1 captures its ligand with its CDR-equivalent loop regions (27). P5 could thus impair TREM-1 dimerization and/or compete with the natural ligand of TREM-1. Moreover, the increase of sTREM-1 release from monocytes mediated by P5 could prevent the engagement of membrane TREM-1, sTREM-1 acting as a decoy receptor, as in the TNF-α system (28, 29).

Activation of the transcription factor NF-κB is a critical step in monocyte inflammatory cytokine production after exposure to bacterial stimuli such as LPS (30, 31). Among the various NF-κB/Rel dimers, the p65/p50 heterodimer is the prototypical form of LPS-inducible NF-κB in monocytes (32). P5 abolishes the p65/p50 NF-κB over-activation induced by the engagement of TREM-1. This might at least partially explain the effects of P5 on cytokine production and the protection from lethality shown here to occur when the peptide was injected one hour before LPS-induced septic shock, or even up to 4 hours after.

Endotoxemia is simple to achieve experimentally, but imperfectly suited to reproduce human sepsis, while polymicrobial sepsis induced by CLP is a more complex but better model, including the use of fluid resuscitation and antibiotics. The latter was thus also used in this study, and confirmed the dose-dependent protection provided by P5, even when administered as late as 24 hours after the onset of sepsis. The favourable effect of P5 was however unrelated to an enhanced bacterial clearance.

One difficulty in the use of immunomodulatory therapies is that it is not possible to predict the development of sepsis, and, thus, patients receiving those treatments frequently already have well-established sepsis (6). Since P5 appeared to be effective even when injected after the outbreak of sepsis, it could thus constitute a realistic treatment (24, 33).

By contrast, engagement of TREM-1 by an agonist anti-TREM-1 monoclonal antibody mediated a dramatic increase of mortality rate in LPS-challenged mice: this further underscores the detrimental effect of TREM-1 engagement during septic shock.

Experimental septic shock reproduces human sepsis only in part. Indeed, our group recently showed that significant levels of sTREM-1 were released in the serum of critically ill patients with sepsis patients (34), the highest levels being observed in patients who survived. This is consistent with our experimental findings indicating that the more important sTREM-1 release, the more favourable is the outcome, and thus sustains, at least theoretically, the potential value of soluble TREM peptides as post-onset sepsis therapy.

TREM-1 appears to be a crucial player in the immediate immune response triggered by infection. In the early phase of infection, neutrophils and monocytes initiate the inflammatory response owing to the engagement of pattern recognition receptors by microbial products (3, 4). At the same time, bacterial products induce the up-regulation and the release of sTREM-1. Upon recognition of an unknown ligand, TREM-1 activates signalling pathways which amplify these inflammatory responses, notably in monocytes/macrophages. The modulation of TREM-1 signalling reduces, although without complete inhibition, cytokine production and protects septic animals from hyper-responsiveness and death. Modulation of TREM-1 engagement with such a peptide as P5 might be a suitable therapeutic tool for the treatment of sepsis, particularly because it seems to be active even after the onset of sepsis following infectious aggression.

EXAMPLE 4

Haemodynamic Studies in LPS Treated and Septic Rats Treated with P1 and P5

The role of TREM-1 peptides in further models of septic shock, was investigated by performing LPS and CLP (caecal ligation and puncture) experiments in rats.

Materials and Methods

LPS-Induced Endotoxinemia

Animals were randomly grouped (n=10-20) and treated with *Escherichia coli* LPS (O111:B4, Sigma-Aldrich, Lyon, France) i.p. in combination with the TREM-1 or scrambled peptides.

CLP Polymicrobial Sepsis Model

The procedure has been described in details elsewhere (see Mansart, A. et al. Shock 19:38-44 (2003)). Briefly, rats (n=6-10 per group) were anesthetized by i.p. administration of ketamine (150 mg/kg). The caecum was exposed through a 3.0-cm abdominal midline incision and subjected to a ligation of the distal half followed by two punctures with a G21 needle. A small amount of stool was expelled from the punctures to ensure potency. The caecum was replaced into the peritoneal cavity and the abdominal incision closed in two layers. After surgery, all rats were injected s.c. with 50 mL/kg of normal saline solution for fluid resuscitation. TREM-1 or scrambled peptides were then administered as above.

Haemodynamic Measurements in Rats

Immediately after LPS administration as well as 16 hours after CLP, arterial BP (systolic, diastolic, and mean), heart rate, abdominal aortic blood flow, and mesenteric blood flow were recorded using a procedure described elsewhere (see Mansart, A. et al. Shock 19:38-44 (2003)). Briefly, the left carotid artery and the left jugular vein were cannulated with PE-50 tubing. Arterial BP was continuously monitored by a pressure transducer and an amplifier-recorder system (IOX EMKA Technologies, Paris, France). Perivascular probes (Transonic Systems, Ithaca, N.Y.) wrapped up the upper abdominal aorta and mesenteric artery, allowed to monitor their respective flows by means of a flowmeter (Transonic Systems). After the last measurement ($4^{th}$ hour during LPS experiments and $24^{th}$ hour after CLP), animals were sacrificed by an overdose of sodium thiopental i.v.

Biological Measurements

Blood was sequentially withdrawn from the left carotid artery. Arterial lactate concentrations and blood gases analyses were performed on an automatic blood gas analyser (ABL 735, Radiometer, Copenhagen, Denmark). Concentrations of TNF-α and IL-1β in the plasma were determined by an ELISA test (Biosource, Nivelles, Belgium) according to the recommendations of the manufacturer. Plasmatic concentrations of nitrates/nitrites were measured using the Griess reaction (R&D Systems, Abingdon, UK).

Statistical Analyses

Results are expressed as mean±SD. Between-group comparisons were performed using Student't tests. All statistical analyses were completed with Statview software (Abacus Concepts, Calif.) and a two-tailed P<0.05 was considered significant.

Results

Endotoxinemia Model

Following LPS administration, arterial pressures, aortic and mesenteric blood flows dropped rapidly in control animals (scrambled peptides treated rats) while the heart rate remained unchanged (Table 6). The decrease of arterial pressures and aortic blood flow was delayed until the second hour in TREM-1 peptide treated animals with significantly higher values by that time than in control animals. There was no difference between P1 and P5 treated groups. By contrast, none of these two peptides had any effect on the decrease of the mesenteric blood flow (Table 6).

Arterial pH remained constant over time until the fourth hour after LPS injection where it severely dropped in the control group only (Table 6). The significant arterial lactate level elevation present in control animals after the third hour was abolished by the TREM-1 peptides (Table 6). There was no difference between P1 and P5 with regard to pH, arterial bicarbonate and lactate concentrations.

As expected, a peak of TNF-α plasmatic concentration was induced by LPS between 30 minutes and 1 hour after injection followed by a progressive decline thereafter (FIG. 13A). P1 peptide injection had no effect on this production, while P5 attenuated TNF-α production by ~30%.

P1 delayed the IL-1β peak until the third hour after LPS injection, but without attenuation. By contrast, P5 strongly reduced IL-1β release (FIG. 13B).

Nitrite/nitrate concentrations increased rapidly after LPS administration in control and P1 treated animals but remained stable upon P5 treatment (FIG. 14).

TABLE 6

Hemodynamic parameters during LPS-induced endotoxinemia

| | | Heart Rate (bpm) | MAP (mmHg) | Aortic blood flow (mL/min) | Mesenteric blood flow (mL/min) | pH | Lactate (mmol/L) |
|---|---|---|---|---|---|---|---|
| Control | H0 | 486 ± 13 | 123 ± 21 | 45 ± 7 | 13.6 ± 3.4 | 7.31 ± 0.03 | 3.3 ± 0.8 |
| | H1 | 522 ± 16 | 103 ± 25 | 25 ± 8$^a$ | 9.6 ± 3.3 | 7.28 ± 0.03 | 4.2 ± 0.3 |
| | H2 | 516 ± 13 | 98 ± 23 | 12 ± 5$^{a,b}$ | 8.0 ± 3.7 | 7.29 ± 0.03 | 5.9 ± 0.6 |
| | H3 | 490 ± 20 | 78 ± 8$^{a,b}$ | 8 ± 3$^{a,b}$ | 5.8 ± 1.1 | 7.26 ± 0.01 | 7.9 ± 1.8$^{a,b}$ |
| | H4 | 510 ± 18 | 67 ± 9$^{a,b}$ | 6 ± 1$^{a,b}$ | 4.1 ± 0.8 | 7.03 ± 0.10$^{a,b}$ | 11.5 ± 0.7$^{a,b}$ |
| P1 | H0 | 464 ± 25 | 116 ± 10 | 49 ± 11 | 12.0 ± 3.7 | 7.32 ± 0.04 | 2.7 ± 0.1 |
| | H1 | 492 ± 26 | 119 ± 14 | 39 ± 12$^a$ | 10.5 ± 1.7 | 7.29 ± 0.04 | 4.9 ± 1.1 |
| | H2 | 492 ± 26 | 113 ± 21 | 26 ± 14$^a$ | 7.7 ± 2.7 | 7.30 ± 0.01 | 5.0 ± 0.9 |
| | H3 | 480 ± 30 | 97 ± 29$^a$ | 22 ± 8$^a$ | 5.0 ± 1.0 | 7.26 ± 0.06 | 5.7 ± 0.7$^a$ |
| | H4 | 480 ± 20 | 92 ± 7$^a$ | 16 ± 6$^a$ | 4.8 ± 0.9 | 7.26 ± 0.08$^a$ | 7.9 ± 1.7$^a$ |
| P5 | H0 | 474 ± 49 | 115 ± 16 | 48 ± 9 | 12.8 ± 6.4 | 7.33 ± 0.04 | 3.4 ± 1.5 |
| | H1 | 498 ± 26 | 99 ± 22 | 32 ± 8 | 11.4 ± 2.7 | 7.28 ± 0.06 | 5.4 ± 1.4 |
| | H2 | 510 ± 42 | 101 ± 18 | 23 ± 4$^b$ | 9.2 ± 1.9 | 7.32 ± 0.07 | 5.5 ± 1.6 |
| | H3 | 517 ± 62 | 93 ± 21$^b$ | 20 ± 7$^b$ | 6.0 ± 0.8 | 7.29 ± 0.11 | 5.9 ± 1.7$^b$ |
| | H4 | 510 ± 26 | 89 ± 10$^b$ | 15 ± 6$^b$ | 5.0 ± 1.0 | 7.28 ± 0.12$^b$ | 7.4 ± 1.8$^b$ |

$^a$p < 0.05 P1 vs Controls
$^b$p < 0.05 P5 vs Controls

CLP Model

As the severity of the Inventors' model was at its highest 16 to 20 hours after the completion of the CLP, the Inventors chose to investigate animals by the $16^{th}$ hour. Importantly, there were no deaths before this time point. Although all animals were fluid resuscitated, none received antibiotics in order to strictly consider the role of the peptides.

There was a dramatic decline in arterial pressure in the control animals over time, and by H24 systolic, diastolic and mean arterial pressures were 58±7 mmHg, 25±4 mmHg and 38±2 mmHg respectively. This decrease was almost totally abolished with P1 or P5 treatment with no significant difference between H16 and H24 (FIG. 15). There was no difference between P1 and P5 treated rats.

TREM-1 peptides also prevented the aortic and mesenteric blood flows decrease observed in control animals (Table 7). The protective effect on mesenteric blood flow alterations was even higher under P5 treatment. The relative preservation of blood flows was not related to an increased heart rate, since the latter was rather slower than in control animals (Table 7).

The progressive metabolic acidosis that developed in control rats was attenuated by the P1 peptide, and almost abrogated by P5. The same protective trend was observed for arterial lactate elevation with a more pronounced effect of P5 (Table 7).

TABLE 7

Hemodynamic and selected biochemical parameters during CLP polymicrobial sepsis

|  |  | Heart Rate (bpm) | Aortic blood flow (mL/min) | Mesenteric blood flow (mL/min) | pH | Bicarbonate (mmol/L) | Lactate (mmol/L) |
|---|---|---|---|---|---|---|---|
| Control | H16 | 516 ± 44$^{a,b}$ | 38 ± 10 | 10.6 ± 3.0$^b$ | 7.31 ± 0.07$^b$ | 16.9 ± 2.7 | 4.7 ± 1.5$^b$ |
|  | H20 | 543 ± 35$^{a,b}$ | 19 ± 11$^{a,b}$ | 4.3 ± 1.5$^b$ | 7.23 ± 0.05$^{a,b}$ | 12.0 ± 5.6$^{a,b}$ | 8.5 ± 1.4$^{a,b}$ |
|  | H24 | 480 ± 20 | 14 ± 9$^{a,b}$ | 2.5 ± 0.7$^b$ | 7.17 ± 0.01$^{a,b}$ | 10.3 ± 3.3$^a$ | 10.8 ± 1.9$^{a,b}$ |
| P1 | H16 | 462 ± 16$^a$ | 41 ± 12 | 13.5 ± 7.2 | 7.32 ± 0.04 | 16.8 ± 4.4 | 4.9 ± 0.4 |
|  | H20 | 480 ± 30$^a$ | 28 ± 17$^a$ | 5.3 ± 3.0$^c$ | 7.31 ± 0.18$^a$ | 16.0 ± 5.4$^b$ | 5.3 ± 1.1$^{a,c}$ |
|  | H24 | 420 ± 30 | 22 ± 16$^a$ | 4.5 ± 2.1$^c$ | 7.24 ± 0.06$^{a,c}$ | 11.2 ± 0.8$^c$ | 6.8 ± 0.9$^{a,c}$ |
| P5 | H16 | 460 ± 17$^b$ | 41 ± 14 | 15.3 ± 3.5$^b$ | 7.35 ± 0.01$^b$ | 18.6 ± 2.0 | 3.3 ± 0.4$^b$ |
|  | H20 | 500 ± 17$^b$ | 31 ± 5$^b$ | 11.0 ± 6.9$^{b,c}$ | 7.34 ± 0.01$^b$ | 18.0 ± 0.9$^a$ | 3.6 ± 0.9$^{b,c}$ |
|  | H24 | 510 ± 20 | 28 ± 8$^b$ | 8.5 ± 3.5$^{b,c}$ | 7.36 ± 0.01$^{b,c}$ | 17.1 ± 0.9$^{a,c}$ | 4.9 ± 1.1$^{b,c}$ |

$^a$p < 0.05 P1 vs Controls
$^b$p < 0.05 P5 vs Controls
$^c$p < 0.05 P5 vs P1

Both P1 and P5 induced a decrease in TNF-α production, again with a stronger effect of P5. By H20, plasmatic TNF-α was almost undetectable under P5 treatment whereas it remained elevated in the other groups of animals (FIG. 16).

Nitrite/nitrate concentrations were increased in control animals but remained at a low level in both TREM-1 peptides treated groups (FIG. 17).

A protective action of both P5 and P1 on hemodynamics was thus observed in septic rats. Both arterial pressure and blood flows were preserved, independently of heart rate. Moreover, modulation of TREM-1 signalling reduced, although not completely, cytokine production and protected septic animals from hyper-responsiveness. The fact that the cytokine production was not totally inhibited is a crucial point. Indeed, although inflammatory cytokines such as TNF-α are considered deleterious, they also display beneficial effects in sepsis as underlined by the fatal issue of peritonitis models in animals with impaired TNF-α responses.

The activation of iNOS observed during septic shock leads to the production of large amount of NO that partly explains some of the peripheral vascular disorders (notably vasodilation and hypotension). On the myocardium itself, most of the action of NO is mediated by an activation of the soluble guanylate-cyclase responsible for the production of cGMP which impairs the effect of cytosolic calcium on contraction. Cyclic GMP is also able to stimulate the activity of some phosphodiesterases. The subsequent decrease of intra-cellular cAMP levels could explain the ability of NO to attenuate the effects of beta adrenergic stimulation. The preservation of arterial pressure could therefore be partly explained by a lessened production of NO, as reflected by the lower concentrations of plasma nitrite/nitrate in TREM-1 peptides treated animals.

The decrease in inflammatory cytokine production could partly explain the effect noted on blood flows. Indeed, although the list of potential cytokine mediators of myocardial depression is long, TNF-α and IL-1β have been shown to be good candidates Both these latter cytokines depressed myocardial contractility in vitro or ex vivo. Moreover, the neutralization or removal of TNF-α or IL-1β from human septic serum partly abrogates the myocardial depressant effect in vitro and in vivo. Although P1 and P5 had an identical action on blood flows and arterial pressure during endotoxinemia, their action on cytokine production differed with only a slight effect of P1 on plasma TNF-α and IL-1β concentrations. The protective role of the TREM-1 peptides could therefore be only partly related to their action on cytokine release, or involve redundant pathways.

The modulation of the TREM-1 pathway by the use of small synthetic peptides had beneficial effects on haemodynamic parameters during experimental septic shock in rats, along with an attenuation of inflammatory cytokine production.

In summary, these data show that the TREM-1 peptides of the invention 1) efficiently protect subject animals from sepsis-related hemodynamic deterioration; 2) attenuate the development of lactic acidosis; 3) modulate the production of such pro-inflammatory cytokines as TNF-α and IL-1β and 4) decrease the generation of nitric oxide. Thus TREM-1 peptides are potentially useful in the restoration of haemodynamic parameters in patients with sepsis, septic shock or sepsis-like conditions and therefore constitute a potential treatment for the aforesaid conditions.

EXAMPLE 5 hP5 Activity in a Murine Model of Sepsis: Endotoxin-Induced Septic Shock

The activity of human P5 (hP5) was investigated in a murine model. hP5 differs from mP5 according to ClustalW comparison as set our below:

```
SeqA  Name              Length (aa)  SeqB  Name  Length (aa)  Score 1     hP5               17           2     mP5   17           82 hP5   LQVEDSGLYQCVIYQPP              17
mP5   LQVTDSGLYRCVIYHPP              17
      *** ***** **** **
```

For the experiment, male BALB/c mice (19-21 g) were randomly grouped (15 mice per group) and injected intraperitoneally (i.p.) with 200 microg of LPS from *E. coli* 0111:B4 (Sigma). A blinded investigator performed all injections. 200 microliters of TREM-1 peptides dissolved in water 10% DMSO, 9% Solutol were administered intraperitoneally at −1 h, 0 h, +1 h, +4 h prior and after LPS injection. Viability of treated mice was monitored twice a day for 7 days.

To then assess the ability of hP5 peptide to protect mice from LPS-induced endotoxaemia, the inventors administered at −1 h, 0 h, +1 h, +4 h prior and after LPS injection a lethal dose of lipopolysaccharide (LPS) (FIG. 18). Lethality was monitored over time and compared with animals that had received vehicle alone. hP5 injection confers high protection, with 80% of the animals still alive 7 days after LPS injection, as compared with no survivors in the control group ($p<0.0003$). The human P5 peptide shows >80% identity with mP5.

The results summarised in FIG. 18 clearly demonstrate that the human P5 protects mice from lethal shock.

EXAMPLE 6 hP5 Activity in a Murine Model of Sepsis: Cecal Ligation and Puncture Model

For the experiment the mice underwent a standardized preparation for laparotomy (anaesthesia with 2% inhaled isoflurane in oxygen, shaving with animal clippers, alcohol scrub). A 1 cm incision was made on the midline. The cecum was exposed and will be tightly ligated at 50-80% over its base with a 4-0 silk suture avoiding bowel obstruction. The cecum was then punctured once with a 23G needle. The cecum was gently squeezed until feces be just visible through the puncture, and placed again in the abdominal cavity. The incision was thereafter be closed with a 4-0 silk. 200 µl of hP5 or its scrambled peptide control were freshly dissolved in water 10% DMSO, 9% solutol and injected intraperitoneally with a 22 G needle at the following time points: −1, 0, +4, +24. No fluid resuscitation was administered. Survival and Moribundity were observed twice a day for 10 days.

The Inventors then analysed whether hP5 protects against septic shock in the "CLP" model. Mice treated with four doses of hP5 at −1 h, 0 h, +4 h and +24 hours after CLP were protected from death as compared to control treated mice. At 72 hours after CLP, 73.3% of the mice injected with hP5 survived compared to 60% of mice treated with scrambled peptide. At 10 days after CLP, 66.6% of the hP5 treated mice were still alive compared to 60% of the control group, suggesting that hP5 could provide lasting protection (FIG. 19).

EXAMPLE 7

The human TREM-1 Peptide P5 (hP5) Attenuates Established Intestinal Inflammation in the DSS Colitis Model The purpose of this example is to identify, characterize and document the therapeutic potential of the TREM-1 derived peptide hP5, in an experimental model of colitis in mice.

On day 0 of the study, the water supply was removed and replaced with 3% Dextran Sulfate Sodium (DSS) From day 0 to day 6, this solution was the only source of fluids. Water was administered for the rest of the experiment (day 7-11). Healthy controls received water only.

From day 3 to day 10 mice were treated with either hP5, or a sequence-scrambled control peptide. Peptides were dissolved in DMSO at 10 mg/ml and stored at +4° C. Before administration, the stock solution was diluted 1:10 in water 10% Solutol® HS 15 (BASF). Final vehicle concentrations: 1% DMSO, 10% solutol in water. 200 µl of these freshly prepared solutions of hP5, its scrambled control or vehicle were injected intraperitoneally with a 25 G needle.

Animals were weighted daily and monitored on days 3, 4, 5, 6, 7 and 10 for rectal bleeding and stool consistency. For each group, the disease activity index (DAI) was determined by evaluating changes in weight, stool consistency and presence of gross blood during the study, as described below:

| Score | Weight loss (%) | Stool consistency | Blood in stool |
|---|---|---|---|
| 0 | <1 | Normal | Negative |
| 1 | 1-4, 9 | Soft | +/− |
| 2 | 5-9, 9 | Mixed (soft and liquid) | + |
| 3 | 10-15 | Liquid | ++ |
| 4 | >15 | Diarrhea (liquid stools that adhere to the anus) | Gross bleeding |

Scoring System for the Disease Activity Index (DAI).

Individual scores for each parameter are added and then divided by three to give a DAI score for each mouse.

To determine the presence of occult blood in stool, a pea-sized stool sample was placed on a slide. Then two drops of reagent (Hemocult Sensa, Beckman Coulter) were placed onto the stool sample on the slide and a change of colour was observed. The presence of occult blood was graded using a score of 0 for no colour; 1 for a very light blue (+/−) colour taking over 30 seconds to appear, 2 for a blue colour developing in 30 seconds or more (+); 3 for an immediate change in colour (++) and 4 for gross blood observable on the slide.

On day 11 mice were euthanized by cervical dislocation to allow colon length evaluation. An incision was done in the abdomen to expose the colon. The stool in the colon was removed flushing with saline. The entire colon from cecum to anus was removed and the length was measured and reported as colon length (cm).

Data were analyzed using Graph Pad Prism. Results are given as means±standard error of the mean. The BW score, stool score and blood score were analyzed using two-way ANOVA test, Bonferroni post test. Colon length was analysed using one-way ANOVA, Dunn's post test. $*P\leq0.05$; $P\leq0.01$; $*P\leq0.001$ mP5 is a mTREM-1 derived peptide whose efficacy has been proven in several models of sepsis. In this study, the investigators have tested the efficacy of the human orthologue of mP5, compared to its scrambled peptide control, in the above described DSS-induced colitis model. All peptides were administered in a therapeutic fashion, 3 days after initiation of DSS treatment.

In all animals, body weight, haemoccult or presence of gross blood and stool consistency were monitored. Bloody stools were observed from day 3 onwards, loose stools and weight loss appeared beginning from day 4-5. These comprehensive functional measures, that were somewhat analogous to clinical symptoms observed in human IBD, are summarized by the Disease Activity Index, as shown in FIG. 20. This scoring method, validated by repeated studies, showed minimum variations and correlates well with more specific measures of inflammation.

None of the control animals showed disease activity. DAI peaked at day 5-6 and regressed upon DSS removal. As soon as colitis was established (day 5), hP5 administration significantly ameliorated stool consistency (FIG. 23) and colon bleeding (FIG. 22), as shown by approximately a 50% DAI inhibition, when compared to mice treated with DSS+vehicle or DSS+scrambled peptide (1.95±0.170 vs. 2.92±0.054, p≤0.001 or 3.00±0.088, p≤0.001, respectively).

Protection lasted during the whole treatment. Notably at day 10, in the hP5-treated group both stool score and hemoccult were normal (FIGS. 23 and 22), while the groups treated with DSS+vehicle and DSS+scrambled peptide still showed clinical signs of inflammation (blood score: DSS+hP5=0.43±0.202 vs DSS+vehicle=1.25±0.164; p≤0.01; DSS+hP5=0.43±0.202 vs DSS+scrambled peptide=1.75±0.250; p≤0.001. Stool score: DSS+hP5=0.71±0.474 vs DSS+vehicle=1.75±0.250 p≤0.05; DSS+hP5=0.71±0.474 vs DSS+scrambled peptide=2.38±0.324; p≤0.001).

We also monitored weight loss associated with the development of colitis. FIG. 21 represents the percentage of weight loss, expressed as a score. Mice started loosing weight at day 4 and the maximal weight loss was reached at day 8. hP5 treatment significantly reduced weight loss in comparison with DSS+scrambled, from day 8 on (day 10: hP5=2.00±0.436 vs DSS+scrambled pep. 3.50±0.189; p≤0.001). At day 11 mice were euthanized and the colon length of each mouse measured from the anus to the end of the cecum (FIG. 24). DSS-induced colon inflammation caused a 30% colon shortening when compared to naïve animals. In the hP5-treated group, colon shortening was significantly ameliorated when compared to control group (hP5=7.41±0.237 vs DSS+vehicle=5.96±0.230; p≤0.05). In conclusion, blocking TREM-1 with a human TREM-1 derived peptide attenuates intestinal inflammation even when the peptide is administered after the appearance of the clinical signs of colitis. This finding indicates that the human TREM-1-derived peptide efficiently blocks interaction of the mouse TREM-1 receptor with its endogenous ligand.

REFERENCES

1. Aderem, A, and R. J. Ulevitch, R. J. 2000. Toll-like receptors in the induction of the innate immune response. *Nature* 406:782-786.
2. Thoma-Uszynski, S., S. Stenger, O. Takeuchi, M. T. Ochoa, P. A. Engele, P. A. Sieling, P. F. Barnes, M. Rollinghoff, P. L. Bolcskei, and M. Wagner. 2001. Induction of direct antimicrobial activity through mammalian Toll-like receptors. *Science* 291:1544-1549.
3. Medzhitov, R., and C Jr. Janeway. 2000. Innate immunity. *N. Engl. J. Med.* 343:338-344.
4. Cohen, J. 2002. The immunopathogenesis of sepsis. *Nature* 420:885-91.
5. Hotchkiss, R. S., and I. E. Karl. 2003. The pathophysiology and treatment of sepsis. *N. Engl. J. Med.* 348:138-50.
6. Vincent, J. L., Q. Sun, and M. J. Dubois. 2002. Clinical trials of immunomodulatory therapies in severe sepsis and septic shock. *Clin. Infect. Dis.* 34:1084-1093.
7. Riedemann, N. C., R. F. Guo, and P. Ward. 2003. Novel strategies for the treatment of sepsis. *Nat. Med.* 9:517-524.
8. Fisher, C. J. Jr., J. M. Agosti, S. M. Opal, S. F. Lowry, R. A. Balk, J. C. Sadoff, E. Abraham, R. M. Schein, and E. Benjamin. 1996. Treatment of septic shock with the tumor necrosis factor receptor:Fc fusion protein. The Soluble TNF Receptor Sepsis Study Group. *N. Engl. J. Med* 334:1697-702.
9. Echtenacher, B., W. Falk, D. N. Mannel, and P. H. Krammer. 1990. Requirement of endogenous tumor necrosis factor/cachectin for recovery from experimental peritonitis. *J. Immunol.* 145:3762-3766.
10. Echtenacher, B., K. Weigl, N. Lehn, and D. N. Mannel. 2001. Tumor necrosis factor-dependent adhesions as a major protective mechanism early in septic peritonitis in mice. *Infect. Immun.* 69:3550-5.
11. Eskandari, M. K., G. Bolgos, C. Miller, D. T. Nguyen, L. E. DeForge, and D. G. Remick. 1992. Anti-tumor necrosis factor antibody therapy fails to prevent lethality after cecal ligation and puncture or endotoxemia. *J. Immunol.* 148:2724-30.
12. Bouchon, A., J. Dietrich, and M. Colonna. 2000. Inflammatory responses can be triggered by TREM-1, a novel receptor expressed on neutrophils and monocytes. *J. Immunol.* 164:4991-4995.
13. Colonna, M., and F. Facchetti. 2003. TREM-1 (triggering receptor expressed on myeloid cells): a new player in acute inflammatory responses. *J. Infect. Dis.* 187 (Suppl):S297-301.
14. Colonna, M. 2003. TREMs in the immune system and beyond. *Nat. Rev. Immunol.* 6:445-453.
15. Nathan, C., and A. Ding. 2001. TREM-1: a new regulator of innate immunity in sepsis syndrome. *Nat. Med.* 7:530-2.
16. Bouchon, A., F. Facchetti, M. A. Weigand, and M. Colonna. 2001. TREM-1 amplifies inflammation and is a crucial mediator of septic shock. *Nature* 410:1103-1107.
17. Bleharski, J. R., V. Kiessler, C. Buonsanti, P. A. Sieling, S. Stenger, M. Colonna, and R. L. Modlin. 2003. A role for Triggering Receptor Expressed on Myeloid cells-1 in host defense during the early-induced and adaptive phases of the immune response. *J. Immunol.* 170:3812-3818.
18. Gibot, S., A. Cravoisy, B. Levy, M. C. Béné, G. Faure, and P. E. Bollaert. 2004. Soluble triggering receptor expressed on myeloid cells and the diagnosis of pneumonia. *N. Engl. J. Med.* 350:451-8.
19. Gingras, M. C., H. Lapillonne, and J. F. Margolin. 2001. TREM-1, MDL-1, and DAP12 expression is associated with a mature stage of myeloid development. *Mol. Immunol.* 38:817-24.
20. Dinarello, C. A. 1997. Proinflammatory and anti-inflammatory cytokines as mediators in the pathogenesis of septic shock. *Chest* 112 (suppl):521-9.
21. Bone, R. C., R. A Balk, F. B. Cerra, R. P. Dellinger, W. A. Knauss, R. M. Schein, and W. J. Sibbald. 1992. Definitions for sepsis and organ failure and guidelines for the use of innovative therapies in sepsis. The ACCP/SCCM Consensus Conference Committee. American in sepsis. The ACCP/SCCM Consensus Conference Committee. American College of Chest Physicians/Society of Critical Care Medicine. *Chest* 101:1644-55.
22. Warren, H. S. 1997. Strategies for the treatment of sepsis. *N. Engl. J. Med.* 336:952-3.
23. Stone, R. 1994. Search for sepsis drugs goes on despite past failures. *Science* 264:365-7.
24. Cohen, J. 2001. TREM-1 in sepsis. *Lancet* 358:776-8.
25. Begun, N. A., K. Ishii, M. Kurita-Taniguchi, M. Tanabe, M. Kobayashi, Y. Moriwaki, M. Matsumoto, Y. Fukumori, I. Azuma, K. Toyoshima, and T. Seya. 2004. *Mycobacterium bovis* BCG cell wall-specific differentially expressed genes identified by differential display and cDNA substraction in human macrophages. *Infect. Immun.* 12:937-48.
26. Keane, J., S. Gershon, R. P. Wise, E. Mirabile-Levens, J. Kasznica, W. D. Schwieterman, J. N. Siegel, and M. M. Braun. 2001. Tuberculosis associated with infliximab, a tumor necrosis factor alpha-neutralizing agent. *N. Engl. J. Med.* 345:1098-104.

27. Radaev, S., M. Kattah, B. Rostro, M. Colonna, and P. Sun. 2003. Crystal structure of the human myeloid cell activating receptor TREM-1. *Structure* 11:1527-35.
28. Lantz, M., U. Gullberg, and E. Nilsson. 1990. Characterization in vitro of a human tumor necrosis factor binding protein. A soluble form of tumor necrosis factor receptor. *J. Clin. Invest.* 86:1396-1401.
29. van Zee, K. J., T. Kohno, and E. Fischer. 1992. Tumor necrosis soluble receptors circulate during experimental and clinical inflammation and can protect against excessive tumor necrosis factor α in vitro and in vivo. *Proc. Natl. Acad. Sci. USA* 89:4845-4853.
30. Collart, M. A., P. Baeuerle, and P. Vassalli. 1990. Regulation of tumor necrosis factor alpha transcription in macrophages. Involvement of four NFκB motifs and constitutive and inducible form of NFκB. *Mol. Cell Biol.* 10:1498-506.
31. Hiscott, J. M., J. J. Garoufalis, A. Roulston, I. Kwan, N. Pepin, J. Lacoste, H. Nguyen, G. Bensi, and M. Fenton. 1993. Characterization of a functional NFκB site in the human IL-1β promoter: evidence for a positive autoregulatory loop. *Mol. Cell Biol.* 13:6231-40.
32. Urban, M. B., R. Schreck, and P. A. Baeuerle. 1991. NFκB contacts DNA by a heterodimer of the p50 and p65 subunit. *EMBO J.* 10:1817-25.
33. Lolis, E., and R. Bucala. 2003. Therapeutic approaches to innate immunity: severe sepsis and septic shock. *Nat. Rev. Drug. Discov.* 2:635-45.
34. Gibot, S., M. N. Kolopp-Sarda, M. C. Béné, A. Cravoisy, B. Levy, G. Faure, and P. E. Bollaert. 2004. Plasma level of a triggering receptor expressed on myeloid cells-1: its diagnostic accuracy in patients with suspected sepsis. *Ann. Intern. Med.* 141:9-15.
35. Schenk M, Bouchon A, Seibold F, and Mueller C. 2007.

The invention claimed is:

1. An isolated peptide or derivative thereof, which is capable of acting as an antagonist of the TREM-1 protein as defined by SEQ ID NO. 1, comprising the amino acid sequence of SEQ ID NO. 20 or at least 3 amino acids of SEQ ID NO. 21, wherein:

(a) the peptide consists of:
  (i) a contiguous sequence of 5 to 29 amino acids from SEQ ID NO: 1; or
  (ii) a contiguous sequence of 5 to 29 amino acids from SEQ ID NO: 1 in which one amino acid is substituted conservatively with another amino acid; or (b) the peptide consists of an amino acid sequence having at least 80% sequence identity to SEQ ID NOs: 16, 17, 18 or 19; and wherein the derivatives of the peptides of (a) or (b) are modified by glycosylation, acetylation, pegylation, phosphorylation, amidation, or derivatization by protecting or blocking groups.

2. The isolated peptide or derivative thereof according to claim 1, which consists of:

(a) a contiguous sequence of 5 to 29 amino acids from SEQ ID NO: 1; or (b) a contiguous sequence of 5 to 29 amino acids from SEQ ID NO: 1 in which one amino acid is substituted conservatively with another amino acid; and wherein the derivatives of the peptides of (a) or (b) are modified by glycosylation, acetylation, pegylation, phosphorylation, amidation, or derivatization by protecting or blocking groups.

3. The isolated peptide or derivative thereof according to claim 1, wherein the peptide consists of an amino acid sequence having at least 80% sequence identity to SEQ ID NOs: 16, 17, 18 or 19;

and wherein the derivatives of the peptide are modified by glycosylation, acetylation, pegylation, phosphorylation, amidation, or derivatization by protecting or blocking groups.

4. The isolated peptide or a derivative thereof according to claim 3, wherein the peptide consists of an amino acid sequence having at least 80% sequence identity to SEQ ID NO: 19.

5. The isolated peptide or derivative thereof according to claim 3, wherein the peptide consists of an amino acid sequence having the sequence of SEQ ID NOs: 16, 17, 18 or 19, or which differs from said sequence by one or more conservative amino acid modifications.

6. The isolated peptide according to claim 4, wherein the peptide consists of an amino acid having the sequence of SEQ ID NO: 19, or which differs from said sequence by one or more conservative modifications.

7. The isolated peptide or derivative thereof according to claim 1, wherein said peptide consists of a contiguous sequence of 15 to 29 amino acids from SEQ ID NO. 1.

8. The isolated peptide or derivative thereof according to claim 1, which comprises at least 3 amino acids from SEQ ID NO. 21, wherein the at least 3 amino acids from SEQ ID NO. 21 are selected from the group consisting of QPP, QPPK (SEQ ID NO: 24), and QPPKE (SEQ ID NO. 21).

9. The isolated peptide or derivative thereof according to claim 3, wherein the peptide consists of an amino acid sequence having the sequence of SEQ ID NOs: 16, 17, 18 or 19.

10. A composition comprising the isolated peptide or derivative thereof according to claim 1, and a pharmaceutically acceptable carrier.

* * * * *

SEQUENCE LISTING

```
<160> NUMBER OF SEQ ID NOS: 27

<210> SEQ ID NO 1
<211> LENGTH: 234
<212> TYPE: PRT
<213> ORGANISM: Homo sapiens

<400> SEQUENCE: 1

Met Arg Lys Thr Arg Leu Trp Gly Leu Leu Trp Met Leu Phe Val Ser
 1               5                  10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Val Pro Val Phe Asn Ile Val Ile
        195                 200                 205

Leu Leu Ala Gly Gly Phe Leu Ser Lys Ser Leu Val Phe Ser Val Leu
    210                 215                 220

Phe Ala Val Thr Leu Arg Ser Phe Val Pro
225                 230

<210> SEQ ID NO 2
```

-continued

```
<211> LENGTH: 230
<212> TYPE: PRT
<213> ORGANISM: Mus musculus

<400> SEQUENCE: 2

Met Arg Lys Ala Gly Leu Trp Gly Leu Leu Cys Val Phe Phe Val Ser
 1               5                  10                  15

Glu Val Lys Ala Ala Ile Val Leu Glu Glu Arg Tyr Asp Leu Val
                20                  25                  30

Glu Gly Gln Thr Leu Thr Val Lys Cys Pro Phe Asn Ile Met Lys Tyr
            35                  40                  45

Ala Asn Ser Gln Lys Ala Trp Gln Arg Leu Pro Asp Gly Lys Glu Pro
        50                  55                  60

Leu Thr Leu Val Val Thr Gln Arg Pro Phe Thr Arg Pro Ser Glu Val
 65                  70                  75                  80

His Met Gly Lys Phe Thr Leu Lys His Asp Pro Ser Glu Ala Met Leu
                85                  90                  95

Gln Val Gln Met Thr Asp Leu Gln Val Thr Asp Ser Gly Leu Tyr Arg
            100                 105                 110

Cys Val Ile Tyr His Pro Pro Asn Asp Pro Val Val Leu Phe His Pro
        115                 120                 125

Val Arg Leu Val Val Thr Lys Gly Ser Ser Asp Val Phe Thr Pro Val
130                 135                 140

Ile Ile Pro Ile Thr Arg Leu Thr Glu Arg Pro Ile Leu Ile Thr Thr
145                 150                 155                 160

Lys Tyr Ser Pro Ser Asp Thr Thr Thr Arg Ser Leu Pro Lys Pro
                165                 170                 175

Thr Ala Val Val Ser Ser Pro Gly Leu Gly Val Thr Ile Ile Asn Gly
            180                 185                 190

Thr Asp Ala Asp Ser Val Ser Thr Ser Ser Val Thr Ile Ser Val Ile
        195                 200                 205

Cys Gly Leu Leu Ser Lys Ser Leu Val Phe Ile Ile Leu Phe Ile Val
    210                 215                 220

Thr Lys Arg Thr Phe Gly
225                 230

<210> SEQ ID NO 3
<211> LENGTH: 23
<212> TYPE: PRT
<213> ORGANISM: Mus musculus

<400> SEQUENCE: 3

Leu Val Val Thr Gln Arg Pro Phe Thr Arg Pro Ser Glu Val His Met
 1               5                  10                  15

Gly Lys Phe Thr Leu Lys His
                20

<210> SEQ ID NO 4
<211> LENGTH: 23
<212> TYPE: PRT
<213> ORGANISM: Mus musculus

<400> SEQUENCE: 4

Val Ile Tyr His Pro Pro Asn Asp Pro Val Val Leu Phe His Pro Val
 1               5                  10                  15

Arg Leu Val Val Thr Lys Gly
                20
```

```
<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Thr Thr Arg Ser Leu Pro Lys Pro Thr Ala Val Val Ser Ser Pro
 1               5                  10                  15

Gly

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Gln Val Thr Asp Ser Gly Leu Tyr Arg Cys Val Ile Tyr His Pro
 1               5                  10                  15

Pro Asn Asp Pro Val
            20

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Gln Val Thr Asp Ser Gly Leu Tyr Arg Cys Val Ile Tyr His Pro
 1               5                  10                  15

Pro

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Thr Pro Lys His Gly Gln Arg Ser Thr His Val Thr Lys Phe Arg
 1               5                  10                  15

Val Phe Glu Pro Val Met Leu
            20

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Asp Ser Arg Cys Val Ile Gly Leu Tyr His Pro Pro Leu Gln Val
 1               5                  10                  15
```

Tyr

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttgtctcaga actccgagct gc                                              22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gagacatcgg cagttgactt gg                                              22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggacggagag atgcccaaga cc                                              22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
accagccagg agaatgacaa tg                                              22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggacgacatg gagaagatct gg                                              22

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atagtaatgt cacgcacgat ttcc                                           24

<210> SEQ ID NO 16
<211> LENGTH: 23
<212> TYPE: PRT
<213> ORGANISM: Homo sapiens

<400> SEQUENCE: 16

Leu Ala Cys Thr Glu Arg Pro Ser Lys Asn Ser His Pro Val Gln Val
1               5                   10                  15

Gly Arg Ile Ile Leu Glu Asp
            20

<210> SEQ ID NO 17
<211> LENGTH: 23
<212> TYPE: PRT
<213> ORGANISM: Homo sapiens

<400> SEQUENCE: 17

Val Ile Tyr Gln Pro Pro Lys Glu Pro His Met Leu Phe Asp Arg Ile
1               5                   10                  15

Arg Leu Val Val Thr Lys Gly
            20

<210> SEQ ID NO 18
<211> LENGTH: 21
<212> TYPE: PRT
<213> ORGANISM: Homo sapiens

<400> SEQUENCE: 18

Leu Gln Val Glu Asp Ser Gly Leu Tyr Gln Cys Val Ile Tyr Gln Pro
1               5                   10                  15

Pro Lys Glu Pro His
            20

<210> SEQ ID NO 19
<211> LENGTH: 17
<212> TYPE: PRT
<213> ORGANISM: Homo sapiens

<400> SEQUENCE: 19

Leu Gln Val Glu Asp Ser Gly Leu Tyr Gln Cys Val Ile Tyr Gln Pro
1               5                   10                  15

Pro

<210> SEQ ID NO 20
<211> LENGTH: 6
<212> TYPE: PRT
<213> ORGANISM: Homo sapiens

<400> SEQUENCE: 20

Arg Pro Ser Lys Asn Ser
1               5

<210> SEQ ID NO 21
<211> LENGTH: 5
<212> TYPE: PRT
<213> ORGANISM: Homo sapiens

<400> SEQUENCE: 21

Gln Pro Pro Lys Glu
1               5

```
<210> SEQ ID NO 22
<211> LENGTH: 6
<212> TYPE: PRT
<213> ORGANISM: Mus musculus

<400> SEQUENCE: 22

Arg Pro Phe Thr Arg Pro
  1               5

<210> SEQ ID NO 23
<211> LENGTH: 5
<212> TYPE: PRT
<213> ORGANISM: Mus musculus

<400> SEQUENCE: 23

His Pro Pro Asn Asp
  1               5

<210> SEQ ID NO 24
<211> LENGTH: 4
<212> TYPE: PRT
<213> ORGANISM: Homo sapiens

<400> SEQUENCE: 24

Gln Pro Pro Lys
  1

<210> SEQ ID NO 25
<211> LENGTH: 4
<212> TYPE: PRT
<213> ORGANISM: Mus musculus

<400> SEQUENCE: 25

His Pro Pro Asn
  1

<210> SEQ ID NO 26
<211> LENGTH: 230
<212> TYPE: PRT
<213> ORGANISM: Homo sapiens

<400> SEQUENCE: 26

Met Glu Pro Leu Arg Leu Leu Ile Leu Leu Phe Val Thr Glu Leu Ser
  1               5                  10                  15

Gly Ala His Asn Thr Thr Val Phe Gln Gly Val Ala Gly Gln Ser Leu
                 20                  25                  30

Gln Val Ser Cys Pro Tyr Asp Ser Met Lys His Trp Gly Arg Arg Lys
             35                  40                  45

Ala Trp Cys Arg Gln Leu Gly Glu Lys Gly Pro Cys Gln Arg Val Val
         50                  55                  60

Ser Thr His Asn Leu Trp Leu Leu Ser Phe Leu Arg Arg Trp Asn Gly
 65                  70                  75                  80

Ser Thr Ala Ile Thr Asp Asp Thr Leu Gly Gly Thr Leu Thr Ile Thr
                 85                  90                  95

Leu Arg Asn Leu Gln Pro His Asp Ala Gly Leu Tyr Gln Cys Gln Ser
                100                 105                 110

Leu His Gly Ser Glu Ala Asp Thr Leu Arg Lys Val Leu Val Glu Val
            115                 120                 125

Leu Ala Asp Pro Leu Asp His Arg Asp Ala Gly Asp Leu Trp Phe Pro
        130                 135                 140
```

```
Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
            165                 170                 175

Leu Leu Leu Ala Cys Ile Phe Leu Ile Lys Ile Leu Ala Ala Ser Ala
            180                 185                 190

Leu Trp Ala Ala Ala Trp His Gly Gln Lys Pro Gly Thr His Pro Pro
            195                 200                 205

Ser Glu Leu Asp Cys Gly His Asp Pro Gly Tyr Gln Leu Gln Thr Leu
            210                 215                 220

Pro Gly Leu Arg Asp Thr
225                 230

<210> SEQ ID NO 27
<211> LENGTH: 227
<212> TYPE: PRT
<213> ORGANISM: Mus musculus

<400> SEQUENCE: 27

Met Gly Pro Leu His Gln Phe Leu Leu Leu Ile Thr Ala Leu Ser
 1               5                  10                  15

Gln Ala Leu Asn Thr Thr Val Leu Gln Gly Met Ala Gly Gln Ser Leu
            20                  25                  30

Arg Val Ser Cys Thr Tyr Asp Ala Leu Lys His Trp Gly Arg Arg Lys
            35                  40                  45

Ala Trp Cys Arg Gln Leu Gly Glu Gly Pro Cys Gln Arg Val Val
    50                  55                  60

Ser Thr His Gly Val Trp Leu Leu Ala Phe Leu Lys Lys Arg Asn Gly
65                  70                  75                  80

Ser Thr Val Ile Ala Asp Asp Thr Leu Ala Gly Thr Val Thr Ile Thr
            85                  90                  95

Leu Lys Asn Leu Gln Ala Gly Asp Ala Gly Leu Tyr Gln Cys Gln Ser
            100                 105                 110

Leu Arg Gly Arg Glu Ala Glu Val Leu Gln Lys Val Leu Val Glu Val
            115                 120                 125

Leu Glu Asp Pro Leu Asp Asp Gln Asp Ala Gly Asp Leu Trp Val Pro
            130                 135                 140

Glu Glu Ser Ser Ser Phe Glu Gly Ala Gln Val Glu His Ser Thr Ser
145                 150                 155                 160

Arg Asn Gln Glu Thr Ser Phe Pro Pro Thr Ser Ile Leu Leu Leu Leu
            165                 170                 175

Ala Cys Val Leu Leu Ser Lys Phe Leu Ala Ala Ser Ile Leu Trp Ala
            180                 185                 190

Val Ala Arg Gly Arg Gln Lys Pro Gly Thr Pro Val Val Arg Gly Leu
            195                 200                 205

Asp Cys Gly Gln Asp Ala Gly His Gln Leu Gln Ile Leu Thr Gly Pro
            210                 215                 220

Gly Gly Thr
225
```